United States Patent
Bao et al.

(10) Patent No.: US 11,559,528 B2
(45) Date of Patent: Jan. 24, 2023

(54) BACE1 INHIBITION FOR THE TREATMENT OF CANCER

(71) Applicant: The Cleveland Clinic Foundation, Cleveland, OH (US)

(72) Inventors: Shideng Bao, Cleveland, OH (US); Kui Zhai, Beachwood, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 177 days.

(21) Appl. No.: 17/011,256

(22) Filed: Sep. 3, 2020

(65) Prior Publication Data

US 2021/0069205 A1    Mar. 11, 2021

Related U.S. Application Data

(60) Provisional application No. 62/896,053, filed on Sep. 5, 2019.

(51) Int. Cl.
| | |
|---|---|
| A61K 31/549 | (2006.01) |
| A61N 5/10 | (2006.01) |
| A61K 9/20 | (2006.01) |
| A61K 9/00 | (2006.01) |

(52) U.S. Cl.
CPC .......... *A61K 31/549* (2013.01); *A61K 9/0019* (2013.01); *A61K 9/20* (2013.01); *A61N 5/10* (2013.01)

(58) Field of Classification Search
CPC .............................. A61K 31/549; A61P 35/00
See application file for complete search history.

(56) References Cited

U.S. PATENT DOCUMENTS

2016/0318953 A1* 11/2016 Remick .................... A61P 43/00

OTHER PUBLICATIONS

Bao et al., Glioma stem cells promote radioresistance by preferential activation of the DNA damage response. Dec. 7, 2006;444(7120):756-60.
Bao et al., Stem cell-like glioma cells promote tumor angiogenesis through vascular endothelial growth factor. Aug. 15, 2006;66(16): 7843-7848.
Barker et al., The tumour microenvironment after radiotherapy: mechanisms of resistance and recurrence. Nat Rev Cancer. Jul. 2015;15(7):409-25.
Binnewies, et al., Understanding the tumor immune microenvironment (TIME) for effective therapy. Nat Med. May 2018;24(5):541-550.
Bray et al., Global cancer statistics 2018: GLOBOCAN estimates of incidence and mortality worldwide for 36 cancers in 185 countries. CA Cancer J Clin. Nov. 2018;68(6):394-424.
Butowski et al., Orally administered colony stimulating factor 1 receptor inhibitor PLX3397 in recurrent glioblastoma: an Ivy Foundation Early Phase Clinical Trials Consortium phase II study. Neuro Oncol. Apr. 2016;18(4):557-64.
Cebers et al., AZD3293: Pharmacokinetic and Pharmacodynamic Effects in Healthy Subjects and Patients with Alzheimer's Disease. J Alzheimers Dis . 2017;55(3):1039-1053.
Cheng et al., Glioblastoma stem cells generate vascular pericytes to support vessel function and tumor growth. Cell. Mar. 28, 2013;153(1):139-52.
Colegio et al., Functional polarization of tumour-associated macrophages by tumour-derived lactic acid. Nature. Sep. 25, 2014;513(7519):559-63.
Cooks et al., Mutant p53 cancers reprogram macrophages to tumor supporting macrophages via exosomal miR-1246. Nat Commun. Feb. 22, 2018;9(1):771.
Darmanis et al, Single-Cell RNA-Seq Analysis of Infiltrating Neoplastic Cells at the Migrating Front of Human Glioblastoma. Cell Rep. Oct. 31, 2017;21(5):1399-1410.
Deininger et al., Allograft inflammatory factor-1 defines a distinct subset of infiltrating macrophages/microglial cells in rat and human gliomas. Acta Neuropathol. Dec. 2000;100(6):673-80.
Egan et al., Randomized Trial of Verubecestat for Prodromal Alzheimer's Disease. N Engl J Med. Apr. 11, 2019;380(15):1408-1420.
Egan, et al.,Randomized Trial of Verubecestat for Mild-to-Moderate Alzheimer's Disease. N Engl J Med. May 3, 2018;378(18):1691-1703.
Eketjall et al., AZD3293: A Novel, Orally Active BACE1 Inhibitor with High Potency and Permeability and Markedly Slow Off-Rate Kinetics . J Alzheimers Dis. 2016;50(4):1109-23.
Fang et al., The zinc finger transcription factor ZFX is required for maintaining the tumorigenic potential of glioblastoma stem cells. Stem Cells. Aug. 2014;32(8):2033-47.
Fang et al., Deubiquitinase USP13 maintains glioblastoma stem cells by antagonizing FBXL14-mediated Myc ubiquitination. J Exp Med. Jan. 2017;214(1):245-267.
Farah et al.,Reduced BACE1 activity enhances clearance of myelin debris and regeneration of axons in the injured peripheral nervous system. J Neurosci. Apr. 13, 2011;31(15):5744-54.
Filley et al., Recurrent glioma clinical trial, CheckMate-143: the game is not over yet. Oncotarget. Oct. 6, 2017;8(53):91779-91794.
Fitzmaurice et al., Global, Regional, and National Cancer Incidence, Mortality, Years of Life Lost, Years Lived With Disability, and Disability-Adjusted Life-Years for 29 Cancer Groups, 1990 to 2016: A Systematic Analysis for the Global Burden of Disease Study. JAMA Oncol. Nov. 1, 2018;4(11):1553-1568.
Franklin et al., The cellular and molecular origin of tumor-associated macrophages. Science. May 23, 2014;344(6186):921-5.
Gelderblom et al., Nilotinib in locally advanced pigmented villonodular synovitis: a multicentre, open-label, single-arm, phase 2 trial. Lancet Oncol. May 2018;19(5):639-648.

(Continued)

*Primary Examiner* — Rei Tsang Shiao
(74) *Attorney, Agent, or Firm* — Casimir Jones, S.C.; Jason R. Bond

(57) ABSTRACT

Provided herein are compositions, systems, kits, and methods for treating a subject with cancer by administering a BACE1 inhibitor, such as MK-8931. In particular embodiments, the subject is treated with radiation (e.g., low dose radiation) first, and then administered a BACE1 inhibitor within a certain time window (e.g., about 3 hours to 6 days after the radiation treatment).

21 Claims, 22 Drawing Sheets
(21 of 22 Drawing Sheet(s) Filed in Color)
Specification includes a Sequence Listing.

(56) References Cited

OTHER PUBLICATIONS

Genard et al., Reprogramming of Tumor-Associated Macrophages with Anticancer Therapies: Radiotherapy versus Chemo- and Immunotherapies. Front Immunol. Jul. 14, 2017;8:828.
Glass et al., CNS macrophages and peripheral myeloid cells in brain tumours. Acta Neuropathol. Sep. 2014;128(3):347-62.
Guerriero, Macrophages: The Road Less Traveled, Changing Anticancer Therapy. Trends Mol Med. May 2018;24(5):472-489.
Guryanova et al., Nonreceptor tyrosine kinase BMX maintains self-renewal and tumorigenic potential of glioblastoma stem cells by activating STAT3. Cancer Cell. Apr. 12, 2011;19(4):498-511.
Hambardzumyan et al., The role of microglia and macrophages in glioma maintenance and progression. Nat Neurosci. Jan. 2016;19(1):20-7.
Highfill et al., Disruption of CXCR2-mediated MDSC tumor trafficking enhances anti-PD1 efficacy. Sci Transl Med. May 21, 2014;6(237):237ra67.
Hsiao et al., New evolutions in the BACE1 inhibitor field from 2014 to 2018. Bioorg Med Chem Lett. Mar. 15, 2019;29(6):761-777.
Hu et al., Tumor-associated macrophages in cancers. Clin Transl Oncol. Mar. 2016;18(3):251-8.
Hussain et al., Identification of a novel aspartic protease (Asp 2) as beta-secretase. Mol Cell Neurosci. Dec. 1999;14(6):419-27.
Jensen, Quantitative analysis of histological staining and fluorescence using ImageJ. Anat Rec (Hoboken). Mar. 2013;296(3):378-81.
Jung et al., Cancers with Higher Density of Tumor-Associated Macrophages Were Associated with Poor Survival Rates. J Pathol Transl Med. Jul. 2015;49(4):318-24.
Kennedy et al., The BACE1 inhibitor verubecestat (MK-8931) reduces CNS β-amyloid in animal models and in Alzheimer's disease patients. Sci Transl Med. Nov. 2, 2016;8(363):363ra150.
Kioi et al., Inhibition of vasculogenesis, but not angiogenesis, prevents the recurrence of glioblastoma after irradiation in mice. J Clin Invest. Mar. 2010;120(3):694-705.
Komohara et al., Possible involvement of the M2 anti-inflammatory macrophage phenotype in growth of human gliomas. J Pathol. Sep. 2008;216(1):15-24.
Kuang et al., Activated monocytes in peritumoral stroma of hepatocellular carcinoma foster immune privilege and disease progression through PD-L1. J Exp Med. Jun. 8, 2009;206(6):1327-37.
Lee et al., Cleavage of ST6Gal I by radiation-induced BACE1 inhibits golgi-anchored ST6Gal I-mediated sialylation of integrin β1 and migration in colon cancer cells. Radiat Oncol. Mar. 27, 2012;7:47.
Li et al., Hypoxia-inducible factors regulate tumorigenic capacity of glioma stem cells. Cancer Cell. Jun. 2, 2009;15(6):501-13.
Liu et al., Increased TNFR1 expression and signaling in injured peripheral nerves of mice with reduced BACE1 activity. Neurobiol Dis. Sep. 2016;93:21-7.
Lopez Lopez C., Caputo, A., Liu, F., Riviere, M.E., Rouzade-Dominguez, M.L., Thomas, R.G., Langbaum, J.B., Lenz, R., Reiman, E.M., Graf, A., et al. (2017). The Alzheimer's Prevention Initiative Generation Program: Evaluating CNP520 Efficacy in the Prevention of Alzheimer's Disease. J Prev Alzheimers Dis 4, 242-246.
Mantovani et al.,Tumour-associated macrophages as treatment targets in oncology. Nat Rev Clin Oncol. Jul. 2017;14(7):399-416.
Menon et al., Advances in Cancer Immunotherapy in Solid Tumors. Cancers (Basel). Nov. 24, 2016;8(12):106.
Mia et al., An optimized protocol for human M2 macrophages using M-CSF and IL-4/IL-10/TGF-β yields a dominant immunosuppressive phenotype. Scand J Immunol. May 2014;79(5):305-14.
Moussa-Pacha et al., BACE1 inhibitors: Current status and future directions in treating Alzheimer's disease. Med Res Rev. Jan. 2020;40(1):339-384.
Munn et al., Immune suppressive mechanisms in the tumor microenvironment. Curr Opin Immunol. Apr. 2016;39:1-6.
Murray, Macrophage Polarization. Annu Rev Physiol. Feb. 10, 2017;79:541-566.
Neumann et al., The BACE-1 inhibitor CNP520 for prevention trials in Alzheimer's disease. EMBO Mol Med. Nov. 2018;10(11):e9316.
Noy et al., Tumor-associated macrophages: from mechanisms to therapy. Immunity. Jul. 17, 2014;41(1):49-61.
Panza et al., BACE inhibitors in clinical development for the treatment of Alzheimer's disease. Expert Rev Neurother. Nov. 2018;18(11):847-857.
Papadopoulos et al., First-in-Human Study of AMG 820, a Monoclonal Anti-Colony-Stimulating Factor 1 Receptor Antibody, in Patients with Advanced Solid Tumors. Clin Cancer Res. Oct. 1, 2017;23(19):5703-5710.
Pyonteck, et al., CSF-1R inhibition alters macrophage polarization and blocks glioma progression. Nat Med. Oct. 2013;19(10):1264-72.
Qian et al., Macrophage diversity enhances tumor progression and metastasis. Cell. Apr. 2, 2010;141(1):39-51.
Quail et al., The Microenvironmental Landscape of Brain Tumors. Cancer Cell. Mar. 13, 2017;31(3):326-341.
Ruffell et al., Macrophage IL-10 blocks CD8+ T cell-dependent responses to chemotherapy by suppressing IL-12 expression in intratumoral dendritic cells. Cancer Cell. Nov. 10, 2014;26(5):623-37.
Ruffell et al., Macrophages and therapeutic resistance in cancer. Cancer Cell. Apr. 13, 2015;27(4):462-72.
Scott et al., Discovery of the 3-Imino-1,2,4-thiadiazinane 1,1-Dioxide Derivative Verubecestat (MK-8931)-A β-Site Amyloid Precursor Protein Cleaving Enzyme 1 Inhibitor for the Treatment of Alzheimer's Disease. J Med Chem. Dec. 8, 2016;59(23):10435-10450.
Sharma et al., Primary, Adaptive, and Acquired Resistance to Cancer Immunotherapy. Cell. Feb. 9, 2017;168(4):707-723.
Shi et al., Ibrutinib inactivates BMX-STAT3 in glioma stem cells to impair malignant growth and radioresistance. Sci Transl Med. May 30, 2018;10(443):eaah6816.
Shi et al., Tetraspanin CD9 stabilizes gp130 by preventing its ubiquitin-dependent lysosomal degradation to promote STAT3 activation in glioma stem cells. Cell Death Differ. Jan. 2017;24(1):167-180.
Shi et al., Tumour-associated macrophages secrete pleiotrophin to promote PTPRZ1 signalling in glioblastoma stem cells for tumour growth. Nat Commun. Jun. 1, 2017;8:15080.
Sica et al., Macrophage plasticity and polarization: in vivo veritas. J Clin Invest. Mar. 2012; 122(3):787-95.
Sica et al., Macrophage polarization in tumour progression. Semin Cancer Biol. Oct. 2008;18(5):349-55.
Sica et al., Tumour-associated macrophages are a distinct M2 polarised population promoting tumour progression: potential targets of anti-cancer therapy. Eur J Cancer. Apr. 2006;42(6):717-27.
Sinha et al., Purification and cloning of amyloid precursor protein beta-secretase from human brain. Nature. Dec. 2, 1999;402(6761):537-40.
Sorensen et al., Tumour-associated microglia/macrophages predict poor prognosis in high-grade gliomas and correlate with an aggressive tumour subtype. Neuropathol Appl Neurobiol. Feb. 2018;44(2):185-206.
Sperduto et al., Diagnosis-specific prognostic factors, indexes, and treatment outcomes for patients with newly diagnosed brain metastases: a multi-institutional analysis of 4,259 patients. Int J Radiat Oncol Biol Phys. Jul. 1, 2010;77(3):655-61.
Su et al., Immune Checkpoint Inhibition Overcomes ADCP-Induced Immunosuppression by Macrophages. Cell. Oct. 4, 2018;175(2):442-457.e23.
Thaisrivongs et al., Synthesis of Verubecestat, a BACE1 Inhibitor for the Treatment of Alzheimer's Disease. Org Lett. Nov. 18, 2016;18(22):5780-5783.
Van Wilgenburg et al., Efficient, long term production of monocyte-derived macrophages from human pluripotent stem cells under partly-defined and fully-defined conditions. PLoS One. Aug. 12, 2013;8(8):e71098.
Vassar et al., Beta-secretase cleavage of Alzheimer's amyloid precursor protein by the transmembrane aspartic protease BACE. Science. Oct. 22, 1999;286(5440):735-41.

(56) References Cited

OTHER PUBLICATIONS

Vatner et al., Myeloid-derived cells in tumors: effects of radiation. Semin Radiat Oncol. Jan. 2015;25(1):18-27.

Wang et al., Reciprocal Signaling between Glioblastoma Stem Cells and Differentiated Tumor Cells Promotes Malignant Progression. Cell Stem Cell. Apr. 5, 2018;22(4):514-528.e5.

Wang et al., Tumor Evolution of Glioma-Intrinsic Gene Expression Subtypes Associates with Immunological Changes in the Microenvironment. Cancer Cell. Jul. 10, 2017;32(1):42-56.e6.

Weischenfeldt et al., Bone Marrow-Derived Macrophages (BMM): Isolation and Applications. CSH Protoc. Dec. 1, 2008;2008:pdb.prot5080.

Xie et al., N 6-methyladenine DNA Modification in Glioblastoma. Cell. Nov. 15, 2018;175(5):1228-1243.e20.

Yan et al., Membrane-anchored aspartyl protease with Alzheimer's disease beta-secretase activity. Nature. Dec. 2, 1999;402(6761):533-7.

Yan et al., Targeting the β secretase BACE1 for Alzheimer's disease therapy. Lancet Neurol. Mar. 2014;13(3):319-29.

Yan, Physiological Functions of the β-Site Amyloid Precursor Protein Cleaving Enzyme 1 and 2. Front Mol Neurosci. Apr. 19, 2017;10:97.

Yanagimachi et al., Robust and highly-efficient differentiation of functional monocytic cells from human pluripotent stem cells under serum- and feeder cell-free conditions. PLoS One. 2013;8(4):e59243.

Yang et al., Tumor-associated macrophages: from basic research to clinical application. J Hematol Oncol. Feb. 28, 2017;10(1):58.

Yu et al., STATs in cancer inflammation and immunity: a leading role for STAT3. Nat Rev Cancer. Nov. 2009;9(11):798-809.

Zhou et al., Periostin secreted by glioblastoma stem cells recruits M2 tumour-associated macrophages and promotes malignant growth. Nat Cell Biol. Feb. 2015;17(2):170-82.

Zhou et al., Reciprocal Supportive Interplay between Glioblastoma and Tumor-Associated Macrophages. Cancers (Basel). Mar. 26, 2014;6(2):723-40.

Zhou et al., Targeting Glioma Stem Cell-Derived Pericytes Disrupts the Blood-Tumor Barrier and Improves Chemotherapeutic Efficacy. Cell Stem Cell. Nov. 2, 2017;21(5):591-603.e4.

\* cited by examiner

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial sequence
<220> FEATURE:
<223> OTHER INFORMATION: BACE1 Forward Primer

<400> SEQUENCE: 1
gcagggctac tacgtggaga                                                  20

<210> SEQ ID NO 2
<211> LENGTH: 21
<212> TYPE: DNA
<213> ORGANISM: Artificial sequence
<220> FEATURE:
<223> OTHER INFORMATION: BACE1 Reverse Primer

<400> SEQUENCE: 2
gtatccacca ggatgttgag c                                                21

<210> SEQ ID NO 3
<211> LENGTH: 21
<212> TYPE: DNA
<213> ORGANISM: Artificial sequence
<220> FEATURE:
<223> OTHER INFORMATION: GAPDH Forward Primer

<400> SEQUENCE: 3
aaggtgaagg tcggagtcaa c                                                21

<210> SEQ ID NO 4
<211> LENGTH: 22
<212> TYPE: DNA
<213> ORGANISM: Artificial sequence
<220> FEATURE:
<223> OTHER INFORMATION: GAPDH Reverse Primer

<400> SEQUENCE: 4
ggggtcattg atggcaacaa ta                                               22

<210> SEQ ID NO 5
<211> LENGTH: 27
<212> TYPE: DNA
<213> ORGANISM: Artificial sequence
<220> FEATURE:
<223> OTHER INFORMATION: tdTomato Forward Primer

<400> SEQUENCE: 5
gctagcccaa tcatttaaat ataactt                                          27

<210> SEQ ID NO 6
<211> LENGTH: 31
<212> TYPE: DNA
<213> ORGANISM: Artificial sequence
<220> FEATURE:
<223> OTHER INFORMATION: tdTomato Reverse

<400> SEQUENCE: 6
gcggccgctt acttgtacag ctcgtccatg c                                     31
```

BACE1 INHIBITION FOR THE TREATMENT OF CANCER

The present application claims priority to U.S. Provisional application Ser. No. 62/896,053, filed Sep. 5, 2019, which is herein incorporated by reference in its entirety.

FIELD

Provided herein are compositions, systems, kits, and methods for treating a subject with cancer by administering a BACE1 inhibitor, such as MK-8931. In particular embodiments, the subject is treated with radiation (e.g., low dose radiation) first, and then administered a BACE1 inhibitor within a certain time window (e.g., about 3 hours to 6 days after the radiation treatment).

BACKGROUND

GBM and brain metastases of lung ADC are highly lethal cancers containing abundant TAMs, and current immunotherapy such as anti-PD1 treatment is not effective for these tumors partially due to the blood-brain barrier (BBB) or blood-tumor barrier (BTB) issue and the insufficient infiltration of T cells into tumors. GBM and brain metastases of lung ADC are highly resistant to current therapies and often recurs rapidly after surgical resection and radio-chemotherapy. The majority of these brain tumors showed extremely poor or no response to current immunotherapy. Less than 7% of GBM patients showed response to current immune checkpoint inhibitors including anti-PD1 treatment (Filley et al., 2017). Brain metastases of lung ADC respond to current immunotherapy even more poorly, although tumor immunotherapy has been shown promising for 20-30% of other types of solid cancers including primary lung cancers (Menon et al., 2016). Thus, developing effective therapeutics to improve immunotherapy for GBM and brain metastases is urgently needed.

SUMMARY

Provided herein are compositions, systems, kits, and methods for treating a subject with cancer by administering a BACE1 inhibitor, such as MK-8931. In particular embodiments, the subject is treated with radiation (e.g., low dose radiation) first, and then administered a BACE1 inhibitor within a certain time window (e.g., about 3 hours to 6 days after the radiation treatment).

In some embodiments, provided here are methods of treating a subject with cancer comprising: a) treating a subject having cancer with radiation, and b) administering a BACE1 inhibitor to the subject. In certain embodiments, provided herein are methods of treating a subject with cancer comprising: administering a BACE1 inhibitor from Table 1 to the subject or a shRNA, wherein the subject has cancer. In certain embodiments, provided herein are the same methods except an ERK inhibitor or a MEK inhibitor is used in place of a BACE1 inhibitor or in addition to a BACE1 inhibitor.

In particular embodiments, the administering comprises providing the BACE1 inhibitor to the subject in the form of oral pills that the patient takes themselves. In other embodiments, the administering comprises injecting the BACE1 inhibitor into the subject. In some embodiments, the methods further comprise: repeating the administering daily for at least one week or at least three weeks (e.g., at least 7 . . . 14 . . . 21 . . . 28 . . . 35 . . . or 100 days). In certain embodiments, the administering comprises administering (e.g., daily for at least three weeks) 0.05 mg per kg of the subject to 50 mg per kg of the subject (e.g., 0.05 . . . 1.0 . . . 10 . . . 30 . . . or 50 mg/kg), or administering a total dose (e.g., daily for at least three weeks) of 3-1000 mg (e.g., 3 . . . 100 . . . 400 . . . 800 . . . 1000 mg).

In particular embodiments, the treating with radiation occurs at least about 3 hours, or at least 12 hours, prior to the administering (e.g., at least 3 . . . 12 . . . 36 hours prior to the administering). In further embodiments, the administering occurs no later than 6 days after the treating with radiation (e.g., no later than 5 . . . 4 . . . or 3 days after the treating with radiation). In particular embodiments, the radiation is low-dose radiation. In some embodiments, the low-dose radiation provides between 0.1-10 Gy, or 1-5 Gy, of radiation to the subject (e.g., 0.1 . . . 0.9 . . . 2 . . . 3.5 . . . 5.5 . . . 7.5 . . . 8.3 . . . 10.0 Gy). In certain embodiments, rather than radiation treatment, or in addition thereto, the subject is treated to disrupt the blood-brain barrier or blood-tumor barrier in brain tumors or brain metastases of the subject.

In certain embodiments, the subject is a human. In other embodiments, the cancer is selected from the group consisting of: a brain cancer, glioblastoma multiforme, brain metastases, lung adenocarcinoma, liver cancer, and gastric cancer. In particular embodiments, the BACE1 inhibitor is selected from Table 1. In certain embodiments, the BACE1 inhibitor comprises MK-8931. In further embodiments, the methods further comprise: administering the subject an immune checkpoint inhibitor.

In particular embodiments, the cancer is selected from the group consisting of: glioblastoma, lung cancer, pancreatic cancer, breast cancer, myeloid cancers, lymphoid cancers (e.g., T-cell lymphoid cancers), small cell lung cancer, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

DESCRIPTION OF THE FIGURES

The patent or application file contains at least one drawing executed in color. Copies of this patent or patent application publication with color drawings will be provided by the Office upon request and payment of the necessary fee.

p<0.01. (K and L) GSC population analysis by immunofluorescent staining of SOX2 in the GSC-derived xenografts treated with MK-8931 or the vehicle control. Frozen sections were immunostained with a specific antibody against the GSC marker SOX2 (in green) and counterstained with DAPI (in blue). Representative immunofluorescent images of SOX2 (K) in the GBM xenografts treated with MK-8931 or the vehicle control were shown. Quantification (L) shows that MK-8931 treatment significantly reduced GSCs (SOX2$^+$ cells) in the GBM xenografts.  p<0.01. Data are shown as mean SEM. * p<0.05,  p<0.01, * p<0.001, and NS (not significant)≥0.05; Student's t-test. Scale bar represents 30 µM. Ctl: Control; MK: MK-8931.

Figure 6:
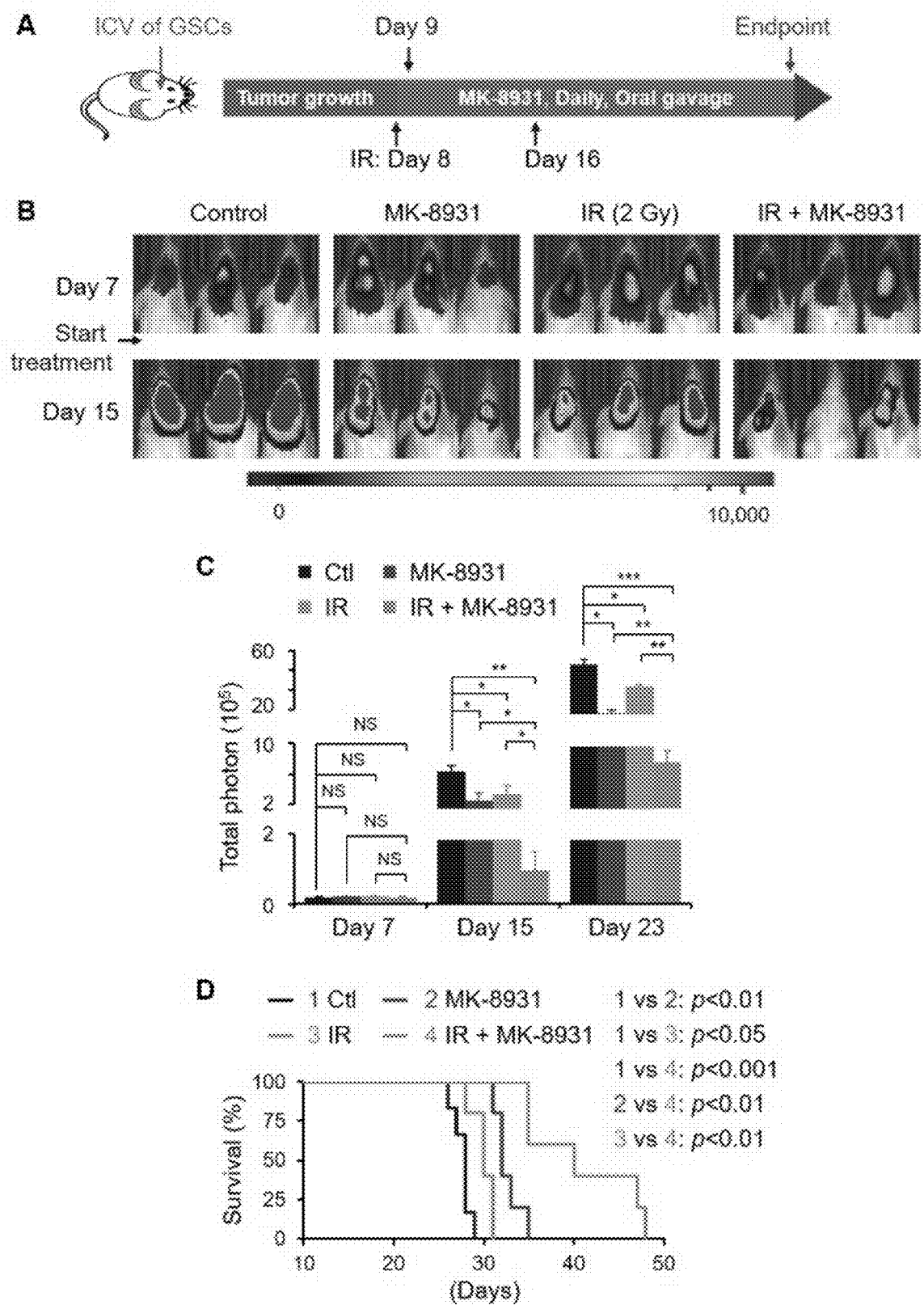

FIG. 6, panels A-D. Low Dose of Irradiation Synergized with MK-8931 Treatment to Suppress GBM Tumor Growth and Prolong Survival of Tumor-bearing Animals. (A) A treatment schedule showing an exemplary preclinical trial of MK-8931 treatment in combination with low dose of irradiation (IR) in GBM xenograft models. Glioma stem cells (T4121 GSCs) expressing luciferase were transplanted into mouse brains through intracranial injection to establish orthotopic GBM xenografts. Irradiation (2 Gy) was performed on Day 8 and Day 16. From Day 9, mice were treated with MK-8931 (30 mg/kg) or the vehicle control once daily by oral gavage until the appearance of humane endpoints. Bioluminescent imaging (IVIS) were performed twice per week to monitor tumor growth before and after IR and MK-8931 treatment. (B and C) In vivo bioluminescent analysis of tumor growth in mouse brains bearing the GSC-derived GBM xenografts treated with MK-8931, IR, IR plus MK-8931, or the vehicle control. Representative bioluminescent images (B) at day 7 (before treatment) and day 15 (treatment for one week) are shown. Quantifications (C) show the mean bioluminescence of the control group (5 mice), MK-8931-treated group (5 mice), IR (2 Gy)-treated group (5 mice), or IR+MK-8931 treated group (5 mice) at Days 7, 15 and 25. Low dose of IR significantly synergized with MK-8931 treatment to inhibit GBM tumor growth. Data are shown as mean±SEM. * p<0.05, ** p<0.01, * ** p<0.001, and NS (not significant)≥0.05 as indicated; Student's t-test. Ctl: Control; IR: Irradiation. (D) Kaplan-Meier survival curves of the mice bearing the GSC-derived GBM xenografts treated MK-8931, IR, IR plus MK-8931, or the vehicle control. Low dose of IR synergized with MK-8931 treatment to extend survival of the tumor-bearing animals. Data are shown as mean±SEM. Log-rank analysis was used to assess the significance. Significances were shown as indicated. Ctl: Control; IR: irradiation.

Figure 7:
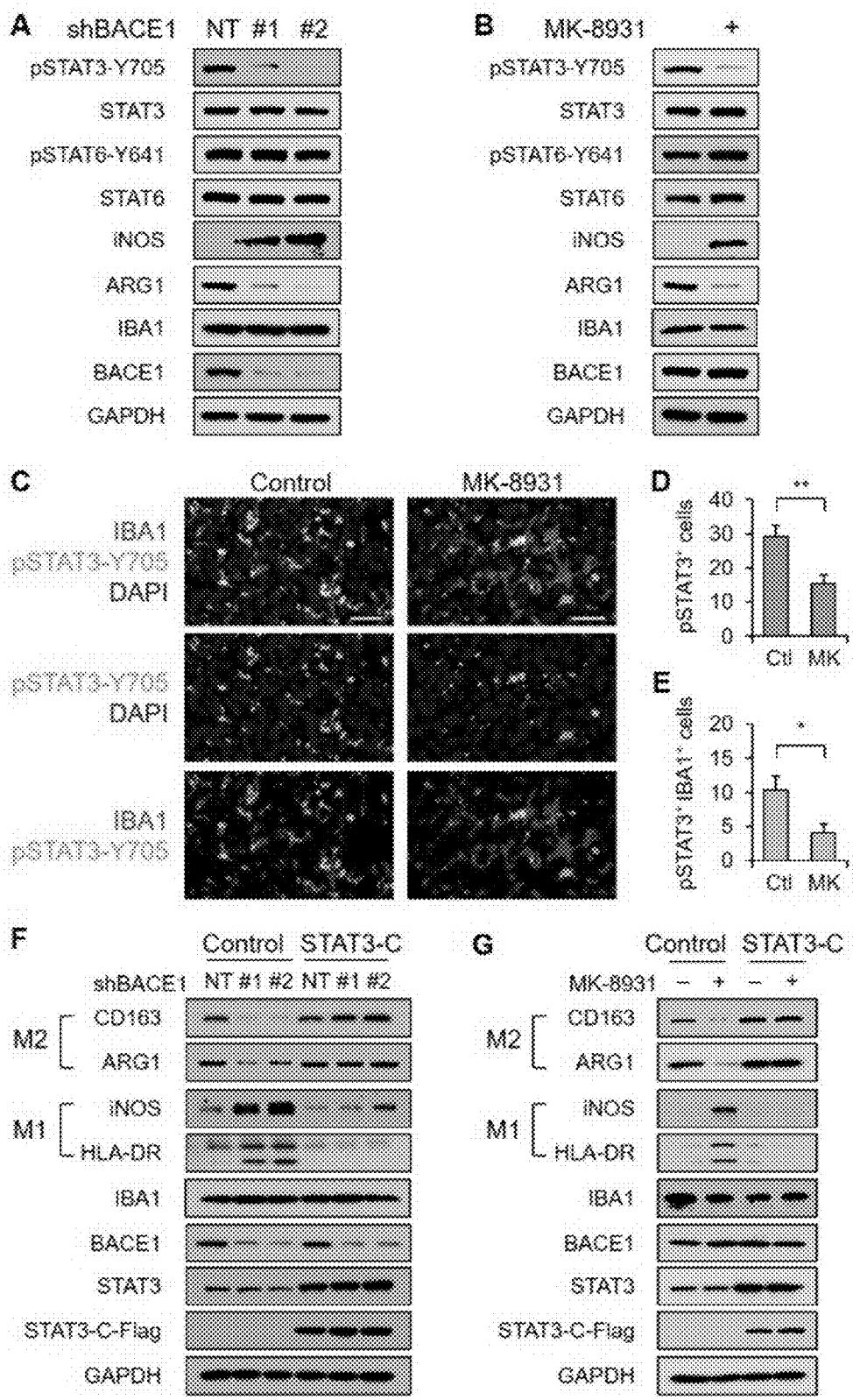

FIG. 7, panels A-G. BACE1 Maintains M2 Macrophages through STAT3 Activation (A) Immunoblot analyses of STAT3 and STAT6 activation (pSTAT3-Y705 and pSTAT6-Y641) in U937-derived M2 macrophages affected by BACE1 knockdown. U937-derived M2 macrophages were transduced with shNT (non-targeting control shRNA) or shBACE1 through lentiviral infection for three days and then harvested for immunoblot analyses of pSTAT3-Y705, STAT3, pSTAT6-Y641, STAT6, iNOS (M1 marker), ARG1 (M2 marker), IBA1 (total macrophage marker), BACE1, and GAPDH (loading control). (B) Immunoblot analysis of STAT3 and STAT6 activation (pSTAT3-Y705 and pSTAT6-Y641) in U937-derived M2 macrophages in response to MK-8931 treatment. U937-derived M2 macrophages were treated with MK-8931 (50 µg/mL) or the vehicle control for three days and then harvested for analyses of pSTAT3-Y705, STAT3, pSTAT6-Y641, STAT6, iNOS (M1 marker), ARG1 (M2 marker), IBA1 (total macrophage marker), BACE1, and GAPDH (loading control). (C-E) In vivo analysis of STAT3 activating phosphorylation in TAMs by double immunofluorescent staining of IBA1 with pSTAT3-Y705 in GBM xenografts treated with MK-8931 or vehicle control. GBM xenografts were established by implantation of glioma stem cells (T4121) through intracranial injection. Seven days after transplantation, the tumor-bearing mice were treated with MK-8931 (30 mg/kg) or the vehicle control once daily by oral gavage for two weeks. Frozen brain sections bearing the xenografts were immunostained with specific antibodies against IBA1 (in green) pSTAT3-Y705 (in red) and counterstained with DAPI (in blue). Representative images (C) showing the fluorescent staining of IBA1 (in green) and the pSTAT3 (in red) in MK-8931-treated or control GBM xenografts. Quantification of pSTAT3$^+$ cells (D) shows that MK-8931 treatment significantly reduced STAT3 activating phosphorylation in GBM xenografts. Quantification of IBA1$^+$/pSTAT3$^+$ double positive cells (E) shows that MK-8931 treatment significantly reduced STAT3 activating phosphorylation in TAMs in GBM xenografts. Data are shown as mean±SEM. * p<0.05 and ** p<0.01; Student's t-test. Scale bar represents 3 µM. Ctl: Control. MK: MK-8931. (F) Immunoblot analyses of the M2 macrophage markers (CD163 and ARG1) and the M1 macrophage markers (iNOS and HLA-DR) in U937-derived M2 macrophages transduced with the constitutively activated STAT3 (STAT3-C-Flag) or vector (control) in combination with shBACE1 or NT shRNA through lentiviral infection. Three days after the transduction, the U937-derived M2 macrophages were harvested for immunoblot analyses of CD163, ARG1, iNOS, HLA-DR, IBA1, BACE1, STAT3, Flag (STAT3-C) and GAPDH (loading control). Ectopic expression of STAT3-C attenuated the M2 to M1 switch caused by BACE1 knockdown. (G) Immunoblot analyses of the M2 macrophage markers (CD163 and ARG1) and M1 macrophage markers (iNOS and HLA-DR) in U937-derived M2 macrophages transduced with the constitutively activated STAT3 (STAT3-C-Flag) or vector (control) in combination with treatment of MK-8931 (50 µg/mL). U937-derived M2 macrophages were transduced with STAT3-C-Flag or the vector control and then treated with MK-8931 (50 µg/mL) or the vehicle control for three days, and then harvested for immunoblot analyses of CD163, ARG1, iNOS, HLA-DR, IBA1, BACE1, STAT3, Flag (STAT3-C) and GAPDH (loading control). Ectopic expression of STAT3-C attenuated the M2 to M1 switch induced by MK-8931 treatment.

Figure 8:
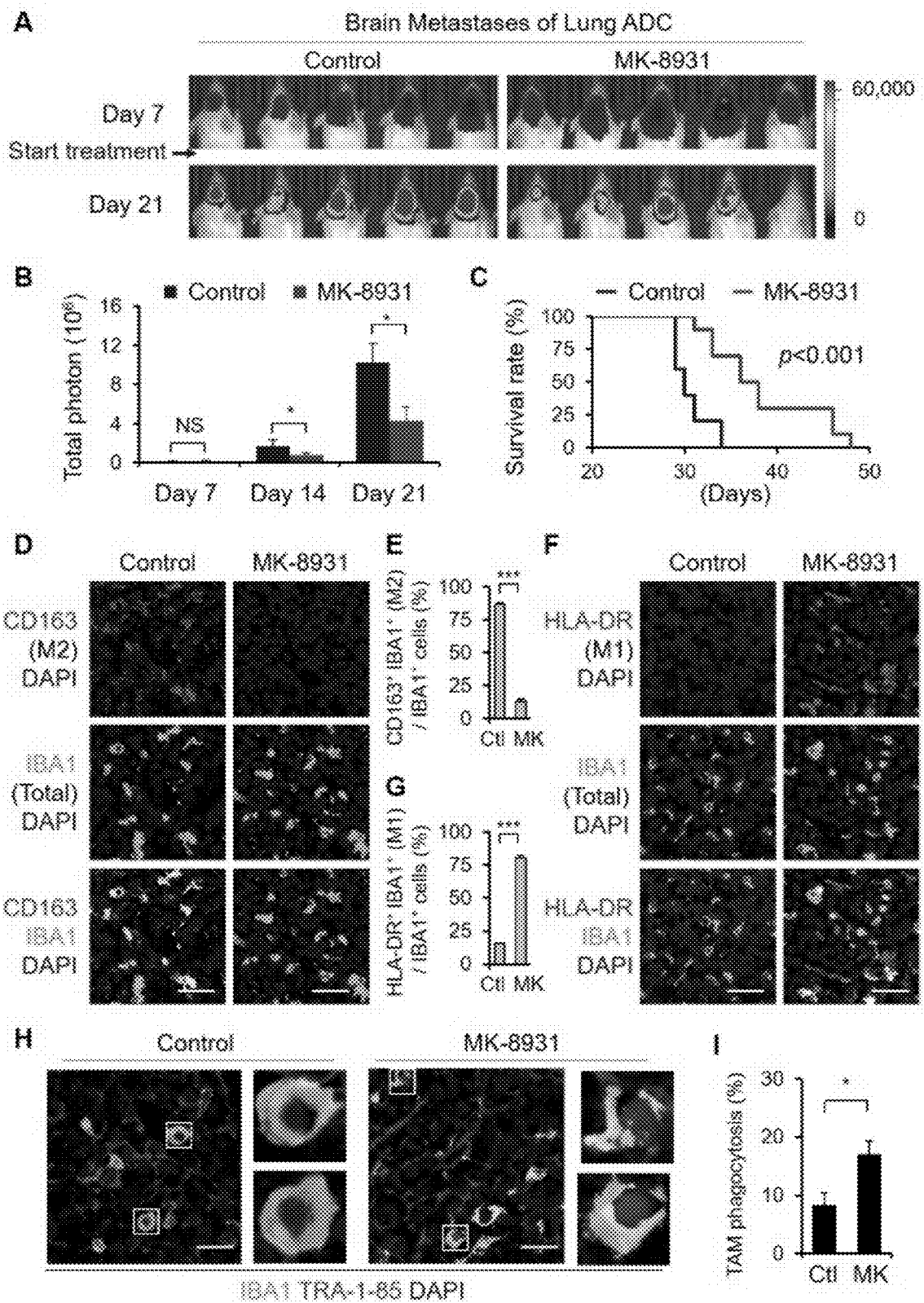

FIG. 8, panels A-I. MK-8931 Treatment Potently Suppressed Malignant Growth of Brain Metastases of Lung Adenocarcinoma. (A-C) An exemplary preclinical trial of MK-8931 treatment for brain metastases of lung adenocarcinoma (ADC) in xenograft models. The lung cancer cells (H1002, ADC) expressing luciferase were transplanted into mouse brains to establish intracranial xenografts of lung ADC. One week after the transplantation, mice bearing the tumors were treated with MK-8931 (30 mg/kg) or the vehicle control once daily by oral gavage until the appearance of humane endpoints. Representative bioluminescent images (A) on day 7 (before treatment) and day 21 (treatment for two weeks) are shown. Quantification of the mean bioluminescence (B) of lung ADC xenografts from the group treated with MK-8931 (10 mice) or vehicle control on Days 7 (before treatment), 14 and 21 shows that MK-8931 treatment significantly inhibited tumor growth of lung ADC brain metastases. Kaplan-Meier survival curves of the MK-8931 treated mice and the control mice. MK-8931 treatment significantly extended the survival of animals bearing the intracranial lung ADC xenografts (p<0.001 by log-rank analysis). * p<0.05 and NS (not significant)≥0.05. (D and E) Density analysis of M2 TAMs by double immunofluorescent staining of the total TAM marker IBA1 (in green) and the M2 TAM marker CD163 (in red) in the intracranial lung ADC xenografts treated with MK-8931 or the vehicle control. Frozen tumor sections were immunostained with specific antibodies against IBA1 (in green) and CD163 (in red) and counterstained with DAPI (in blue). Representative immunofluorescent images (D) showing the staining of IBA1 and the M2 TAM marker CD163 in the intracranial lung ADC xenografts treated with MK-8931 or the vehicle control. Quantification (E) of M2 TAMs (CD163+/IBA1$^+$ cells) in the intracranial lung ADC xenografts shows that MK-8931 treatment significantly reduced M2 TAMs. * p<0.001. (F and G) Density analysis of M1 TAMs by double immunofluorescent staining of the total TAM marker IBA1 (in green) and the M1 TAM marker HLA-DR (in red) in the intracranial lung ADC xenografts treated with MK-8931 or the vehicle control. Frozen tumor sections were co-stained with specific antibodies against IBA1 (in green) and HLA-DR (in red) and counterstained with DAPI (in blue). Representative immunofluorescent images (F) showing the staining of IBA1 (in green) and the M1 TAM marker HLA-DR (in red) in the intracranial lung ADC xenografts treated with MK-8931 or the vehicle control. Quantification (G) of M1 TAMs (HLA-DR$^+$/IBA1$^+$ cells) the intracranial lung ADC xenografts shows that MK-8931 treatment significantly increased M1 TAMs. * p<0.001. (H and I) Detection of in vivo phagocytosis of TAMs against human cancer cells in the intracranial lung ADC xenografts treated with MK-8931 by double immunofluorescent staining of the TAM marker IBA1 and the human specific antigen TRA-85. Frozen tumor sections were co-stained with specific antibodies against IBA1 (in green) with TRA-1-85 (in red) and counterstained with DAPI (in blue). Representative immunofluorescent images (H) showing the staining of IBA1 (in green) and TRA-1-85 (in red) in the intracranial lung ADC xenografts treated with MK-8931 or the vehicle control. Phagocytosis was detected as inclusion bodies of cancer cells (in red) within TAMs (in green) in the MK-8931-treated xenografts. Quantification of in vivo phagocytosis (I) shows that MK-8931 treatment significantly increased TAM phagocytosis against human lung ADC cells. * p<0.05. Data are shown as mean±SEM. * p<0.05, *** p<0.001, and NS (not significant)≥0.05; Student's t-test. Scale bar represents 30 μM. Ctl: Control; MK: MK-8931.

Figure 9:
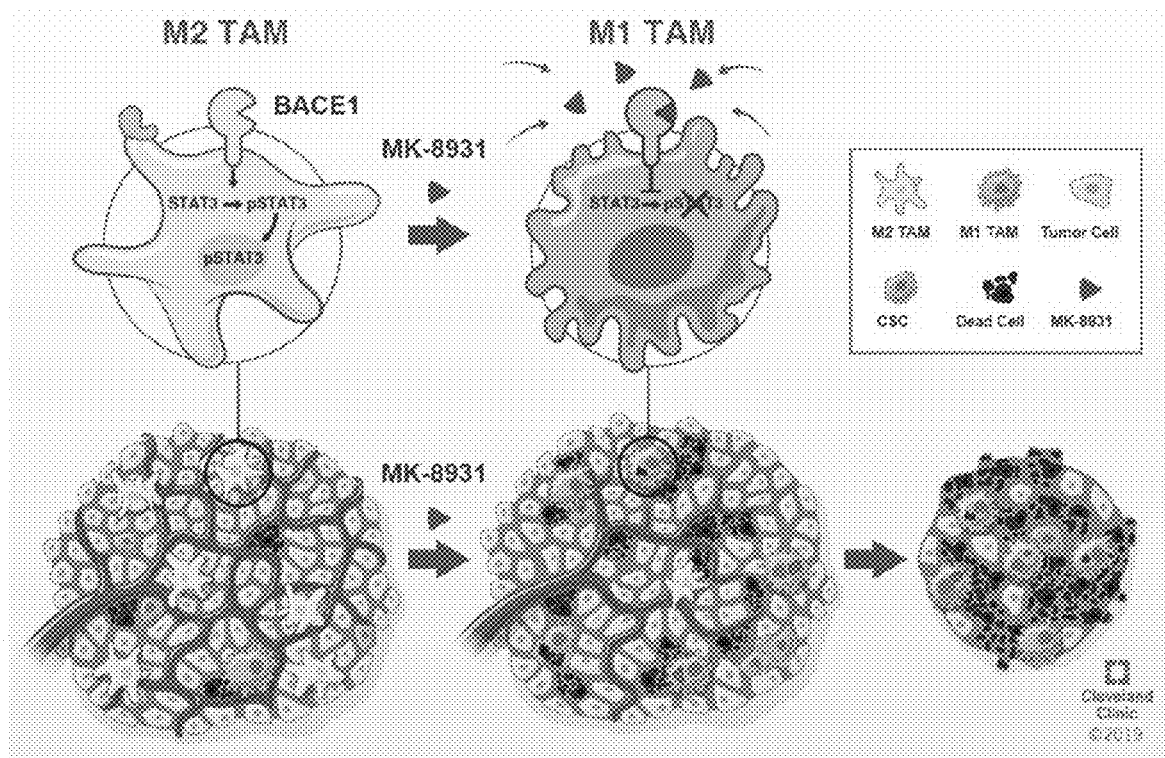

FIG. 9. A Schematic Illustration Shows that BACE1 Inhibition by MK-8931 Converts M2 TAMs into M1 Macrophages to Promote TAM Phagocytosis and Suppress Tumor Growth. Most malignant tumors including GBMs and brain metastases of lung adenocarcinoma contain abundant tumor-supportive TAMs (M2). BACE1-mediated STAT3 activation is required for maintaining M2 TAMs. Targeting BACE1 by its inhibitor MK-8931 converts M2 TAMs into tumor-suppressive M1 macrophages to phagocytize tumor cells and reprogram the tumor microenvironment. Importantly, BACE1 inhibition by MK-8931 potently suppresses malignant growth of lethal tumors, highlighting the promising therapeutic potential of MK-8931 for the macrophage-based immunotherapy to improve patient survival.

Figure 10:
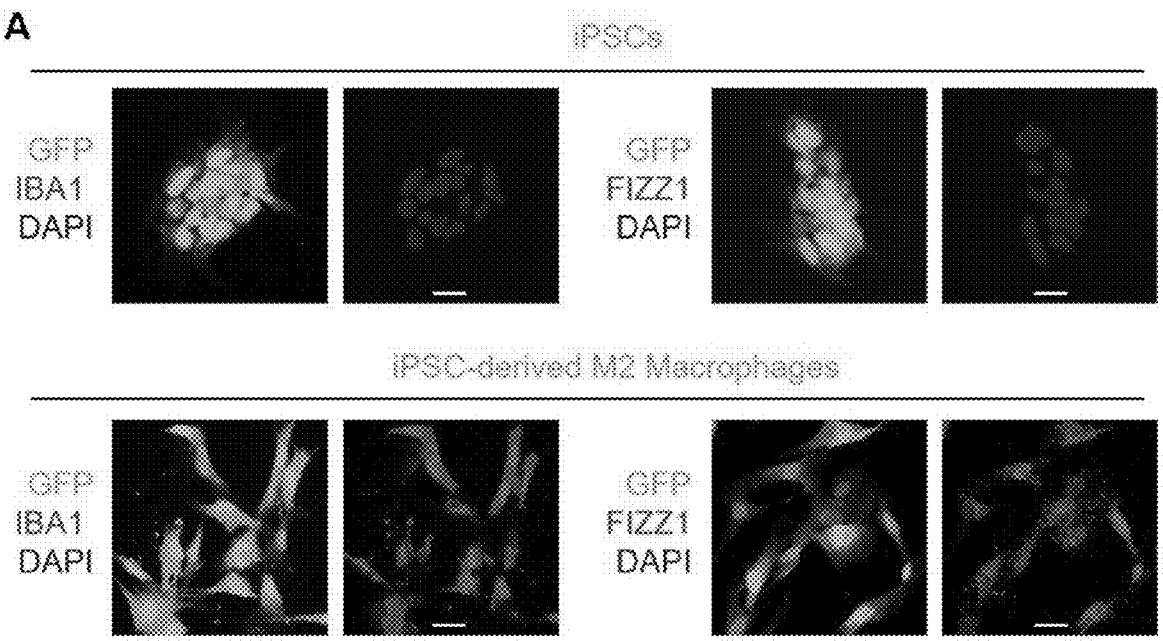
Figure 10:
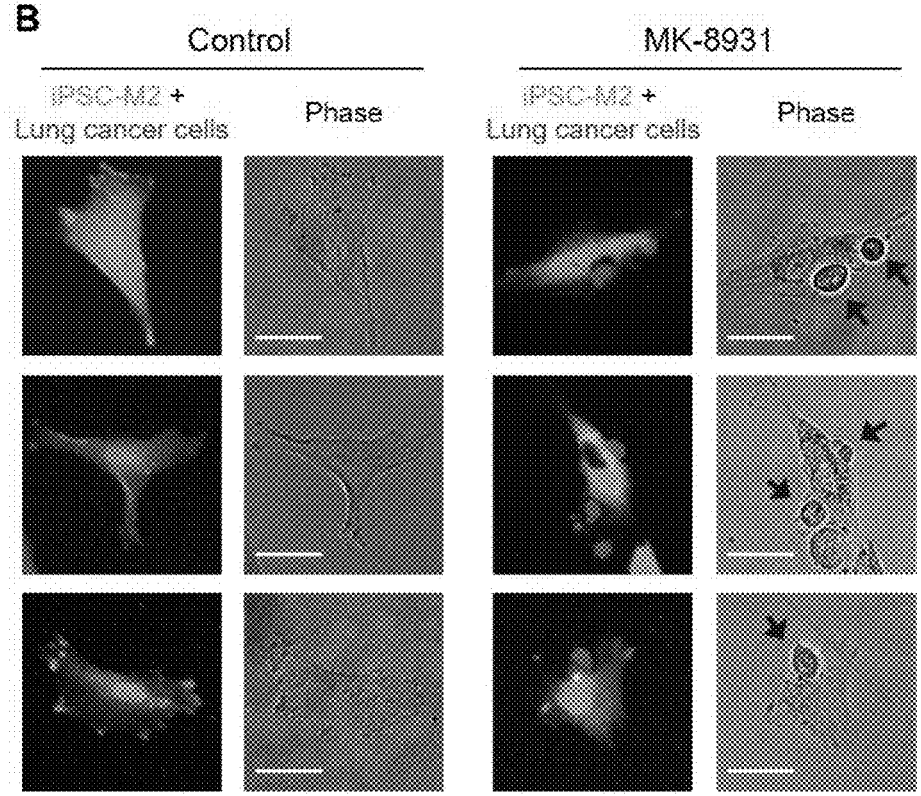
Figure 10:
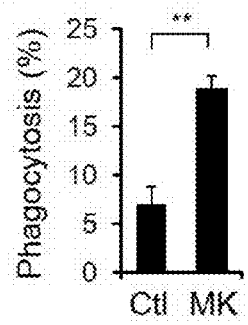

FIG. 10, panels A-C. MK-8931 Treatment Promotes Phagocytosis of iPSC-derived M2 Macrophages against Human Lung ADC Cancer Cells. (A) Immunofluorescent analysis of macrophage marker expression in iPSC-derived M2 macrophages. The iPSC-derived M2 macrophages (GFP+) and the matched iPSCs (GFP+, control) were stained with specific antibodies against IBA1 (total macrophage marker, in red) and FIZZ1 (M2 macrophage marker, in red) and then counterstained with DAPI (in blue). Representative immunofluorescent images show that IBA1 and FIZZ1 were expressed by the iPSC-derived M2 macrophages but not by the iPSCs. (B and C) In vitro macrophage phagocytosis assay showing that the BACE1 inhibitor MK-8931 promoted phagocytosis of the iPSC-derived macrophages against human lung ADC cancer cells. The iPSC-derived M2 macrophages (GFP+) were treated with MK-8931 (50 g/mL) or the vehicle control for two days and then co-incubated with the tdTomato-expressing human lung ADC cells (H1002, in red) to detect macrophage phagocytosis as illustrated in (B). Representative fluorescent and phase contrast images (B) and quantification (C) showing that MK-8931 potently induced phagocytosis of iPSC-derived macrophages (in green) against human lung ADC cancer cells (in red). Data are shown as mean±SEM, ** p<0.01; Student's t test. Scale bars represent 3 μM. Ctl: Control; MK: MK-8931.

Figure 11:
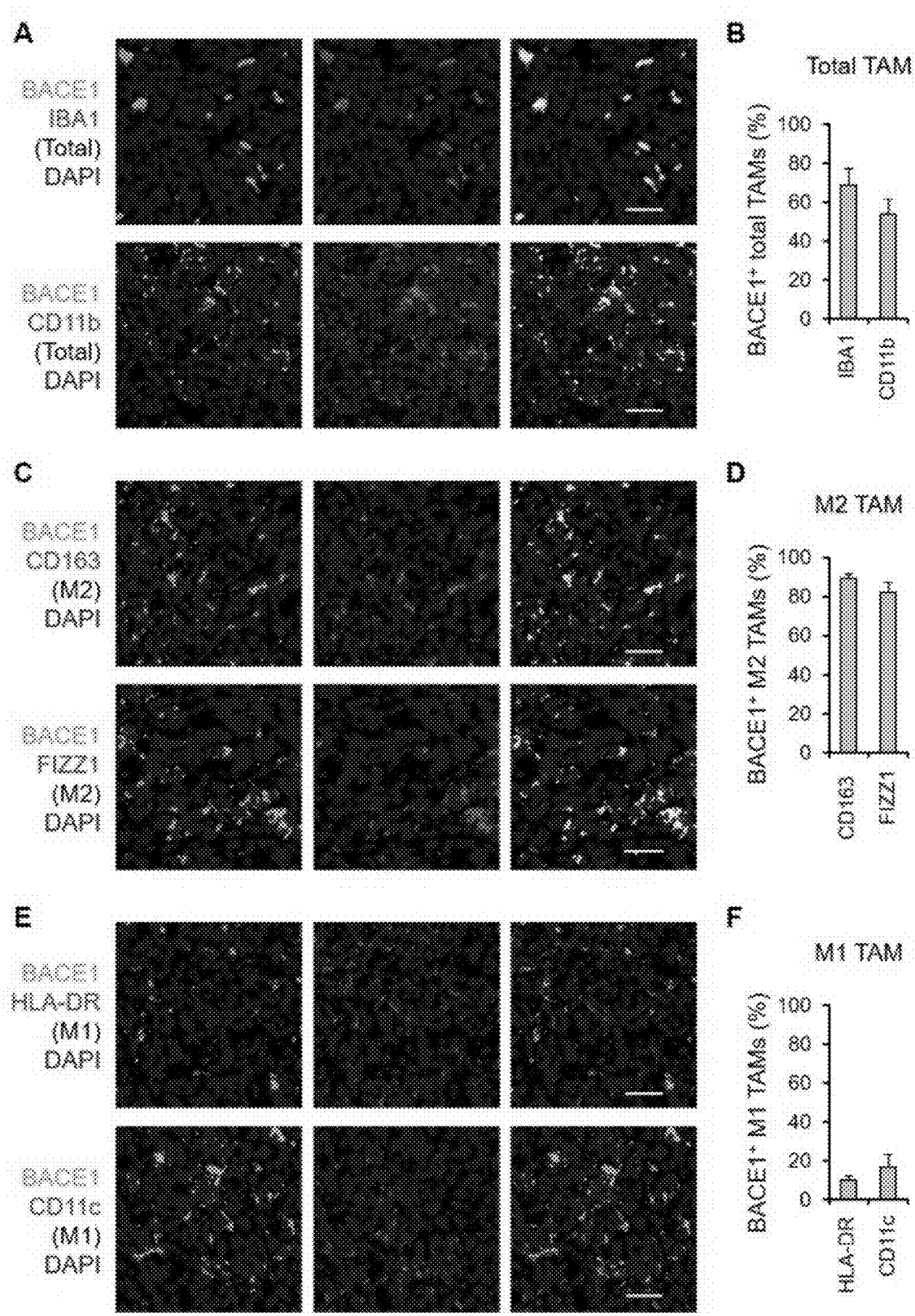

FIG. 11, panels A-F. BACE1 is Preferentially Expressed by M2 TAMs in GBM Xenografts. (A and B) Immunofluorescent analysis of BACE1 and the total TAM marker IBA1 or CD11b in GBM xenografts. Frozen sections of GBM xenografts derived from GSCs (T4121) were co-stained with specific antibodies against BACE1 (in green) and IBA1 or CD11b (in red) and then counterstained with DAPI (in blue). Representative immunofluorescent images (A) show the distribution and co-localization of BACE1 (in green) with the total TAM marker IBA1 or CD11b (in red) in the GBM xenografts. Quantification (B) shows the fractions of BACE1$^+$ TAMs (BACE1$^+$/IBA1$^+$ or BACE1$^+$/CD11b$^+$ cells) in total TAMs (IBA1$^+$ or CD11b$^+$ cells) in the GBM xenografts. (C and D) Immunofluorescent analysis of BACE1 and the M2 TAM markers CD163 or FIZZ1 in GBM xenografts. Frozen sections of GBM xenografts derived from GSCs (T4121) were co-stained with specific antibodies against BACE1 (in green) and CD163 or FIZZ1 (in red) and then counterstained with DAPI (in blue). Representative immunofluorescent images (C) show the distribution and co-localization of BACE1 (in green) with the M2 TAM marker CD163 or FIZZ1 (in red) in the GBM xenografts. Quantification (D) shows the fractions of BACE1+M2 TAMs (BACE1$^+$/CD163+ or BACE1$^+$/FIZZ1$^+$ cells) in M2 TAMs (CD163$^+$ or FIZZ1$^+$ cells) in the GBM xenografts. (E and F) Immunofluorescent analysis of BACE1 and the M1 TAM marker HLA-DR or CD11c in GBM xenografts. Frozen sections of GBM xenografts derived from GSCs (T4121) were co-stained with specific antibodies against BACE1 (in green) and HLA-DR or CD11c (in red) and then counterstained with DAPI (in blue). Representative immunofluorescent images (E) show the expression of BACE1 (in green) and M1 TAM markers (HLA-DR or CD11c, in red) in the GBM xenografts. Quantification (F) shows the fractions of BACE1$^+$ M1 TAMs (BACE1$^+$HLA-DR$^+$ or BACE1$^+$CD11c$^+$ cells) in M1 TAMs (HLA-DR$^+$ or CD11c$^+$ cells) in the GBM xenografts. Data are shown as mean±SEM. Scale bars represent 3 μM.

Figure 12:
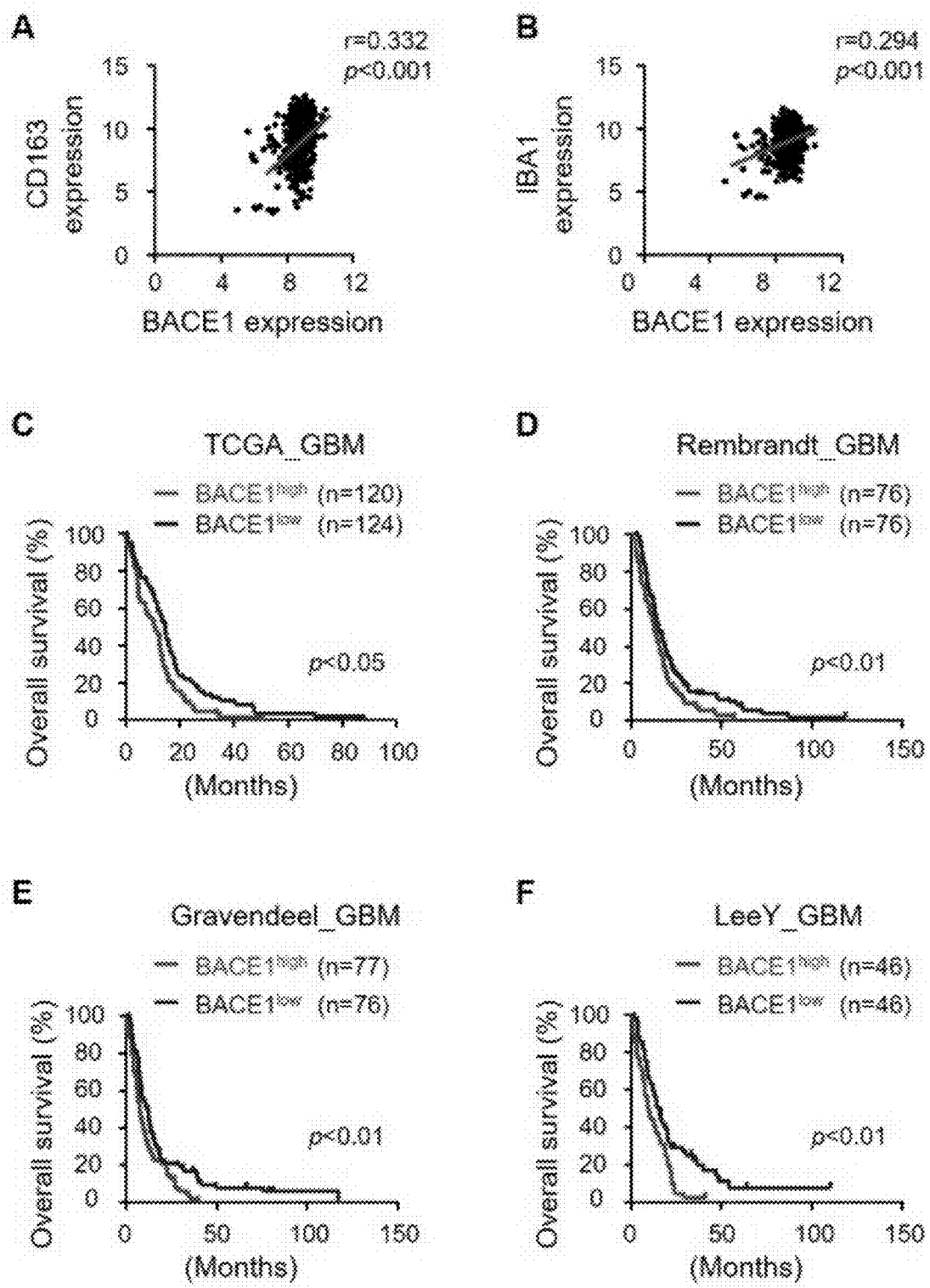

FIG. 12, panels A-F. BACE1 Expression Positively Correlates with CD163 and IBA1 Expression and Predicts A Poor Survival of GBM Patients. (A and B) Bivariate correlation analyses of expression levels between BACE1 and the M2 TAM marker CD163 (A; n=444, r=0.332, p<0.001) or the total TMA marker IBA1 (B; n=508, r=0.294, p<0.001) in GBM patients from the TCGA database. (C-F) Kaplan-Meier survival analyses showing an inverse correlation between BACE1 expression and overall survival of GBM patients in the databases of TCGA-GBM (C), Rembrandt (D), Gravendeel (E), and LeeY (F). Two-tailed log-rank test was used for analyses.

Figure 13:
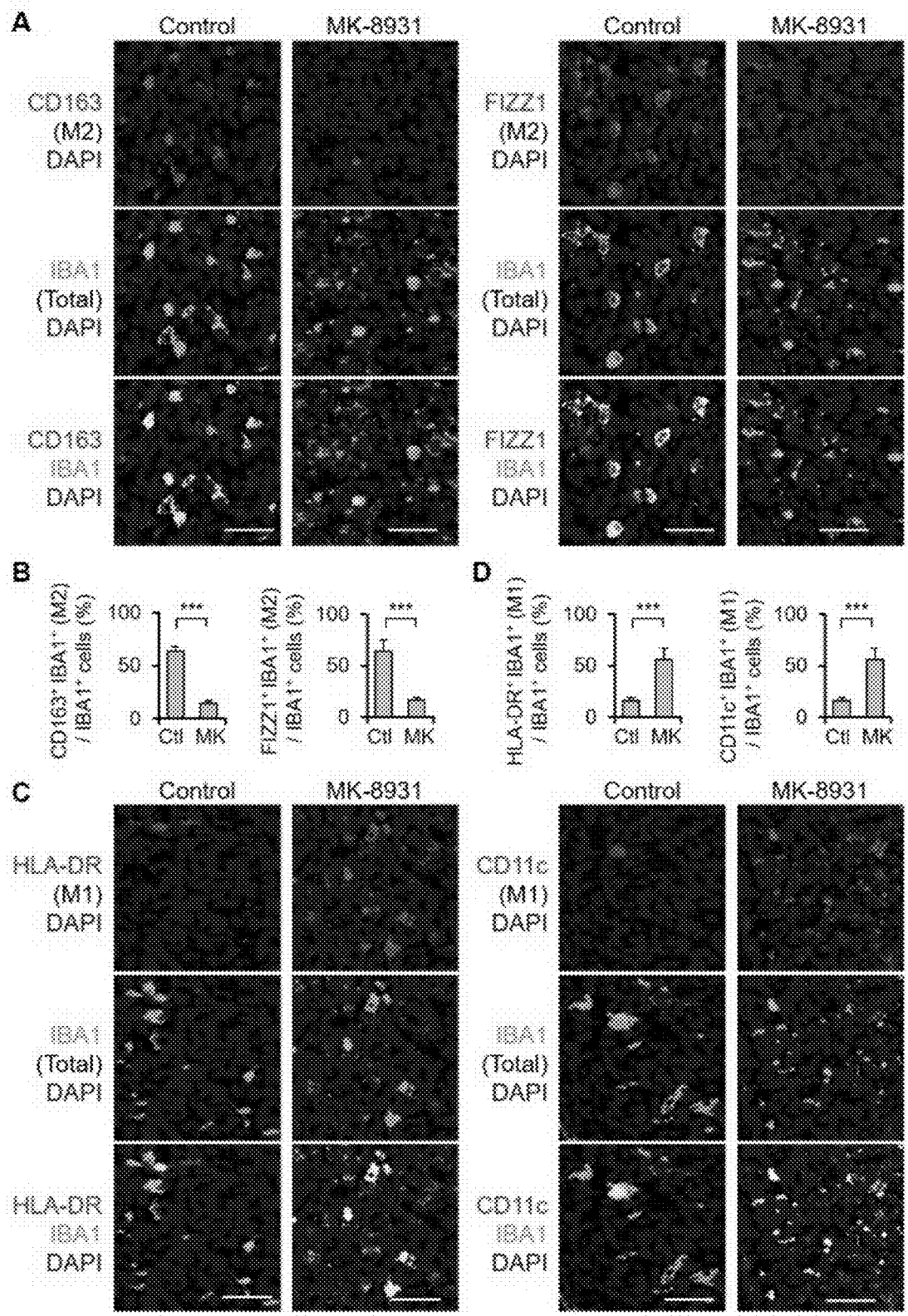

FIG. 13, panels A-C. BACE1 Inhibition by MK-8931 Converts M2 TAMs into M1 Macrophages in GBM Xenografts. (A and B) Density analysis of M2 TAMs by immunofluorescent staining of the M2 TAM marker (CD163 or FIZZ1) and the total TAM marker IBA1 and in GBM xenografts (T387) treated with MK-8931 or vehicle control. GBM xenografts were established by implantation of glioma stem cells (T387) through intracranial injection. Seven days after transplantation, the tumor-bearing mice were treated with MK-8931 (30 mg/kg) or the vehicle control once daily by oral gavage for two weeks. Frozen brain sections were immunostained with specific antibodies against CD163 or FIZZ1 (M2 TAM marker, in red) and IBA1 (in green) and counterstained with DAPI (in blue). Representative immunofluorescent images (A) showing M2 TAMs (CD163' or FIZZ1$^+$, in red) and total TAMs (IBA1$^+$, in green) in the MK-8931-treated or control GBM xenografts. Quantifications (B) showing that MK-8931 treatment significantly reduced density of M2 TAMs (CD163+/IBA1$^+$ or FIZZ1$^+$/IBA1$^+$) in GBM xenografts. * p<0.001. (C and D) Density analysis of M1 TAMs by immunofluorescent staining of the M TAM marker (HLA-DR or CD11c) and the total TAM marker IBA1 and in GBM xenografts (T387) treated with MK-8931 or vehicle control. Frozen brain sections were immunostained with specific antibodies against HLA-DR or CD11c (M TAM marker, in red) and IBA1 (in green) and counterstained with DAPI (in blue). Representative immunofluorescent images (C) showing M1 TAMs (HLA-DR$^+$ or CD11c$^+$, in red) and total TAMs (IBA1$^+$, in green) in the MK-8931-treated or control GBM xenografts. Quantifications (D) showing that MK-8931 treatment significantly increased density of M1 TAMs (HLA-DR$^+$/IBA1$^+$ or CD11c$^+$/IBA1$^+$) in GBM xenografts. *p<0.001. Data are shown as mean±SEM. ***p<0.001; Student's t-test. Scale bars represent 3 µM. Ctl: Control; MK: MK-8931.

Figure 14:
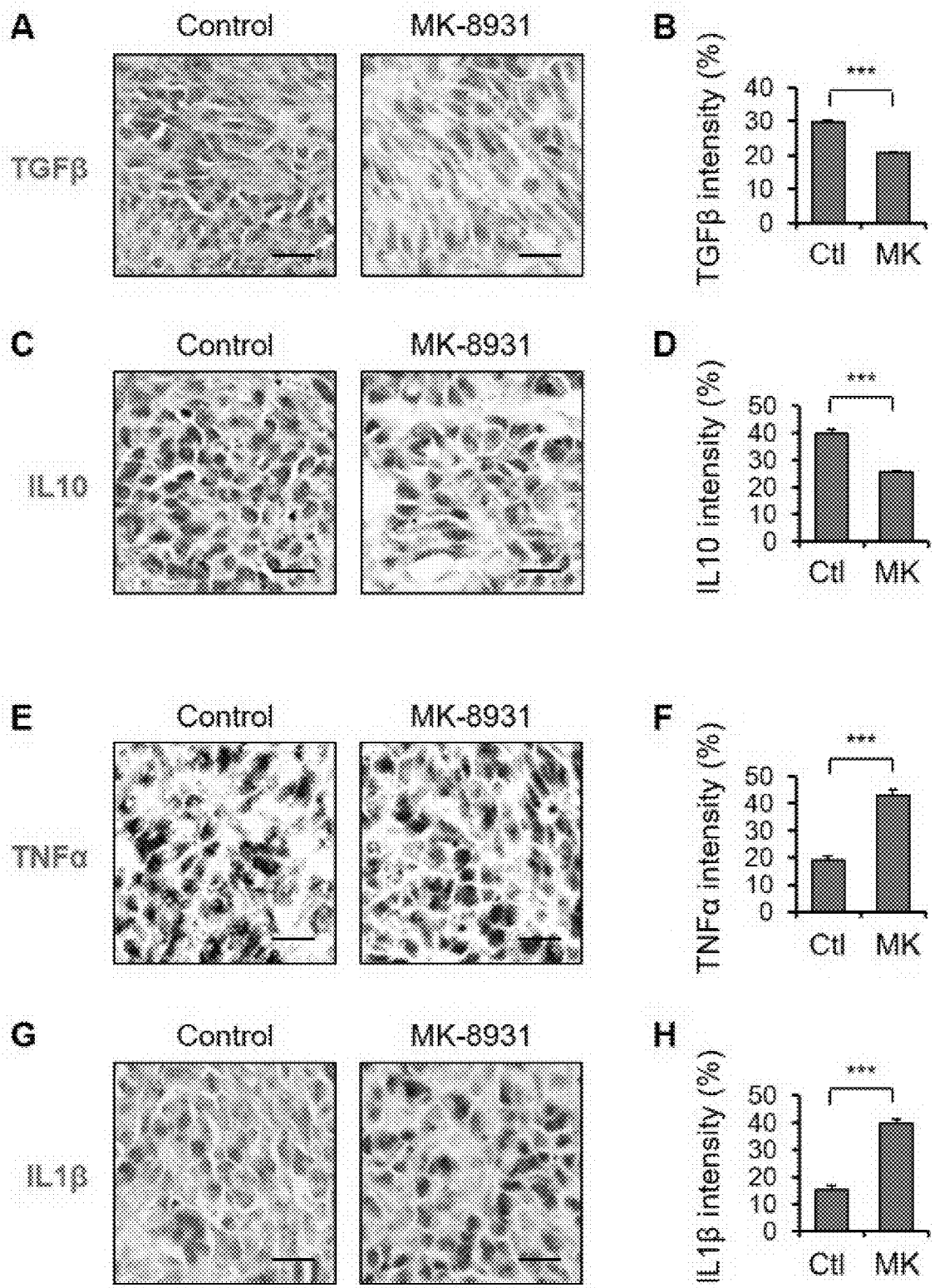

FIG. 14, panels A-H. BACE1 Inhibition by MK-8931 Altered Expression of TAM-Related Cytokines in GBM Xenografts. (A and B) Immunohistochemistry (IHC) analysis of TGF-β expression in the GBM xenografts treated with MK-8931 or the vehicle control. GBM xenografts were established by implantation of glioma stem cells (T4121) through intracranial injection. Seven days after transplantation, the tumor-bearing mice were treated with MK-8931 (30 mg/kg) or the vehicle control once daily by oral gavage for two weeks. Frozen xenograft sections were immunostained with a specific antibody against TGF-β (in brown) and counterstained with hematoxylin. Representative IHC images (A) showing TGF-β expression in the GBM xenograft treated with MK-8931 or the vehicle control. Quantification of TGF-β intensity (B) indicates that MK-8931 treatment significantly reduced TGF-β expression in GBM xenografts. * p<0.001. (C and D) Immunohistochemistry (IHC) analysis of IL10 expression in GBM xenografts treated with MK-8931 or the vehicle control. Frozen xenograft sections were immunostained with a specific antibody against IL10 (in brown) and counterstained with hematoxylin. Representative IHC images (C) shows IL10 expression in the GBM xenografts treated with MK-8931 or the vehicle control. Quantification of IL10 intensity (D) indicates that MK-8931 treatment significantly reduced IL10 expression in GBM xenografts. *p<0.001. (E and F) Immunohistochemistry (IHC) analysis of TNFα expression in GBM xenografts treated with MK-8931 or the vehicle control. Frozen xenograft sections were immunostained with a specific antibody against TNFα (in brown) and counterstained with hematoxylin. Representative IHC images (E) shows TNFα expression in the GBM xenografts treated with MK-8931 or the vehicle control. Quantification of TNFα intensity (F) indicates that MK-8931 treatment significantly induced TNFα expression in GBM xenografts. * p<0.001. (G and H) Immunohistochemistry (IHC) analysis of IL1β expression in GBM xenografts treated with MK-8931 or the vehicle control. Frozen xenograft sections were immunostained with a specific antibody against IL1β (in brown) and counterstained with hematoxylin. Representative IHC images (G) shows IL1β expression in the GBM xenografts treated with MK-8931 or the vehicle control. Quantification of IL1β intensity (H) indicates that MK-8931 treatment significantly induced IL1β expression in GBM xenografts. *p<0.001. Data are shown as mean±SEM. *** p<0.001, student's t-test. Scale bar represents 30 µM. Ctl: Control; MK: MK-8931.

Figure 15:
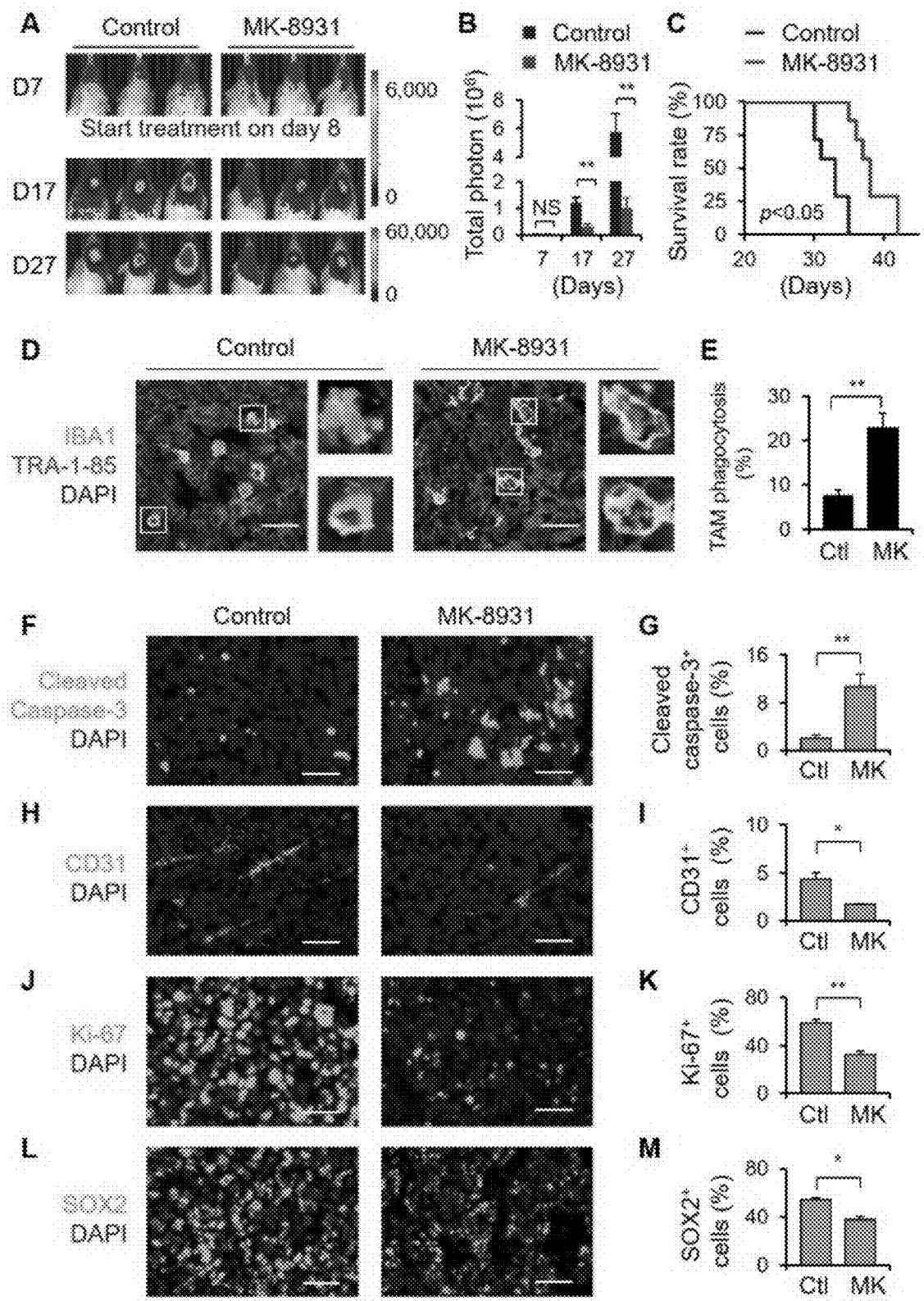

FIG. 15, panels A-M. Targeting BACE1 by MK-8931 Suppressed GBM Tumor Growth and Extended Survival of the Tumor-bearing animals. (A-C) A preclinical trial of MK-8931 for GBM treatment in GSC-derived xenograft models. Human glioma stem cells (T387) expressing luciferase were transplanted into mouse brains through intracranial injection to establish orthotopic GBM xenografts. One week after the transplantation, the tumor-bearing mice were treated with MK-8931 (30 mg/kg) or the vehicle control once daily by oral gavage until the appearance of humane endpoints. In vivo bioluminescent imaging (IVIS) were performed twice per week to monitor tumor growth. When humane endpoints occur, mouse was anesthetized and brain bearing tumor was harvested. Representative bioluminescent images (A) of intracranial GBM xenografts treated with MK-8931 or the vehicle control on day 7 (before treatment), day 17 and day 27 (treatment for 10 and 20 days) are shown. Quantification (B) shows the mean bioluminescence of GBM xenografts treated with MK-8931 or the vehicle control on day 7 (before treatment), day 17 and day 27 (treatment for 10 and 20 days). Kaplan-Meier survival curves indicate that MK-8931 treatment significantly extended the survival of animals bearing the GBM xenografts. p<0.05. Log-rank analysis was used to assess the significance. (D and E) In vivo phagocytosis of TAMs against human glioma cells in GBM xenografts treated with MK-8931 or the vehicle control. Frozen xenograft sections were immunostained with specific antibodies against IBA1 (in green, detecting TAMs) and the human cell antigen TRA-1-85 (in red, detecting glioma cells) and counterstained with DAPI (in blue). Representative images (D) showing in vivo TAM phagocytosis as the inclusion body of a glioma cell (TRA-1-85+, in red) within a TAM (IBA1$^+$, in green) in the MK-8931 treated GBM xenografts but not in the control tumors. Quantification (E) showing that MK-9831 treatment significantly increased the inclusion bodies of glioma cells (TRA-1-85+, in red) within TAMs (IBA1$^+$, in green) in GBM xenografts, indicating that MK-8931 treatment promoted TAM phagocytosis.  p<0.01. (F and G) Detection of apoptosis by immunofluorescent staining of cleaved caspase-3 the GSC-derived xenografts treated with MK-8931 or the vehicle control. Frozen xenograft sections were immunostained with a specific antibody against cleaved caspase-3 (in green) and counterstained with DAPI (in blue). Representative immunofluorescent images of cleaved caspase-3 (F) in the GBM xenografts treated with MK-8931 or the vehicle control were shown. Quantification (G) shows that MK-8931 treatment significantly increased apoptosis (cleaved caspase-3+ cells) in the GBM xenografts relative to the control tumors.  p<0.01. (H and I) Vessel density analysis by immunofluorescent staining of CD31 in the GSC-derived xenografts treated with MK-8931 or the vehicle control. Frozen sections were immunostained with a specific antibody against CD31 (in green) and counterstained with DAPI (in blue). Representative immunofluorescent images of CD31 (H) in the GBM xenografts treated with MK-8931 or the vehicle control were shown. Quantification (I) shows that MK-8931 treatment significantly reduced vessel density (CD31V cells) in the GBM xenografts. * p<0.05. (J and K) Cell proliferation analysis by immunofluorescent staining of Ki-67 in the GSC-derived xenografts treated with MK-8931 or the vehicle control. Frozen sections were immunostained with a specific antibody against Ki-67 (in green) and counterstained with DAPI (in blue). Representative immunofluorescent images of Ki-67 (J) in the GBM xenografts treated with MK-8931 or the vehicle control were shown. Quantification (K) shows that Mk-8931 treatment significantly reduced proliferative cells (Ki-67+) in the GBM xenografts. ** p<0.01. (L and M) GSC population analysis by immunofluorescent staining of SOX2 in the GSC-derived xenografts treated with MK-8931 or the vehicle control. Frozen sections were immunostained with a specific antibody against the GSC marker SOX2 (in green) and counterstained with DAPI (in blue). Representative immunofluorescent images of SOX2 (L) in the GBM xenografts treated with MK-8931 or the vehicle control were shown. Quantification (M) shows that MK-8931 treatment significant reduced GSCs (SOX2+ cells) in the GBM xenografts. * p<0.05. Data are shown as mean±SEM. * p<0.05 and ** p<0.01; Student's t-test. Scale bar represents 30 µM. Ctl: Control; MK: MK-8931.

Figure 16:
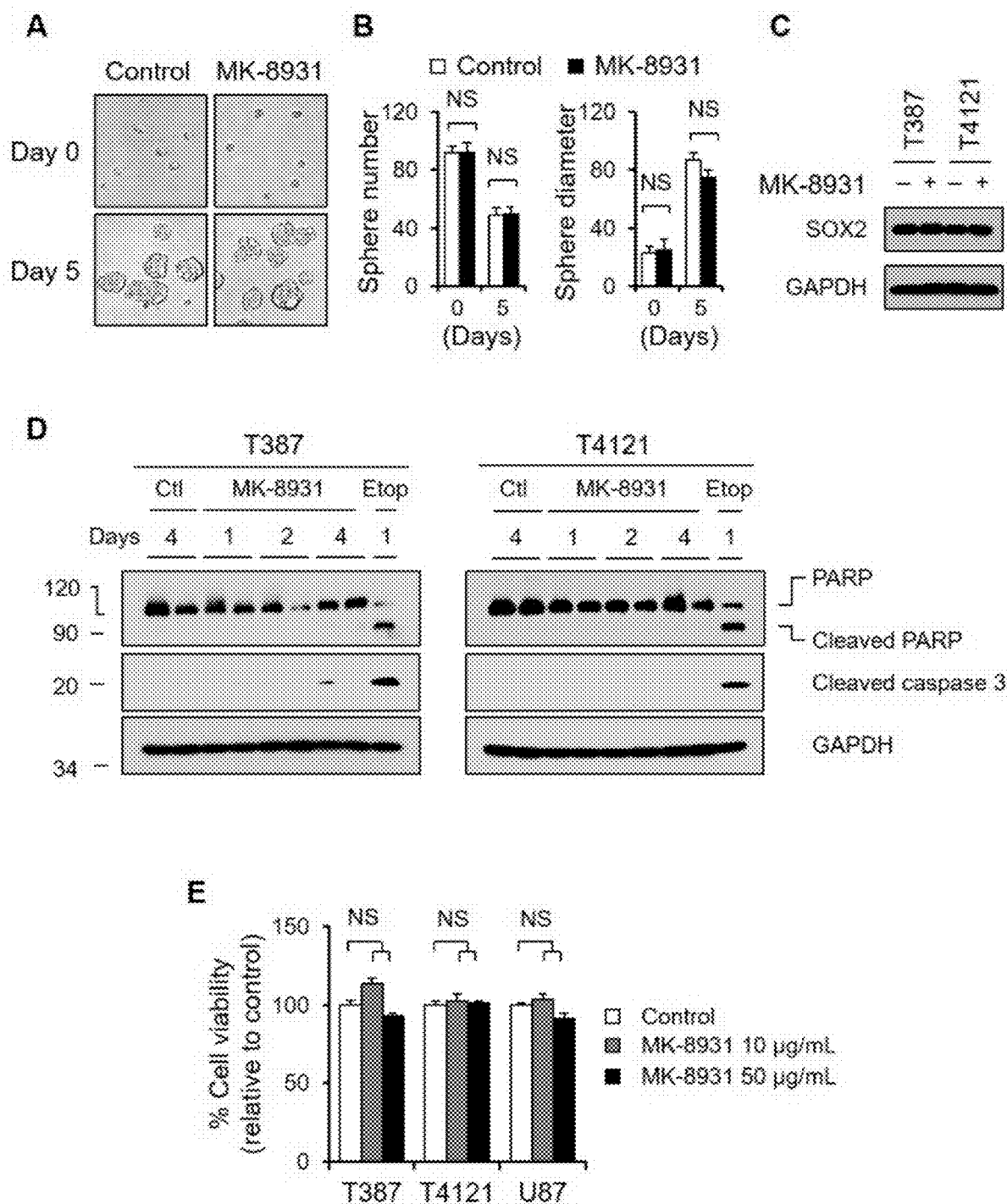

FIG. 16, panels A-E. MK-8931 Treatment Had Little Effect on Glioma Stem Cells. (A and B) Tumorsphere formation assay to examine the effect of MK-8931 treatment on glioma stem cells (GSCs). Representative images (A) of tumorsphere derived from T4121 GSCs treated with MK-8931 (50 µg/mL) or the vehicle control. Quantifications (B) show the number and size of tumorsphere derived from T4121 GSCs treated with MK-8931 (50 µg/mL) or the control. Data are shown as mean±SEM. NS (not significant) ≥0.05, Student's t-test. (C) Immunoblot analysis of SOX2 expression in GSCs (T4121 and T387) treated with MK-8931 (50 µg/mL) or the vehicle control for three days. GAPDH was blotted as loading control. (D) Immunoblot analysis of the apoptotic markers cleaved-PARP and cleaved caspase-3 in GSCs (T387 and T4121) treated with MK-8931 (50 µg/mL), etoposide (Etop, 1 µM), or the vehicle control for different time as indicated. GAPDH was blotted as loading control. MK-8931 treatment did not induce apoptosis in GSCs in vitro. Ctl: Control; Etop: Etoposide. (E) Cell viability assay to examine the effect of MK-8931 treatment on proliferation of glioma stem cells. GSCs (T387, T4121, and U87) were treated with MK-8931 (10 and 50 µg/mL) or the vehicle control for three days, and cell numbers were determined by cell titer assay. Data are shown as mean±SEM. NS (not significant)≥0.05, Student's t-test.

Figure 17:
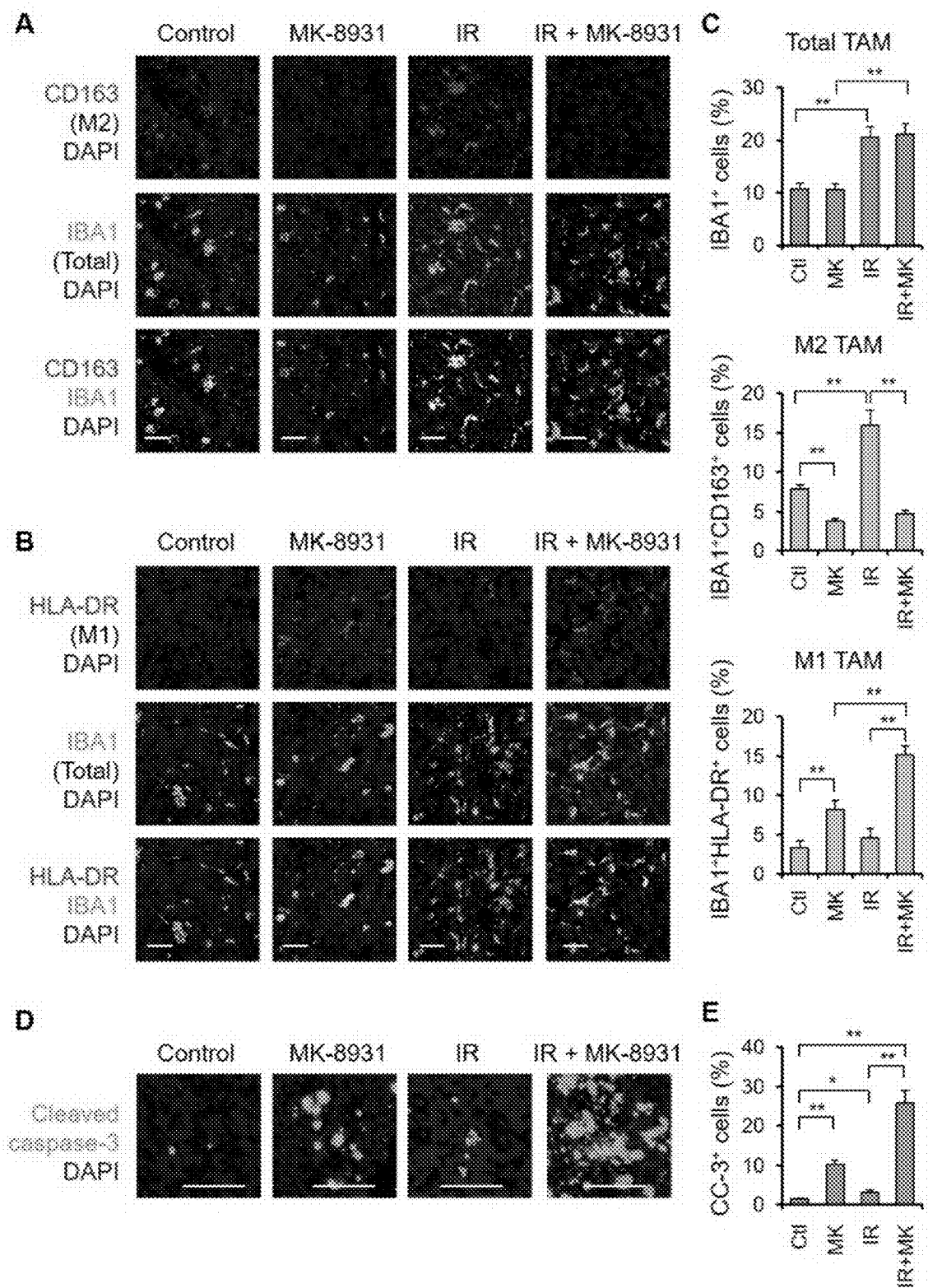

FIG. 17, panels A-E. Effects of MK-8931 Treatment in Combination with Low Dose of Irritation on TAM Polarization and Tumor Cell Apoptosis in GBM Xenografts. (A-C) Density analysis of M2 TAMs (A) or M1 TAMs (B) by double immunofluorescent staining of the total TAM marker IBA1 (in green) and the M2 TAM marker CD163 (in red) or the M1 TAM marker HLA-DR (in red) in the GSC-derived GBM xenografts treated with MK-8931, IR (2 Gy), IR plus MK-8931, or the vehicle control. Frozen xenograft sections were co-immunostained with specific antibodies against IBA1 (in green) and CD163 (in red) or HLA-DR (in red) and counterstained with DAPI (in blue). Representative immunofluorescent images showing the staining of IBA1 and the M2 TAM marker CD163 (A) or IBA1 and the M1 TAM marker HLA-DR (B) in the GBM xenografts. Quantifications (C) show the fractions of total TAMs (IBA1+ cells), M2 TAMs (IBA1+/CD163+ cells), and M1 TAMs (IBA1+/HLA-DR+ cells) in the GBM xenografts from the four groups (Control, MK-8931, IR, and IR+MK-8931). * p<0.05 and ** p<0.01. (D and E). In vivo apoptosis analysis by immunofluorescent staining of cleaved caspase-3 in the GBM xenografts treated with MK-8931, IR (2×2 Gy), IR plus MK-8931, or the vehicle control. Frozen xenografts sections were immunostained with a specific antibody against cleaved caspase-3 (in green) and counterstained with DAPI (in blue). Representative immunofluorescent images (D) showing the levels of cleaved caspase-3 in the GBM xenografts from four groups (Control, MK-8931, IR, and IR+MK-8931). Quantification (E) shows the fraction of cleaved caspase-3+ (CC-3+) cells in the GBM xenografts from the four treatment groups. * p<0.05 and ** p<0.01. Data are shown as mean±SEM from at least 5 images of 3-5 mice. * p<0.05 and ** p<0.01; Student's t-test. Scale bar represents 3 µM. Ctl: Control; IR: Irradiation; CC-3: Cleaved caspase-3.

Figure 18:
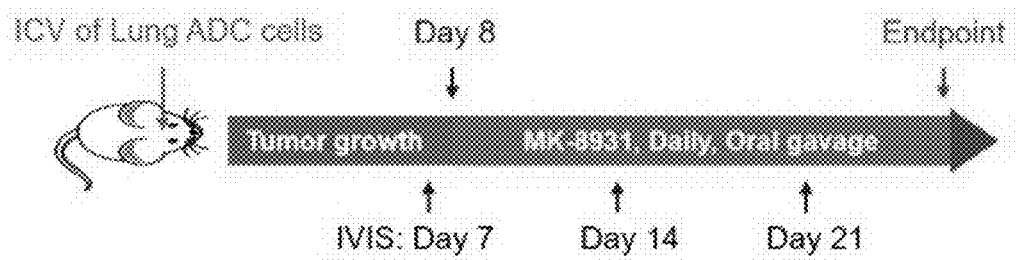
Figure 18:
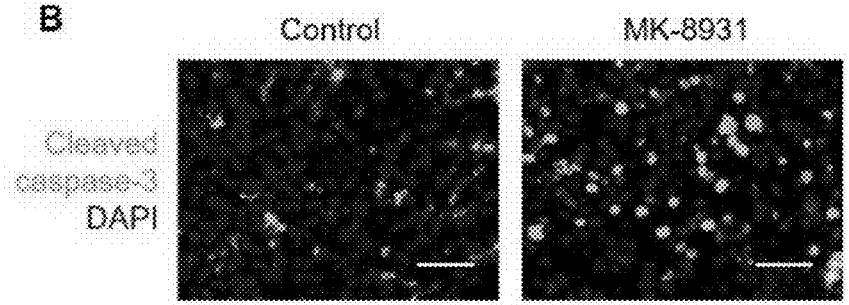
Figure 18:
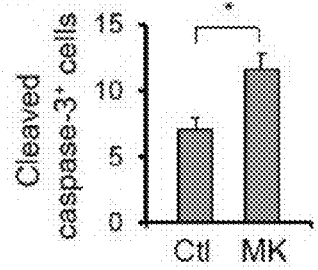
Figure 18:
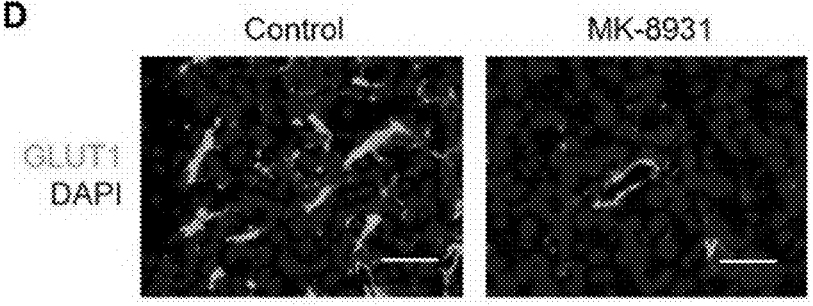
Figure 18:
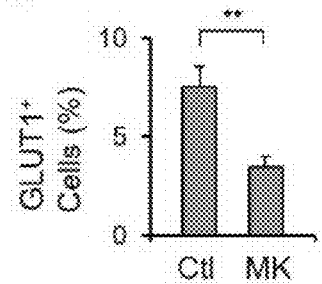
Figure 18:
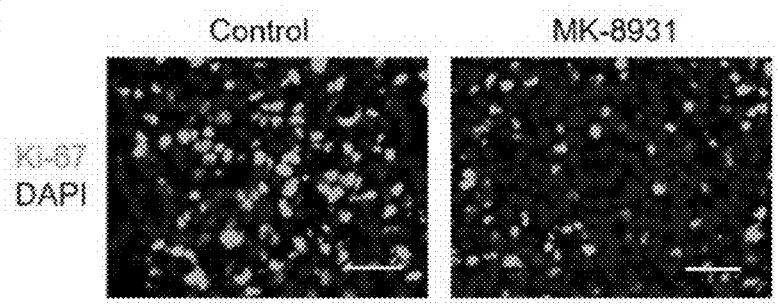
Figure 18:
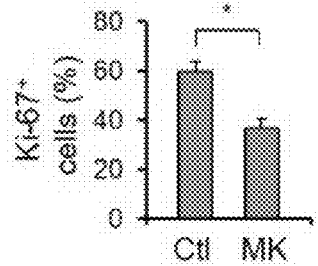

FIG. 18, panels A-G. MK-8931 Treatment Resulted in Increased Apoptosis, Reduced Vessel Density and Decreased Cell Proliferation in Brain Metastases of Lung ADC. (A) A schedule showing the MK-8931 treatment for brain metastases of lung adenocarcinoma (ADC) in xenograft models. The lung ADC cancer cells (H1002) expressing luciferase were transplanted into mouse brains to establish intracranial xenografts of lung ADC. One week after the transplantation, the tumor-bearing mice were treated with MK-8931 (30 mg/kg) or the vehicle control once daily by oral gavage until the appearance of humane endpoints. IVIS was performed twice per week to monitor tumor growth. When humane endpoints occur, mouse was anesthetized and brains with xenografts were harvested for further analyses. (B and C) In vivo apoptosis analysis by immunofluorescent staining of cleaved caspase-3 in the MK-8931-treated or control intracranial xenografts of lung ADC (H1002). Frozen xenograft sections were immunostained with a specific antibody against cleaved caspase-3 (in green) and counterstained with DAPI (in blue). Representative immunofluorescent images (B) showing the levels of cleaved caspase-3 in the xenografts treated with MK-8931 or the vehicle control. Quantification (C) shows the fraction of cleaved caspase-3+ cells in the intracranial xenografts of lung ADC. MK-8931 treatment significantly augmented apoptosis in intracranial xenografts of lung ADC. * p<0.05. (D and E) In vivo vessel density analysis by immunofluorescent staining of GLUT1 in the MK-8931-treated or control intracranial xenografts of lung ADC (H1002). Frozen xenograft sections were immunostained with a specific antibody against cleaved GLUT1 (in green) and counterstained with DAPI (in blue). Representative immunofluorescent images (D) showing the vessel density (GLUT1+ cells) in the xenografts treated with MK-8931 or the vehicle control. Quantification (E) shows vessel density (GLUT1 cells) in the intracranial xenografts of lung ADC. MK-8931 treatment significantly reduced vessel density in intracranial xenografts of lung ADC. * p<0.05. (F and G) In vivo proliferation analysis by immunofluorescent staining of Ki-67 in the MK-8931-treated or control intracranial xenografts of lung ADC (H1002). Frozen xenograft sections were immunostained with a specific antibody against Ki-67 (in green) and counterstained with DAPI (in blue). Representative immunofluorescent images (F) showing the expression of Ki-67 in the xenografts treated with MK-8931 or the vehicle control. Quantification (G) shows the fraction of Ki-67$^+$ cells in the intracranial xenografts of lung ADC. MK-8931 treatment significantly reduced cell proliferation in intracranial xenografts of lung ADC. ** p<0.01. Data are shown as mean±SEM of at least 6 images from 3-5 mice. * p<0.05 and ** p<0.01; Student's t-test. Scale bar represents 3 μM. Ctl: Control; MK: MK-8931.

Figure 19:
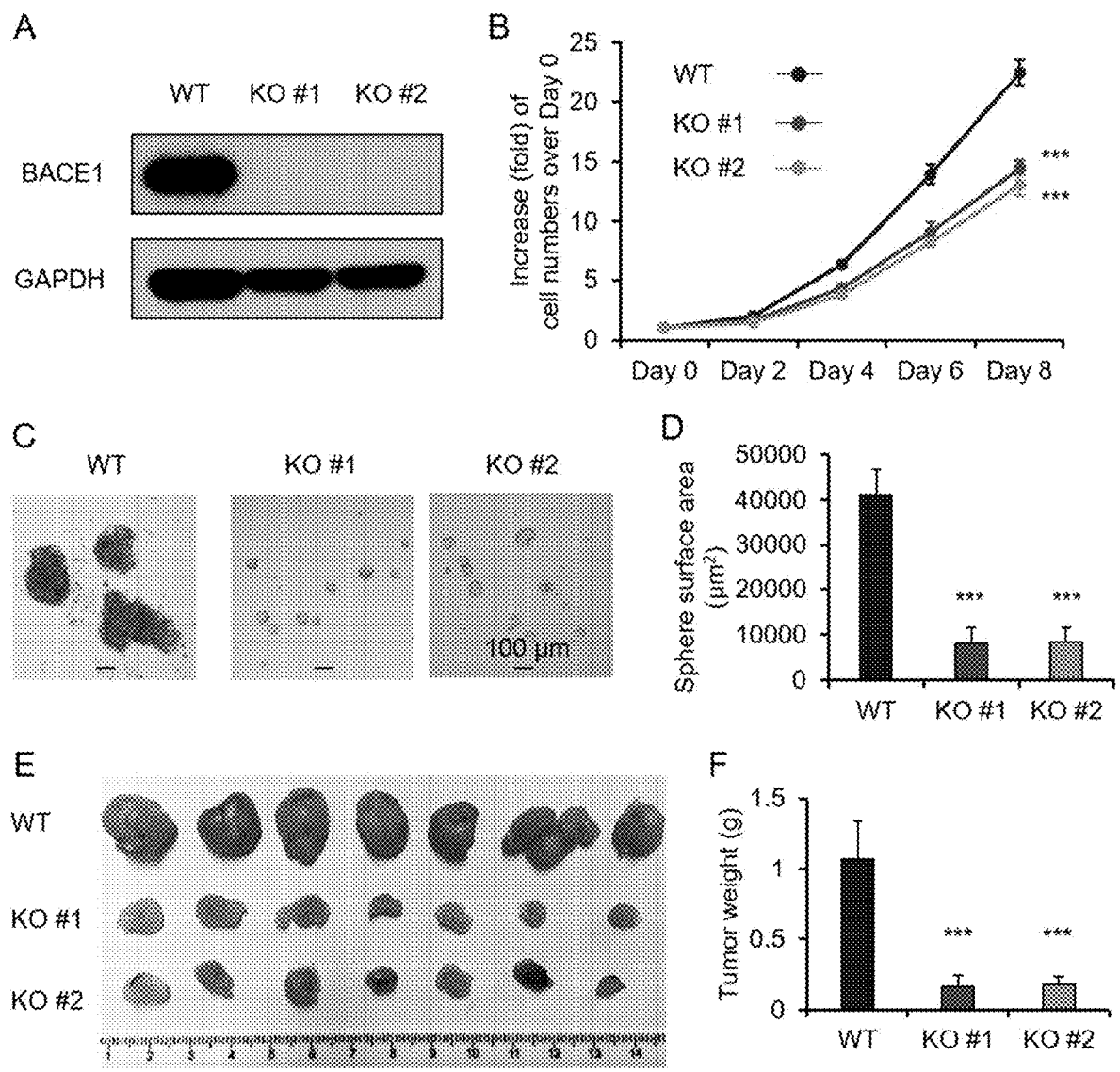

FIG. 19, panels A-F, show disrupting BACE1 inhibited lung cancer growth. (A) Immunoblot analysis of BACE1 in the wild type (WT) and BACE1 knockout (KO) lung cancer cells. H1002 lung cancer cells derived from the brain metastases of lung adenocarcinoma were infected with lentivirus expressing scramble sgRNA (WT) or sgRNAs targeting BACE1. After selection, the expression of BACE1 in WT or KO lung cancer cells were confirmed by western blots. Representative images showing that BACE1 was successfully knocked out in the H1002 lung cancer cells. (B) Cell viability assay to examine the effect of BACE1 deletion on lung cancer cell proliferation. One thousand WT or KO H1002 cells were seeded as monolayers to grow, and the cell numbers were determined by cell titer assay at day 0, 2, 4, 6, and 8. Data are shown as means±SEM. p *<0.001 vs WT. (C and D) Tumorsphere formation assay to examine the role of BACE1 in maintaining self-renewal potential of lung cancer cells. Representative images (C) of tumorsphere derived from WT or BACE1-KO H1002 lung cancer cells. Quantifications (D) show the sizes (surface area) of WT or BACE1-KO tumorspheres. Data are shown as mean±SEM. p *<0.001 vs WT, Student's t-test. (E and F) BACE1 deletion (knockout) inhibited lung cancer growth in subcutaneous xenograft model. Brief, WT or BACE1-KO lung cancer cells (106) were subcutaneously injected into right flank of NSG mice. Tumors dissected from mice of each group were plotted (E) and weighed (F). BACE1 deletion markedly inhibited tumor growth of lung cancers. Data are shown as mean±SEM. p ***<0.001 vs WT, Student's t-test.

Figure 20:
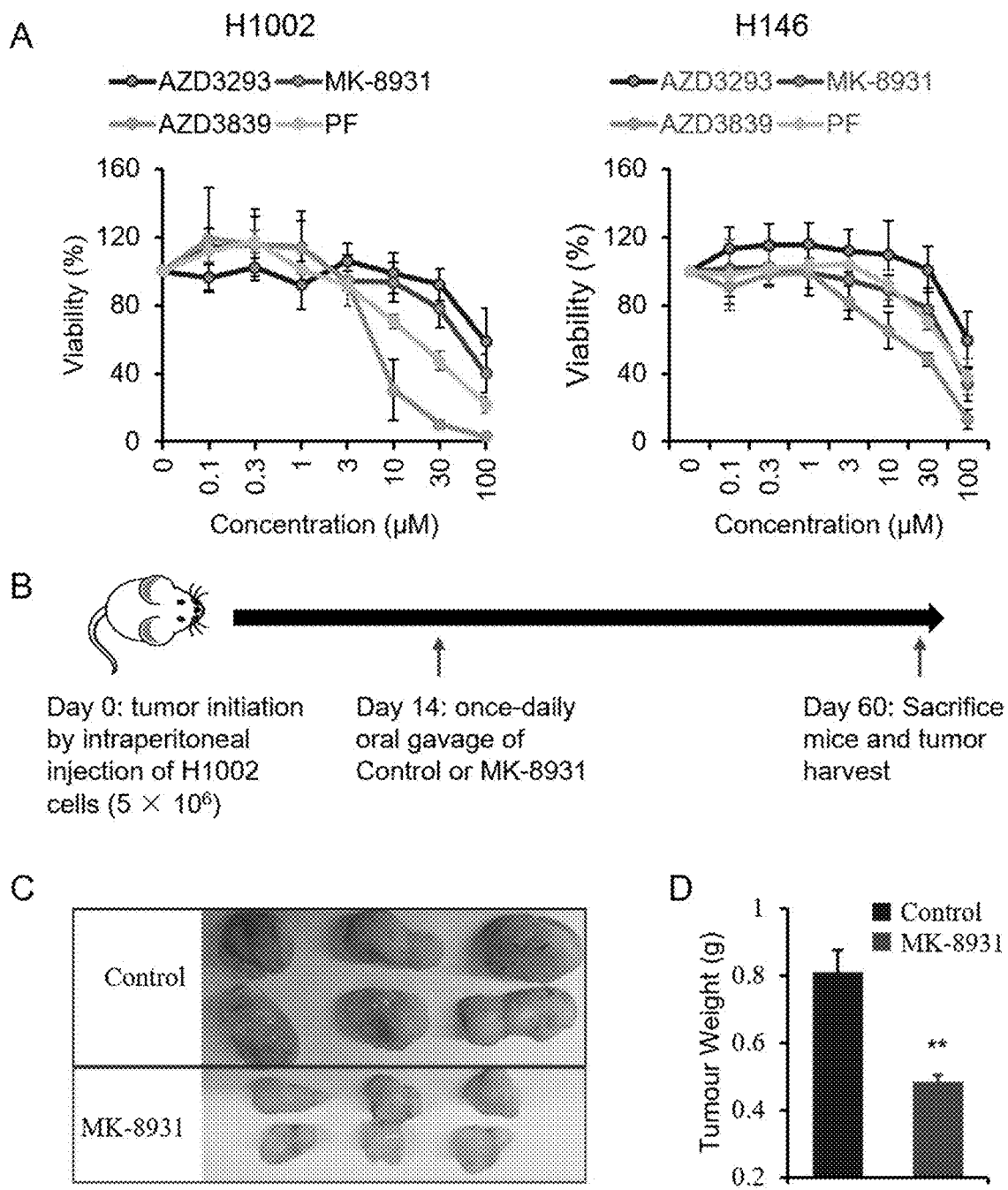

FIG. 20, panels A-D, show BACE1 inhibitors suppressed lung cancer cell proliferation and inhibited tumor growth of lung cancer cells. (A) Effects of BACE1 inhibitors on lung cancer cell proliferation. H1002 and H146 lung cancer cells were treated with the indicated concentrations of the BACE1 inhibitor AZD3293, MK-8931, AZD3839, or PF-06751979 (PF) for 72 hours. Cell viability was assessed by cell titer assay (n=3). (B-D) A preclinical trial of MK-8931 for lung cancer treatment in xenograft models. H1002 lung cancer cells (5×106) were transplanted into mouse right flank through subcutaneous injection to establish subcutaneous lung cancer xenografts. Two weeks after inoculation, the tumor-bearing mice were treated with MK-8931 (50 mg/kg) or the vehicle control once daily by oral gavage until experimental endpoints (B). Tumors dissected from mice of each group were photographed (C) and weighed (D). Treatment with MK-8931 markedly inhibited lung tumor growth. Data are shown as mean SEM. p **<0.01, Student's t-test.

Figure 21:
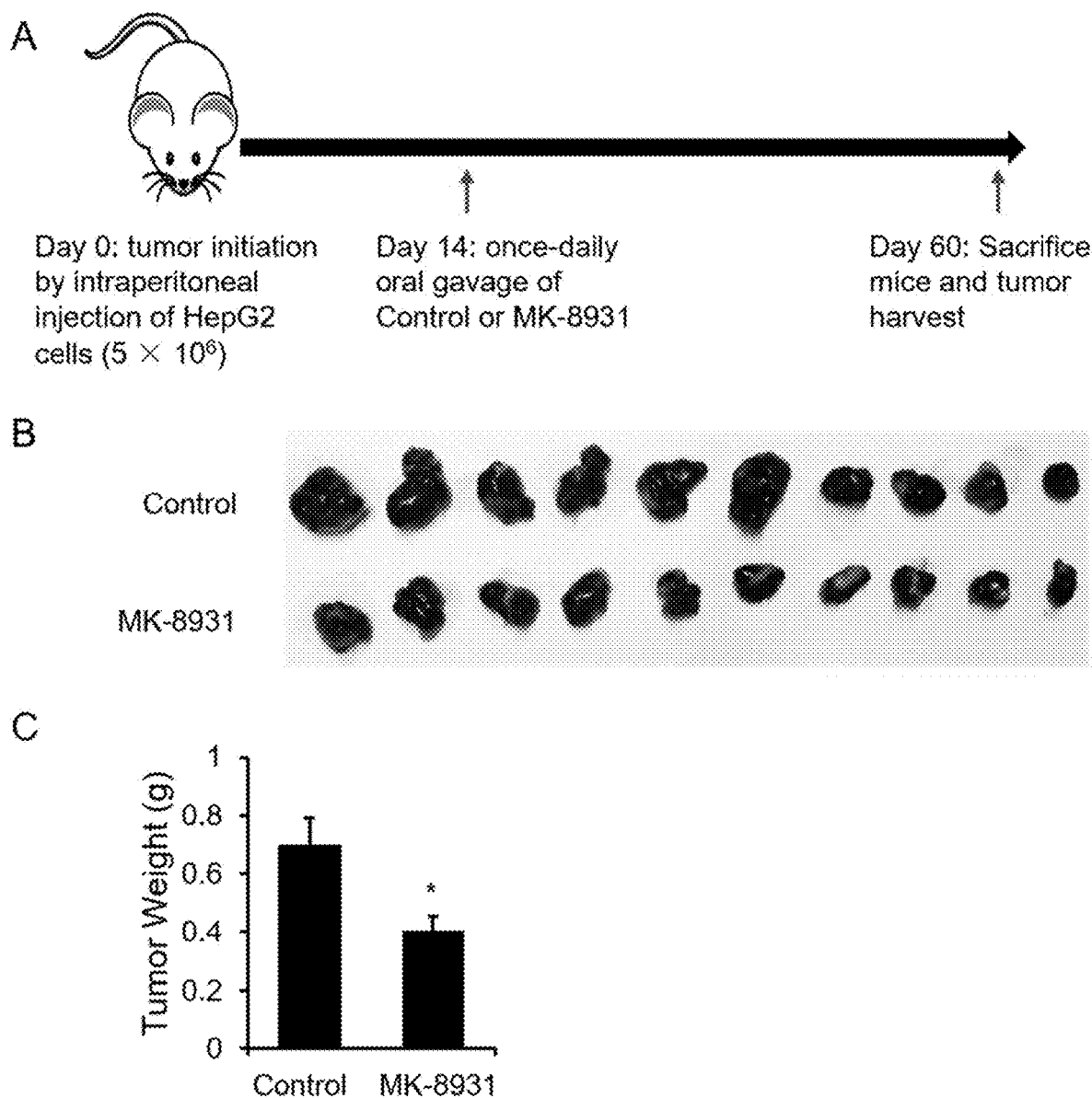

FIG. 21, panels A-C, show that the BACE1 inhibitor MK-8931 inhibited liver tumor growth. (A-C) A preclinical trial of MK-8931 for liver cancer treatment xenograft models. HepG2 liver cancer cells (5×106) were transplanted into mouse right flank through subcutaneous injection to establish subcutaneous liver cancer xenografts. Two weeks after inoculation, the tumor-bearing mice were treated with MK-8931 (50 mg/kg) or the vehicle control once daily by oral gavage until experimental endpoints (A). Tumors dissected from mice of each group were photographed (B) and weighed (C). Treatment with MK-8931 significantly inhibited liver tumor growth. Data are shown as mean±SEM. p *<0.05, Student's t-test.

Figure 22:
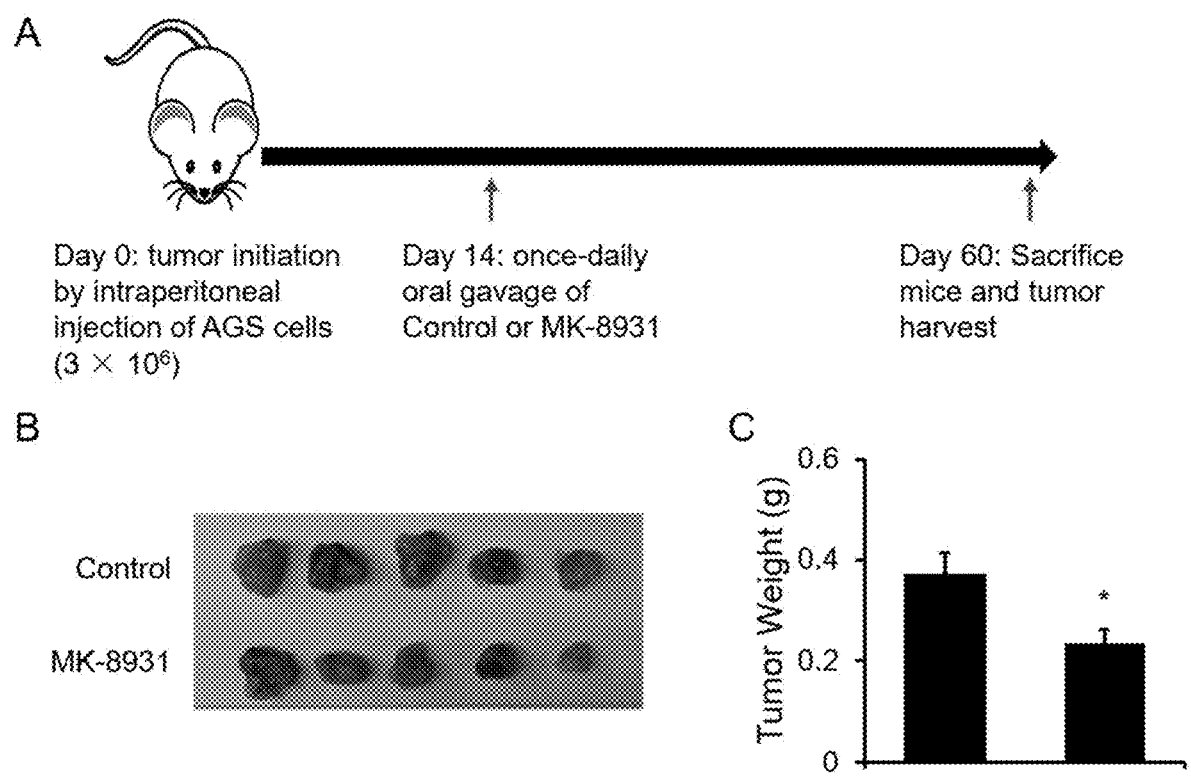

FIG. 22, panels A-C, show treatment with the BACE1 Inhibitor MK-8931 reduced tumor growth of gastric cancer. (A-C) A preclinical trial of MK-8931 for stomach cancer treatment in xenograft models. AGS gastric cancer cells (3×106) were transplanted into mouse right flank through subcutaneous injection to establish subcutaneous stomach cancer xenografts. Two weeks after inoculation, the tumor-bearing mice were treated with MK-8931 (50 mg/kg) or the vehicle control once daily by oral gavage until experimental endpoints (A). Tumors dissected from mice of each group were photographed (B) and weighed (C). Treatment with MK-8931 significantly reduced tumor growth of gastric cancer. Data are shown as mean±SEM. p *<0.05, Student's t-test.

DETAILED DESCRIPTION

Provided herein are compositions, systems, kits, and methods for treating a subject with cancer by administering a BACE1 inhibitor, such as MK-8931. In particular embodiments, the subject is treated with radiation (e.g., low dose radiation or regular dose radiation) first, and then administered a BACE1 inhibitor within a certain time window (e.g., about 3 hours to 6 days after the radiation treatment).

Macrophages derived from monocytes are highly plastic immune cells that can be polarized into M1 or M2 macrophages in response to various stimulations (Murray, 2017). M1 macrophages marked by expression of the major histocompatibility complex (MHC) II, inducible nitric oxide synthase (iNOS), and CD11c (Colegio et al., 2014; Deininger et al., 2000; Shi et al., 2017a; Zhou et al., 2015) display potent phagocytosis activity that can eliminate tumor cells via nitric oxide (NO) and TNF-α (Sica et al., 2008). In contrast, M2 macrophages expressing markers including CD163, arginase-1 (ARG1), and FIZZ1 (Colegio et al., 2014; Deininger et al., 2000; Komohara et al., 2008; Shi et al., 2017a; Zhou et al., 2015) can be promoted by Th2 cytokines including IL4, IL10, and IL13 or other factors secreted by cancer cells (Sica et al., 2008). The majority of TAMs in TME has been demonstrated to more closely resemble M2-polarized macrophages that suppress anti-tumor immune response and support malignant progression (Sica et al., 2008; Zhou and Bao, 2014a). Thus, while the present invention is not limited to any particular mechanism, and an understanding of the mechanism is not necessary to practice the invention, it is believed that therapeutics that can redirect M2 TAMs to M1 macrophages will not only mitigate the immune suppressive microenvironment but also promote the anti-tumor innate response to inhibit malignant growth. In order to develop effective therapeutics activating TAM phagocytosis to attack cancer cells, it is important to understand the molecular mechanisms underlying the polarization of M1 and M2 TAMs and identify molecular modulators that can reprogram M2 TAMs into M1 macrophages. In work conducted during development of embodiments herein, we used human iPS cell-derived macrophages to screen for small molecules that can promote macrophage phagocytosis against cancer cells. To this end, we identified MK-8931 as one of top drug candidates and thus determined its molecular target BACE1 (the 3-site amyloid precursor protein cleaving enzyme 1) as an important modulator in regulating the phenotype switch of M2/M1 macrophages. It was found that BACE1 inhibition by MK-8931 potently redirects M2 TAMs into M1 macrophages and promotes macrophage phagocytosis to suppress malignant growth of GBMs and brain metastases of lung ADC.

BACE1 is a transmembrane aspartyl protease that is responsible for the production of amyloid beta peptide (A) in brains of patients with Alzheimer's disease (AD) (Hussain et al., 1999; Sinha et al., 1999; Vassar et al., 1999; Yan et al., 1999). Since its discovery, BACE1 has been widely investigated as a therapeutic target for AD (Yan and Vassar, 2014b), and several BACE1 inhibitors have been developed and used in clinical trials for AD treatment (Panza et al., 2018; Yan and Vassar, 2014a). In work conducted during the development of embodiments herein, it was found that BACE1 is preferentially expressed by M2 TAMs and that the BACE1-mediated STAT3 activation is required for the polarization and maintenance of M2 TAMs. Functional inhibition of BACE1 by a specific inhibitor, MK-8931, effectively converted M2 TAMs into M1 macrophages to promote TAM phagocytosis against tumor cells. Importantly, as described in the Example below, it was demonstrated that BACE1 inhibition by MK-8931 treatment also suppressed tumor growth of brain metastases of lung ADC, indicating that pharmacological targeting of BACE1 can be used to reclaim the anti-tumor activity of TAMs for multiple malignant tumors containing the TAMs. Furthermore, it was demonstrated that low dose of radiation markedly enhanced infiltration of TMAs and synergized with MK-8931 treatment to suppress tumor growth. Thus, in certain embodiments, one could use radiation (e.g., low dose radiation) to induce infiltration of M2 TAMs into those tumors containing relatively less TAMs and then treat tumors with a BACE1 inhibitor (e.g., MK-8931) to activate TAM phagocytosis to improve the anti-tumor efficacy.

MK-8931, also known as Verubecestat, is a non-peptidic class of BACE1 inhibitor developed for potential AD treatment through fragment screening with further modifications (Scott et al., 2016). MK-8931 displays a specific inhibitory effect on BACE1 at nalo mole levels over other aspartic proteases. This drug has been shown to penetrate the BBB very well (Kennedy et al., 2016). MK-8931 is the first BACE1 inhibitor that has been processed to the phase 3 clinical trial for AD, and the clinical trial results indicated that MK-8931 is well-tolerated for patients (Egan et al., 2018; Egan et al., 2019). However, phase 3 clinical trials with MK-8931 were terminated due its ineffectiveness in controlling AD progression or improving life quality of AD patients. Although targeting BACE1 by MK-8931 is not effective for treating AD patients, work conducted during development of embodiments herein indicate that MK-8931 can be repurposed for cancer immunotherapy as the drug can effectively redirect M2 TAMs into M1 macrophages to attack cancer cells in tumors. Because current immune checkpoint inhibitors such as anti-PD1 antibody have very poor capacity to penetrate the BBB or BTB, such treatment could not result in significant outcome for GBM and brain metastases of malignant tumors. As MK-8931 displays excellent permeability to enter the BBB and BTB, it overcomes the disadvantages of current immunotherapy.

In certain embodiments, the BACE1 inhibitor employed herein is provided in Table 1.

TABLE 1

| BACE1 inhibitor | Company | Structure |
|---|---|---|
| MK-8931/Verubecestat | Merck & Co. | 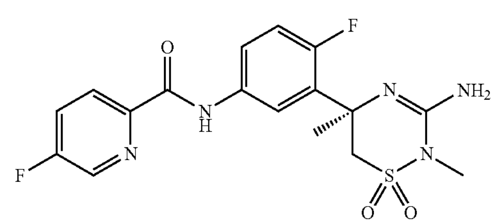 [SMILES: CN1C(N)=N[C@](C)(c2cc(NC(=O)c3ccc(F)cn3)ccc2F)CS1(=O)=O] |
| AZD3293/LY3314814/ Lanabecestat | AstraZeneca | 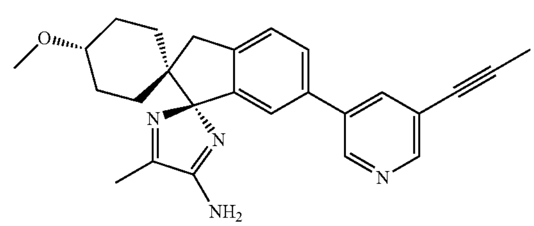 [SMILES: CC#Cc1cncc(-c2ccc3c(c2)[C@@]2(N=C(C)C(N)=N2)[C@]2(CC[C@@H](OC)CC2)C3)c1] |
| AZD3839 | AstraZeneca | 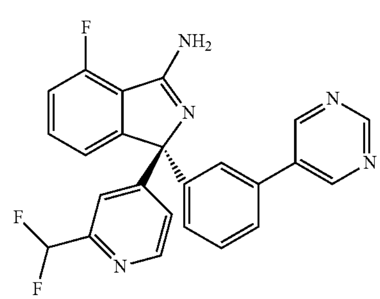 [SMILES: NC1=N[C@@](c2cccc(-c3cncnc3)c2)(c2ccnc(C(F)F)c2)c2cccc(F)c21] |

TABLE 1-continued

| BACE1 inhibitor | Company | Structure |
| --- | --- | --- |
| E2609/Elenbecestat | Eisai/Biogen | 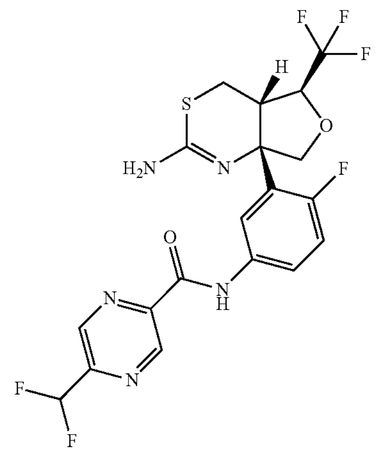 [SMILES: NC1=N[C@@]2(c3cc(NC(=O)c4cnc(C(F)F)cn4)ccc3F)CO[C@H](C(F)(F)F)[C@H]2CS1] |
| CNP520/Umibecestat | Novartis/Amgen | 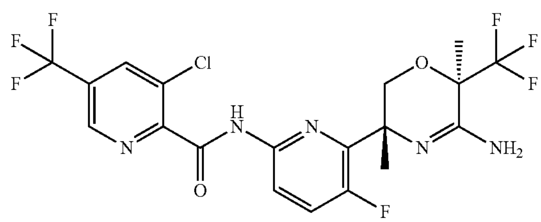 [SMILES: C[C@@]1(c2nc(NC(=O)c3ncc(C(F)(F)F)cc3Cl)ccc2F)CO[C@@](C)(C(F)(F)F)C(N)=N1] |
| JNJ-54861911/ Atabecestat | Janssen/Shionogi | 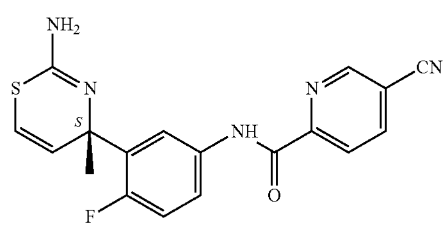 |
| PF-06751979 | Pfizer | 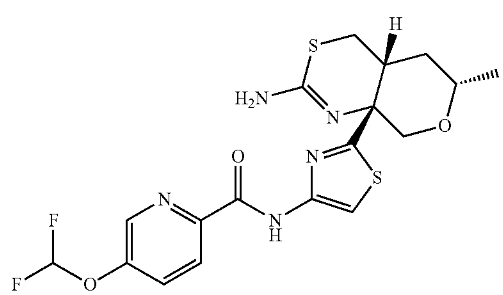 [SMILES: C[C@H]1C[C@H]2CSC(N)=N[C@@]2(c2nc(NC(=O)c3ccc(OC(F)F)cn3)cs2)CO1] |
| CTS-21166 | CoMentis | 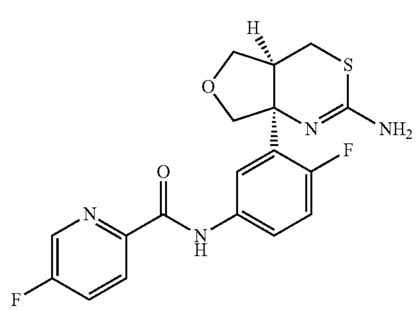 [SMILES: NC1=N[C@@]2(c3cc(NC(=O)c4ccc(F)cn4)ccc3F)COC[C@H]2CS1] |

TABLE 1-continued

| BACE1 inhibitor | Company | Structure |
|---|---|---|
| HPP854 | High Point | 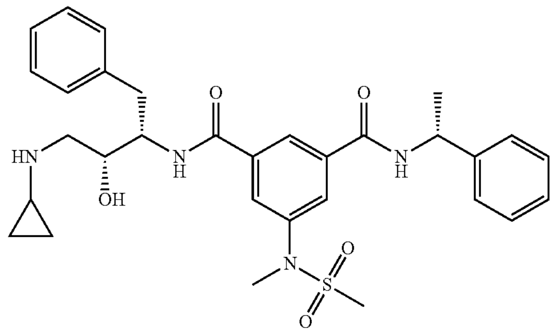 [SMILES: C[C@@H](NC(=O)c1cc(C(=O)N[C@@H](Cc2ccccc2)[C@H](O)CNC2CC2)cc(N(C)S(C)(=O)=O)c1)c1ccccc1] |
| TAK-070 | Takeda | 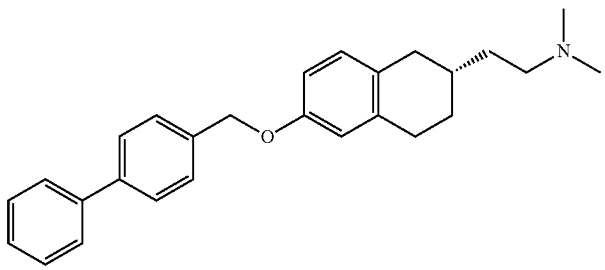 [SMILES: CN(C)CC[C@@H]1CCc2cc(OCc3ccc(-c4ccccc4)cc3)ccc2C1] |
| VTP-37948 | Vitae/Boehringer Ingelheim | 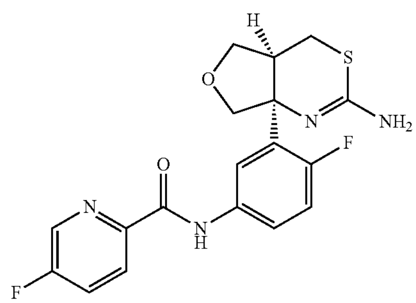 [SMILES: NC1=N[C@@]2(c3cc(NC(=O)c4ccc(F)cn4)ccc3F)COC[C@H]2CS1] |
| LY2886721 | Lilly | 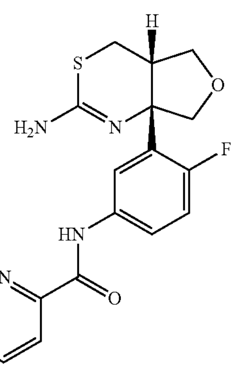 |
| PF-05297909 | Pfizer | 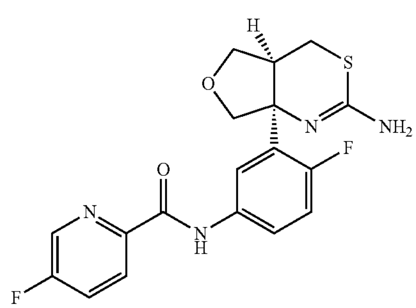 [SMILES: NC1=N[C@@]2(c3cc(NC(=O)c4ccc(F)cn4)ccc3F)COC[C@H]2CS1] |

TABLE 1-continued

| BACE1 inhibitor | Company | Structure |
|---|---|---|
| RG7129 | Roche | 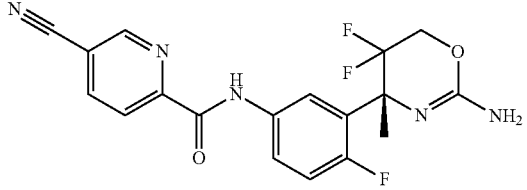 |

In certain embodiments, the BACE1 inhibitor is any of the compounds in Hsiao et al., Bioorganic & Medicinal Chemistry Letters 29 (2019) 761-777, including any of compounds 1-104. Hsiao et al. is incorporated by reference in its entirety, and specifically for any of the compounds recited therein. In other embodiments, the BACE1 inhibitor is any of the compounds in Moussa-Pacha et al., Med Res Rev. 2019; 1-46, including any of the compounds in Table 2. Moussa-Pacha et al. is incorporated by reference in its entirety, and specifically for any of the compounds listed in Table 2.

In some embodiments, methods further comprise administering to the subject an immune checkpoint inhibitor. In some embodiments, the immune checkpoint inhibitor is a protein or polypeptide that specifically binds to an immune checkpoint protein. In some embodiments, the immune checkpoint protein is selected from the group consisting of CTLA4, PD-1, PD-L1, PD-L2, A2AR, B7-H3, B7-H4, BTLA, KIR, LAG3, TIM-3 or VISTA. In some embodiments, the polypeptide or protein is an antibody or antigen-binding fragment thereof. In some embodiments, the immune checkpoint inhibitor is an interfering nucleic acid molecule. In some embodiments, the interfering nucleic acid molecule is an siRNA molecule, an shRNA molecule or an antisense RNA molecule. In some embodiments, the immune checkpoint inhibitor is selected from the group consisting of nivolumab, pembrolizumab, pidilizumab, AMP-224, AMP-514, STI-A1110, TSR-042, RG-7446, BMS-936559, BMS-936558, MK-3475, CT O11, MPDL3280A, MEDI-4736, MSB-0020718C, AUR-012 and STI-A1010.

EXAMPLES

Example 1

BACE1 Inhibition Promotes Macrophage Phagocytosis Against Cancer Cells to Suppress Malignant Growth Most malignant tumors contain abundant tumor-associated macrophages (TAMs) that mainly promote tumor growth and therapeutic resistance. Reprograming these tumor-supportive TAMs (M2) into tumor-suppressive macrophages (M1) is important for immunotherapy. Here, we found that inhibition of the β-site amyloid precursor protein cleaving enzyme 1 (BACE1) effectively redirected M2 TAMs into M1 macrophages and potently promoted macrophage phagocytosis against cancer cells to inhibit malignant growth. BACE1 is preferentially expressed by M2 TAMs and required for M2 polarization. BACE1 inhibition by MK-8931 potently suppressed tumor growth and significantly extended the survival of animals bearing xenografts of glioblastoma or brain metastases of lung adenocarcinoma. Moreover, low dose of radiation markedly enhanced TAM infiltration and synergized with MK-8931 treatment to inhibit malignant progression. Mechanistically, BACE1 maintains M2 TAMs through STAT3 signaling.

Results

Figure 1:
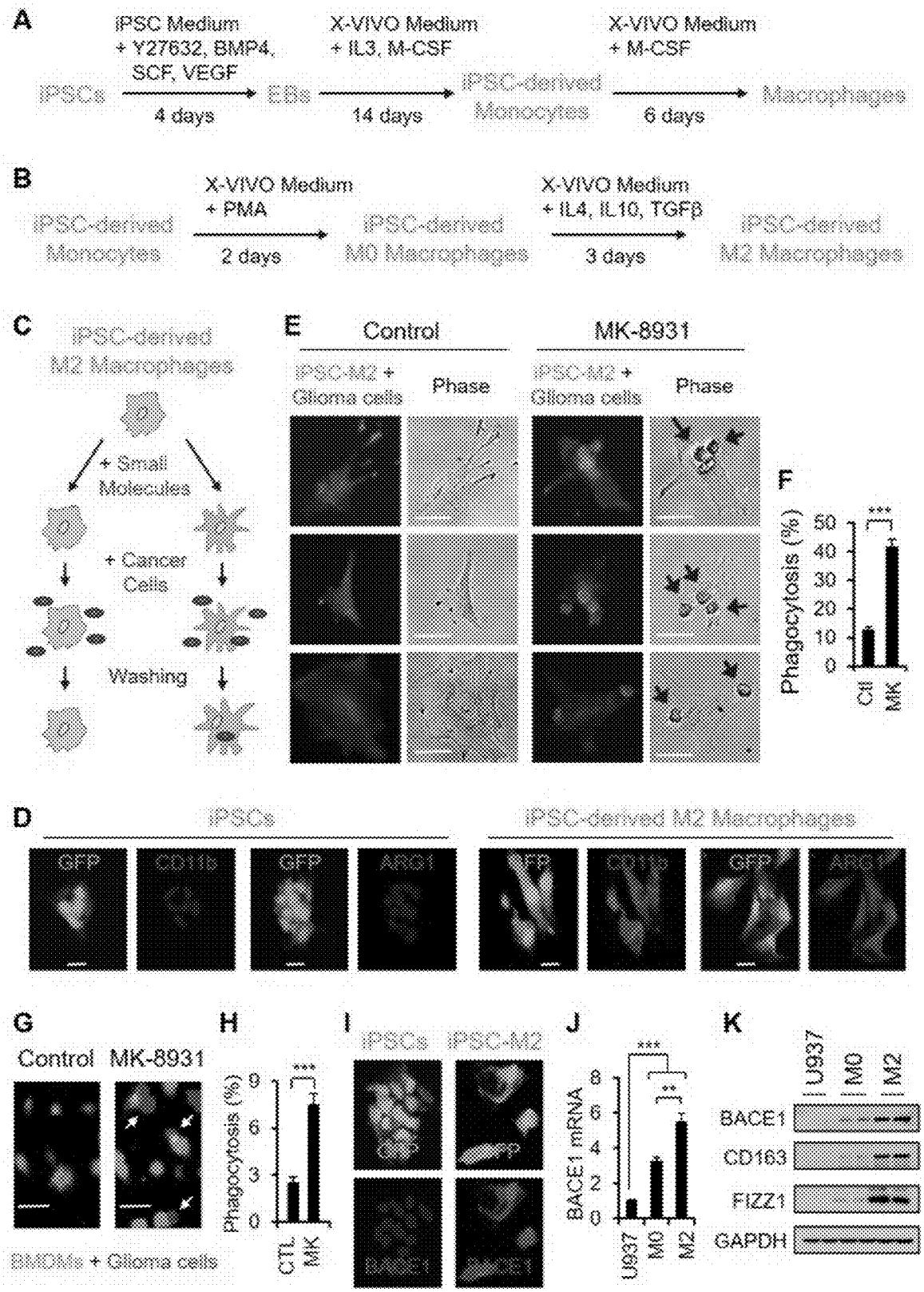
FIG. 1, panels A-K. Identification of the BACE1 Inhibitor MK-8931 as a Potent Activator That Promotes Macrophage Phagocytosis against Human Cancer Cells. (A) An exemplary protocol for generating monocytes and macrophages from human iPS cells (iPSCs) expressing GFP. Human iPSCs (GFP$^+$) were seeded on an ultra-low attachment plate and cultured with BMP4 (50 ng/mL), SCF (20 ng/mL), VEGF (20 ng/mL), and Y27632 (50 µM) in the iPSC medium for four days to form embryoid bodies (EBs). Then, the EBs were incubated in the X-VIVO medium with IL3 (25 ng/mL) and M-CSF (100 ng/mL) for 14 days to generate monocytes. Finally, the iPCS-derived monocytes were collected and induced to differentiate into macrophages by M-CSF (100 ng/mL) in the X-VIVO medium. (B) A protocol for the generation of M2 macrophages from iPSC-derived monocytes expressing GFP. Briefly, iPSC-derived monocytes (GFP$^+$) from (A) were primed with PMA (5 nM) for two days and then incubated in the X-VIVO medium with IL4 (20 ng/mL), IL10 (20 ng/mL), and TGFβ (20 ng/mL) for three days. (C) An illustration for the fluorescent screening assay to identify small molecules that can redirect macrophages from M2 into M1 subtype and promote macrophage phagocytosis against human cancer cells. Briefly, iPSC-derived M2 macrophages (GFP$^+$, in green) were seeded on wells of 24-well plates and treated with different small molecules for two days. Then, human cancer cells transduced with tdTomato (in red) were added to each well and co-incubated with the macrophages for two hours. After washing away free cancer cells, the images were captured and analyzed. Macrophage phagocytosis was detected as inclusion bodies of cancer cells (in red) with macrophages (in green). (D) Immunofluorescent analysis of macrophage marker expression in iPSC-derived M2 macrophages. The iPSC-derived M2 macrophages (GFP$^+$) and the matched iPSCs (GFP$^+$, control) were stained with specific antibodies against CD11b (total macrophage marker, in red) and ARG1 (M2 macrophage marker, in red) and then counterstained with DAPI (in blue). Representative immunofluorescent images showing that CD11b and ARG1 were expressed by the iPSC-derived M2 macrophages but not by the iPSCs. (E and F)—In vitro macrophage phagocytosis assay showing that the BACE1 inhibitor MK-8931 promoted phagocytosis of iPSC-derived macrophages against human glioma cells. The iPSC-derived M2 macrophages (GFP$^+$) were treated with MK-8931 (50 µg/mL) or the vehicle control for two days and then co-incubated with the tdTomato-expressing human glioma cells (T4121, in red) to detect macrophage phagocytosis as illustrated in (C). Representative fluorescent and phase contrast images (E) and quantification (F) showing that MK-8931 potently induced phagocytosis of iPSC-derived macrophages (in green) against human glioma cells (in red). * $p<0.001$. Ctl: Control; MK: MK-8931. (G and H)—In vitro macrophage phagocytosis assay showing that MK-8931 also promoted phagocytosis of the bone marrow-derived macrophages (BMDMs) against human glioma cells. BMDMs were treated with MK-8931 (50 µg/mL) or the vehicle control for two days and then labelled with the green fluorescent dye (CMFDA). The labelled BMDMs (in green) were co-incubated with the tdTomato-expressing human glioma cells (T4121, in red) for detecting macrophage phagocytosis as illustrated in (C). Representative fluorescent images (G) and quantification (H) showing that MK-8931 significantly promoted phagocytosis of BMDMs (in green) against human glioma cells (in red). * $p<0.001$. Ctl: Control; MK: MK-8931. (I) Immunofluorescent analysis of BACE1 expression in iPSC-derived M2 macrophages and the matched iPSCs (control). The iPSC-derived M2 macrophages (GFP$^+$) and the iPSCs (GFP$^+$) were immunostained with a specific antibody against BACE1 (in red) and counterstained with DAPI (in blue). Representative immunofluorescent images showing that BACE1 was expressed by the iPSC-derived M2 macrophages but not by the iPSCs. (J) qPCR analysis of BACE1 mRNA expression in U937 monocytes, U937-derived M0 macrophages, and U937-derived M2 macrophages. BACE1 is highly expressed by the U937-derived M2 macrophages. $p<0.01$ and *$p<0.001$. (K) Immunoblot analysis of BACE1 and the M2 macrophage makers CD163 and FIZZ1 in U937 monocytes, U937-derived M0 macrophages, and U937-derived M2 macrophages. GAPDH was blotted as the loading control. BACE1 is preferentially expressed by the M2 macrophages. Data are shown as mean±SEM.  $p<0.01$ and * $p<0.001$; Student's t test. Scale bars represent 2 µM.

Identification of the BACE1 Inhibitor MK-8931 as a Potent Activator of Macrophage Phagocytosis Against Cancer Cells To screen for potential small molecular modulators that can promote macrophage phagocytosis to eliminate cancer cells, we generated monocytes and macrophages from human iPS cells (iPSCs) expressing GFP according to the established protocols (Mia et al., 2014; Shi et al., 2017a; Yanagimachi et al., 2013) (FIGS. 1A and 1B), and developed an fluorescent phagocytosis assay using the GFP$^+$ iPSC-derived macrophages (in green) and the tdTomato-expressing glioma cells (in red) or lung carcinoma cells (in red) as illustrated (FIG. 1C). In this assay, we detected macrophage phagocytosis as fluorescent inclusion bodies of the cancer cells (tdTomato$^+$) within macrophages (GFP$^+$). To obtain GFP-expressing macrophages, we transduced iPSCs with constitutive expression of GFP and then derived macrophages from the GFP$^+$ iPSCs. We confirmed that the iPSC-derived M2 macrophages express the total TAM markers including IBA1 and CD11b and the M2 markers such as Fizz1 and ARG1 (FIG. 1D; FIG. 10A). To detect the small molecule-activated macrophage phagocytosis against cancer cells in the assay, glioma cells derived from human GBMs or lung cancer cells derived brain metastases of lung ADC were transduced with tdTomato expression. Thus, potential small molecules that can activate macrophages (GFP*) to phagocytize glioma cells (tdTomato*) could be detected under a fluorescent microscope during the screening (FIG. 1C).

We initially screened two drug libraries and some known inhibitors that displayed low toxicity and excellent BBB permeability in phase 2/3 clinical trials for other diseases including AD. To this end, we obtained nine potential "hits" and identified seven BACE1 inhibitors including MK-8931 as the most promising drug candidates that can potently promote phagocytosis of macrophages against glioma cells and lung ADC cells. The nine hits identified in this screen include MK-8931, PF-06751979, AZD3839, CNP520, E2609, AZD3293, JNJ-54861911, MK-8353, AZD6244. The seven most promising identified are all BACE1 inhibitors. It is noted that MK-8353 is an ERK inhibitor, and AZD6244 is a MEK inhibitor.

The in vitro fluorescent screening assay showed that MK-8931 treatment augmented phagocytosis of the iPSC-derived macrophages against glioma cells and lung ADC cells (FIGS. 1E and 1F; FIG. 10B). Moreover, MK-8931 treatment also promoted the phagocytosis of the bone marrow-derived macrophages against glioma cells (FIGS. 1G and 1H), suggesting MK-8931 is a potent activator of macrophage phagocytosis. As MK-8931 was originally developed as a BACE1 specific inhibitor for AD clinical trials (Scott et al., 2016; Thaisrivongs et al., 2016), and our screening showed that BACE1 inhibition by MK-8931 promoted macrophage phagocytosis (FIG. 1E-1H), BACE1 may play a critical role in regulating macrophage polarization or maintenance. We confirmed that BACE1 was highly expressed by the iPSC-derived M2 macrophages used for the screening (FIG. 1I). Consistently, the M2-like macrophages derived from U937 monocytes also express high levels of BACE1 at both mRNA and protein levels as measured by RT-PCR and immunoblot analyses (FIGS. 1J and 1K). Collectively, these data indicate that targeting BACE1 impacts macrophage function and that BACE1 may play an important role in the maintenance of M2 TAMs in malignant tumors.

Figure 2:
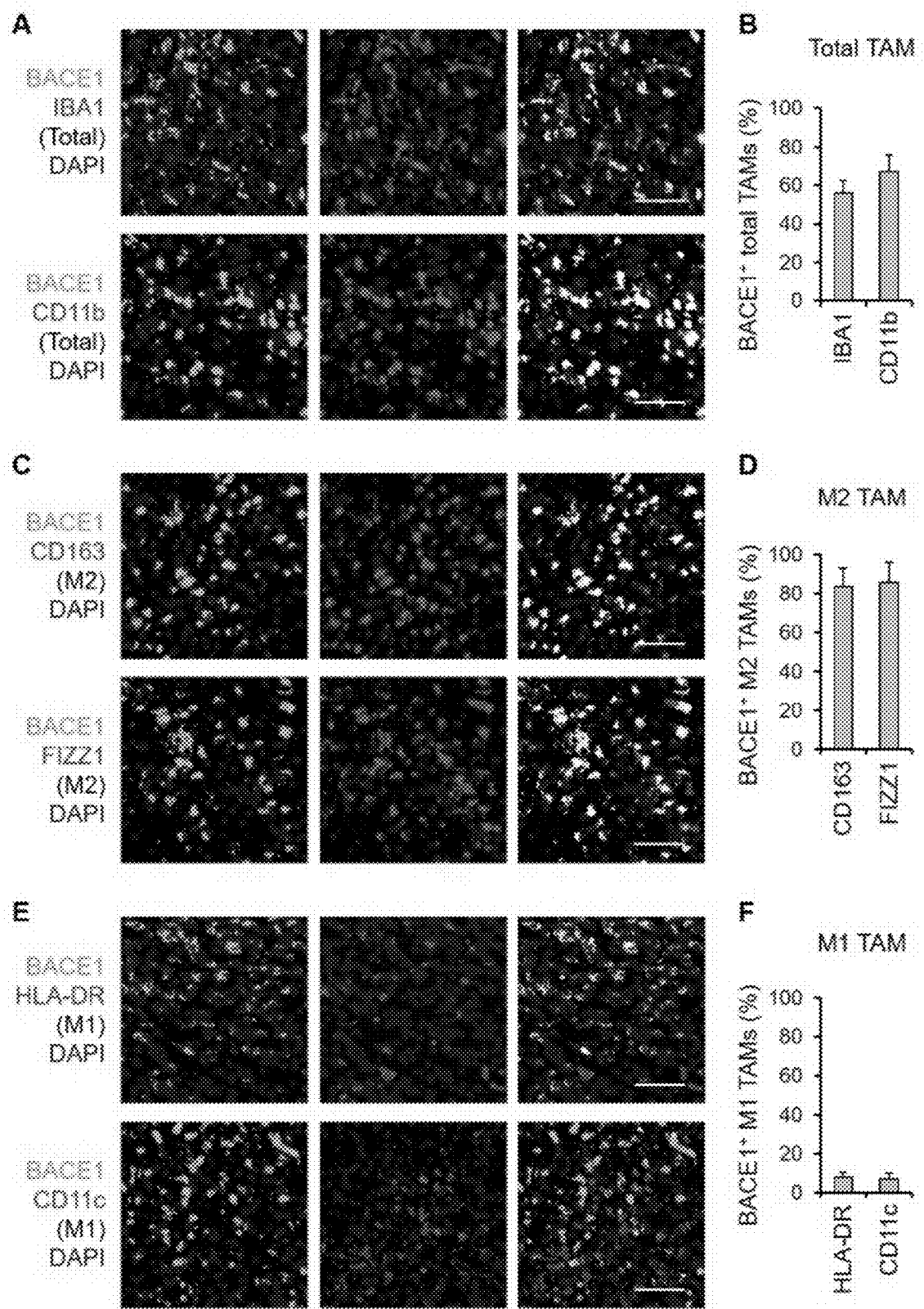
FIG. 2, panels A-F. BACE1 Is Preferentially Expressed by M2 TAMs in Human Primary GBM Tumors. (A and B) Immunofluorescent analysis of BACE1 and the total TAM marker IBA1 or CD11b in human GBM tumor tissues. Frozen sections of human GBMs were co-stained with specific antibodies against BACE1 (in green) and IBA1 or CD11b (in red) and then counterstained with DAPI (in blue). Representative immunofluorescent images (A) show the distribution and co-localization of BACE1 (in green) with the total TAM marker IBA1 or CD11b (in red) in a human GBM tumor (CCF2774). Quantification (B) shows the fractions of BACE1$^+$ TAMs (BACE1$^+$/IBA1$^+$ or BACE1$^+$/CD11b$^+$ cells) in total TAMs (IBA1$^+$ or CD11b$^+$ cells) in the GBM tumor. (C and D) Immunofluorescent analysis of BACE1 and the M2 TAM markers CD163 or FIZZ1 in human GBM tumor tissues. Frozen sections of GBMs were co-stained with specific antibodies against BACE1 (in green) and CD163 or FIZZ1 (in red) and then counterstained with DAPI (in blue). Representative immunofluorescent images (C) show the distribution and co-localization of BACE1 (in green) with the M2 TAM marker CD163 or FIZZ1 (in red) in a GBM tumor (CCF2774). Quantification (D) shows the fractions of BACE1$^+$ M2 TAMs (BACE1$^+$/CD163$^+$ or BACE1$^+$/FIZZ1$^+$ cells) in M2 TAMs (CD163$^+$ or FIZZ1$^+$ cells) in the GBM tumor. (E and F) Immunofluorescent analysis of BACE1 and the M1 TAM marker HLA-DR or CD11c in human GBM tumor tissues. Frozen sections of GBMs were co-stained with specific antibodies against BACE1 (in green) and HLA-DR or CD11c (in red) and then counterstained with DAPI (in blue). Representative immunofluorescent images (E) show the expression of BACE1 (in green) and M1 TAM markers (HLA-DR or CD11c, in red) in a GBM tumor (CCF2774). Quantification (F) shows the fractions of BACE1$^+$ M1 TAMs (BACE1$^+$HLA-DR$^+$ or BACE1$^+$CD11c$^+$ cells) in M1 TAMs (HLA-DR$^+$ or CD11c$^+$ cells) in the GBM tumor. Data are shown as mean±SEM. Scale bars represent 30 µM.

BACE1 is Preferentially Expressed by M2 TAMs in GBM Tumors and Predicts Poor Prognosis To investigate the potential role of BACE1 in regulating TAMs in GBM, we examined BACE1 expression in human GBM surgical specimens by double immunofluorescent staining, and found that BACE1 was mainly detected on a fraction of total TAMs expressing the macrophage marker IBA1 or CD11b (FIG. 2A). Quantitative analysis demonstrated that approximately 60% of the total IBA1$^+$ cells and about 67% of the total CD11b$^+$ cells expressed BACE1 (FIG. 2B). Further examination demonstrated that BACE1 was mainly co-expressed with the M2 TAM marker CD163 or FIZZ1 (FIG. 2C). Quantification indicated that the majority of M2 TAMs expressed BACE1, as approximately 83% of the CD163$^+$ TAMs and 86% of the FIZZ1$^+$ TAMs are BACE1-positive (FIG. 2D). In contrast, BACE1 was rarely co-expressed with the M1 TAM marker HLA-DR or CD11c (FIGS. 2E and 2F). Consistently, a similar BACE1 expression pattern with M2 TAM markers was detected in the GBM xenografts (FIG. 11A-11F). In addition, a correlation analyses of GBM databases demonstrated that the expression level of BACE1 is positively correlated with that of the M2 TAM marker CD163 and the total TAM marker IBA1 (FIGS. 12A and 12B). Collectively, these data demonstrate that BACE1 is preferentially expressed by the M2 TAMs in GBM tumors.

To interrogate the clinical significance of BACE1 expression in M2 TAMs in GBM tumors, we analyzed the relationship between BACE1 expression and GBM patient survival in several GBM databases including the Cancer Genome Atlas (TCGA), Rembrandt, Gravendeel and LeeY, and found an inverse correlation between BACE1 expression and the patient survival in all GBM databases (FIG. 12C-12F). GBM patients with higher BACE1 expression levels in their tumors clearly had a worse survival (FIG. 12C-12F), indicating that BACE1 expression predicts poor prognosis of GBM patients. The inverse correlation between BACE1 expression in M2 TAMs and the prognosis is consistent with the fact that M2 TAMs support tumor growth and malignant progression in GBM. These analyses further indicate that BACE1 expression may play an important role in maintaining polarization of M2 TAMs that are associated with poor prognosis.

BACE1 is Required for Maintaining M2 Macrophage Polarization

Figure 3:
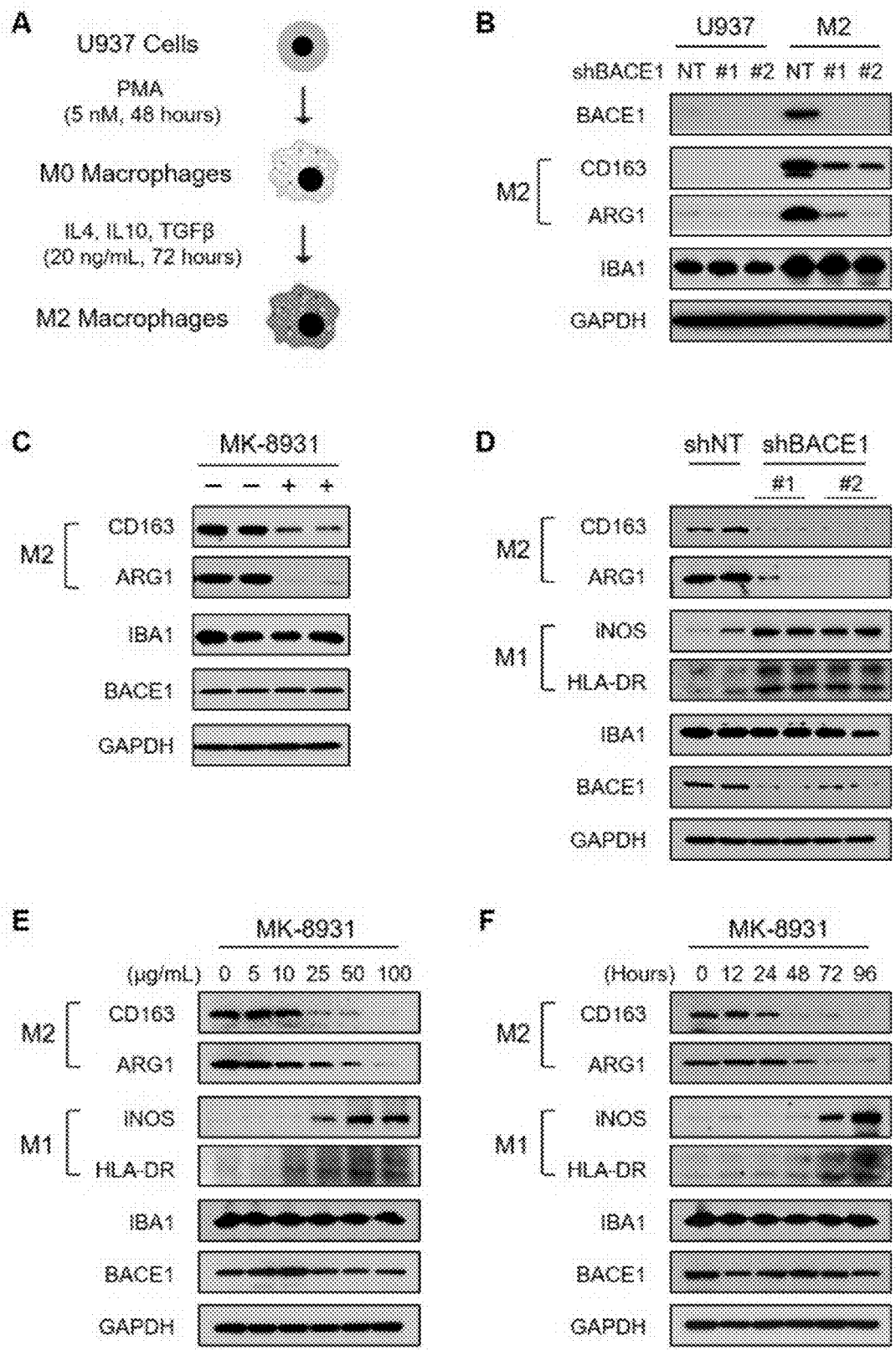
FIG. 3, panels A-F. BACE1 Is Required for Maintaining M2 Macrophage Polarization (A) A protocol for derivation of M2 macrophages from U937 monocytes in vitro. In brief, U937 cells were primed by PMA (5 nM) for two days to generate M0 macrophages and then incubated with IL4 (20 ng/mL), IL10 (20 ng/mL), and TGFβ (20 ng/mL) for three days to produce M2-like macrophages. (B) Immunoblot analyses of BACE1, the M2 macrophage markers (CD163 and ARG1), and the total macrophage marker IBA1 in U937 monocytes and the U937-derived M2 macrophages expressing shRNAs against BACE1 (shBACE1) or non-targeting sequence (NT). BACE1 knockdown reduced expression of the M2 macrophage markers in the U937-derived macrophages. (C) Immunoblot analyses of the M2 macrophage markers (CD163 and ARG1) and the total macrophage marker IBA1 in the U937-derived M2 macrophages with or without treatment of MK-8931. The U937-derived M2 macrophages were treated with MK-8931 (50 g/mL) or the vehicle control for three days and then harvested for the analyses. MK-8931 treatment reduced expression of the M2 macrophage markers but showed little effect on the total macrophage marker IBA1. (D) Immunoblot analyses of the M2 macrophage markers (CD163 and ARG1), the M1 macrophage markers (iNOS and HLA-DR), and the total macrophage marker IBA1 in the U937-derived M2 macrophages expressing shRNAs against BACE1 (shBACE1: #1 or #2) or non-targeting control (shNT). The U937-derived M2 macrophages were transduced with shBACE1 shNT through lentiviral infection. BACE1 knockdown reduced expression of the M2 markers (CD163 and ARG1) but induced expression of the M1 markers (iNOS and HLA-DR). (E) Immunoblot analyses of macrophage markers (M2: CD163 and ARG1; M1: iNOS and HLA-DR; total: IBA1) in U937-derived M2 macrophages treated with increased doses of MK-8931 (0, 5, 10, 25, 50, and 100 μg/mL) for three days. Mk-8931 treatment induced M1 marker expression but inhibited M2 marker expression in a dose-dependent manner. (F) Immunoblot analyses of macrophage markers (M2: CD163 and ARG1; M1: iNOS and HLA-DR; total: IBA1) in U937-derived M2 macrophages treated with MK-8931 (50 μg/mL) for different times (0, 12, 24, 48, 72, or 96 hours). MK-8931 treatment inhibited M2 marker expression but induced M1 marker expression in a time-dependent fashion. GAPDH was blotted as the loading control.

To determine the functional significance of BACE1 preferential expression in M2 macrophages, we examined the effects of BACE1 disruption by shRNA on M2 macrophages derived from U937 monocytes. M2 macrophages were induced from the PMA-primed U973 cells (known as M0 macrophage) by the cytokines IL4, IL10 and TGFβ according to an established protocol (Mia et al., 2014; Shi et al., 2017a) (FIG. 3A). Immunoblot blot analysis showed that BACE1 and the M2 markers CD163 and ARG1 were dramatically induced in the M2 macrophages derived from U937 monocytes (FIG. 3B). Importantly, BACE1 disruption by two specific and independent shRNAs (shBACE1) in the M2 macrophages markedly reduced the expression of the M2 markers CD163 and ARG1 (FIG. 3B), while the total TAM marker IBA1 expression was not affected by BACE1 knockdown, indicating that disrupting BACE1 expression inhibited the M2 polarization of macrophages. Moreover, treatment of the M2 macrophages with the BACE1 specific inhibitor MK-8931 markedly reduced expression of the M2 markers CD163 and ARG1 (FIG. 3C), indicating that functional inhibition of BACE1 suppressed the polarization of M2 macrophages. As BACE1 disruption or inhibition did not impact the expression of the total TAM marker IBA1, we speculated whether targeting BACE1 could promote phenotypic transition of M2 macrophage into M1 type. To address this issue, we knocked down BACE1 in the M2 macrophages and found that BACE1 disruption indeed induced the expression of the M1 makers including HLA-DR and iNOS, while the expression of the M2 markers CD163 and ARG1 were dramatically reduced after BACE1 disruption (FIG. 3D). Moreover, functional inhibition of BACE1 by MK-8931 treatment in the M2 macrophages effectively induced expression of the M1 makers HLA-DR and iNOS but inhibited the expression of the M2 markers CD163 and ARG1 in dose- and time-dependent manners (FIGS. 3E and 3F). These results indicate that BACE1 disruption or inhibition potently triggers phenotypic switch of macrophages from M2 to M1 type. Collectively, these data demonstrate that BACE1 is required for the polarization and maintenance of M2 macrophages. As BACE1 disruption or inhibition promotes the M2 to M1 transition of macrophages, targeting BACE1 by its specific inhibitor MK-8931 may effectively redirect tumor-supportive M2 TAMs into tumor-suppressive M1 macrophages to inhibit malignant growth.

Figure 4:
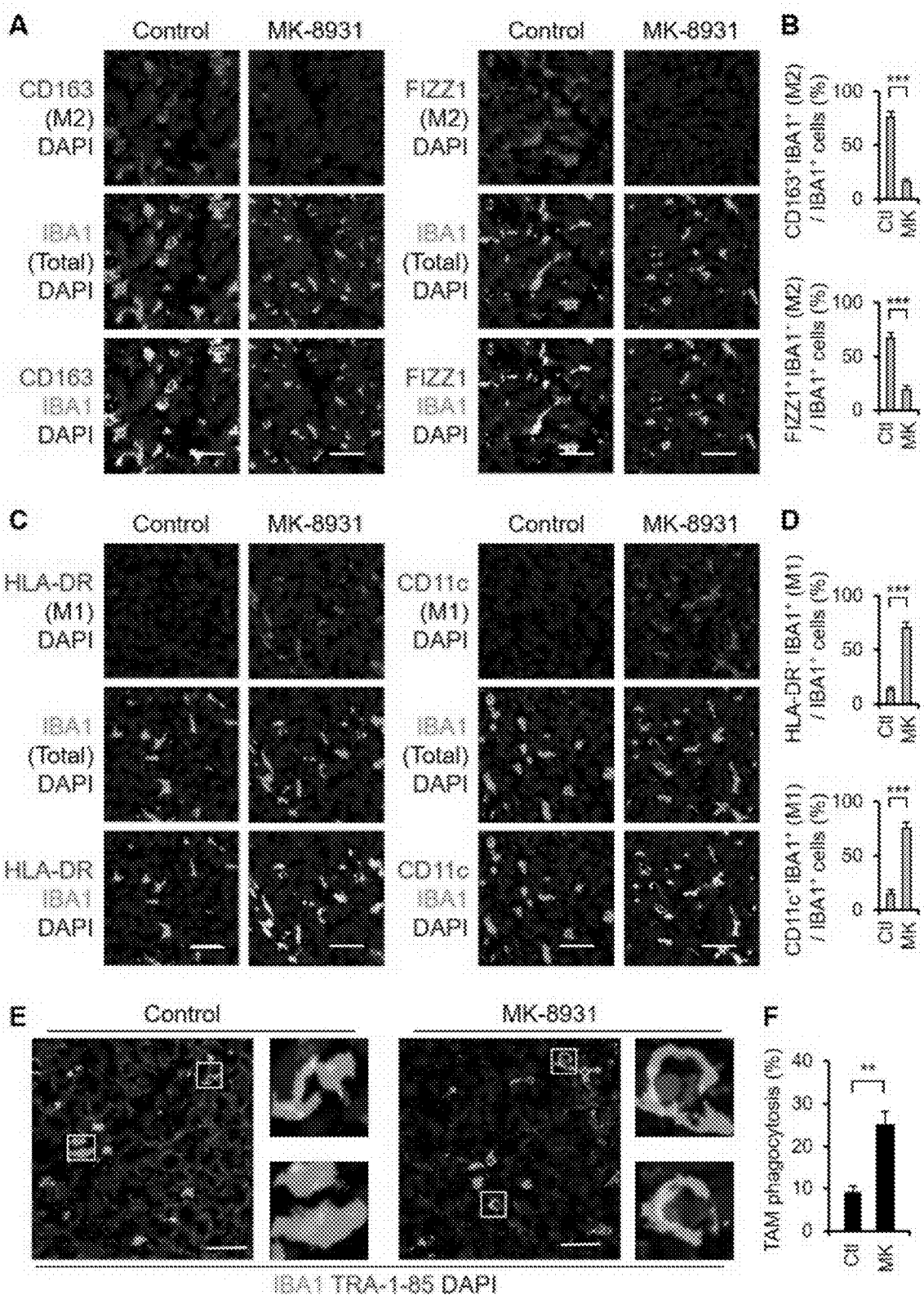
FIG. 4, panels A-F. BACE1 Inhibition by MK-8931 Converts M2 TAMs into M1 Macrophages to Phagocytize Glioma Cells in GBM Xenografts. (A and B) Density analysis of M2 TAMs by immunofluorescent staining of the M2 TAM marker (CD163 or FIZZ1) and the total TAM marker IBA1 and in GBM xenografts treated with MK-8931 or vehicle control. GBM xenografts were established by implantation of glioma stem cells (T4121) through intracranial injection. Seven days after transplantation, the tumor-bearing mice were treated with MK-8931 (30 mg/kg) or the vehicle control once daily by oral gavage for two weeks. Frozen brain sections were immunostained with specific antibodies against CD163 or FIZZ1 (M2 TAM marker, in red) and IBA1 (in green) and counterstained with DAPI (in blue). Representative immunofluorescent images (A) showing M2 TAMs (CD163$^+$ or FIZZ1$^+$, in red) and total TAMs (IBA1$^+$, in green) in the MK-8931-treated or control GBM xenografts. Quantifications (B) showing that MK-8931 treatment significantly reduced density of M2 TAMs (CD163$^+$/IBA1$^+$ or FIZZ1$^+$/IBA1$^+$) in GBM xenografts. * p<0.001. (C and D) Density analysis of M1 TAMs by immunofluorescent staining of the M TAM marker (HLA-DR or CD11c) and the total TAM marker IBA1 and in GBM xenografts treated with MK-8931 or vehicle control. Frozen brain sections were immunostained with specific antibodies against HLA-DR or CD11c (M TAM marker, in red) and IBA1 (in green) and counterstained with DAPI (in blue). Representative immunofluorescent images (C) showing M1 TAMs (HLA-DR$^+$ or CD11c$^+$, in red) and total TAMs (IBA1$^+$, in green) in the MK-8931-treated or control GBM xenografts. Quantifications (D) showing that MK-8931 treatment significantly increased density of M1 TAMs (HLA-DR$^+$/IBA1$^+$ or CD11c$^+$/IBA1$^+$) in GBM xenografts. * p<0.001. (E and F) In vivo phagocytosis of TAMs against human glioma cells in the MK-8931-treated or control GBM xenografts. Frozen brain sections were immunostained with specific antibodies against IBA1 (in green, detecting TAMs) and the human cell antigen TRA-1-85 (in red, detecting glioma cells) and counterstained with DAPI (in blue). Representative images (E) showing in vivo TAM phagocytosis as inclusion bodies of glioma cells (TRA-1-85$^+$, in red) with TAMs (IBA1, in green) in the MK-8931 treated GBM xenografts but not in the control tumors. Quantification (E) showing that MK-9831 treatment significantly increased the inclusion bodies of glioma cells (TRA-1-85$^+$, in red) with TAMs (IBA1$^+$, in green) in GBM xenografts, indicating that MK-8931 treatment promoted TAM phagocytosis. p<0.01. Data are shown as mean±SEM. p<0.01 and *** p<0.001; Student's t-test. Scale bar represents 30 μM. Ctl: Control; MK: MK-8931.

BACE1 Inhibition by MK-8931 Redirects M2 TAMs into M1 Macrophages to Phagocytize Tumor Cells In Vivo To evaluate the therapeutic impact of BACE1 inhibition on activating TAM phagocytosis for cancer treatment, we next examined the effect of MK-8931 treatment on TAMs in GBM tumors that contain abundant M2 TAMs (Shi et al., 2017a; Zhou et al., 2015). GBM xenografts were established by implantation of GSCs (T4121 or T387) through intracranial injection. The tumor-bearing mice were then treated with MK-8931 (30 mg/kg) or the vehicle control once daily by oral gavage for 2 weeks. Immunofluorescent analyses of the M1/M2 markers in the xenografts demonstrated that MK-8931 treatment markedly reduced M2 TAMs as marked by CD163$^+$/IBA1$^+$ or FIZZ1$^+$/IBA1$^+$ cells (FIGS. 4A and 4B; FIGS. 13A and 13B). In contrast, the M1 TAMs marked by HLA-DR$^+$/IBA1$^+$ or CD11c$^+$/IBA1$^+$ were strikingly increased in the xenografts treated with MK-8931 relative to the control tumors (FIGS. 4C and 4D; FIGS. 13C and 13D). In addition, MK-8931 treatment reduced the M2 TAM-related inflammation factors such as TGFβ and IL10 but enhanced the production of M1 TAM-associated factors including TNFα and IL1β in GBM xenografts (FIG. 14A-14H). These data indicate that functional inhibition of BACE1 by MK-8931 effectively converts M2 TAMs to M1 macrophages in tumors. Because targeting BACE1 by MK-8931 promoted macrophage phagocytosis against cancer cells in vitro (FIGS. 1E and 1F), we next examined whether BACE1 inhibition by MK-8931 treatment in vivo promotes TAM phagocytosis against tumor cells in GBM xenografts. To address this critical point, we detected macrophage phagocytosis by labeling TAMs with IBA1 staining (in green) and the human tumor cells with the TRA-1-85 staining (in red) in GBM xenografts treated with MK-8931 or control, and found that MK-8931 treatment resulted in a significant increase of inclusion bodies of tumor cells (TRA-1-85$^+$, red) within TAMs (IBA1$^+$, green) (FIGS. 4E and 4F). These results indicate that BACE1 inhibition by MK-8931 treatment promotes phagocytic activity of TAMs against glioma cells in tumors, which is consistent with the fact that BACE1 inhibition effectively converts tumor-supportive M2 TAMs into tumor-suppressive M1 macrophages in vivo. Collectively, our data demonstrate that BACE1 inhibition by MK-8931 potently reprograms M2 TAMs into M1 macrophages to promote macrophage phagocytosis against cancer cells in tumors.

Figure 5:
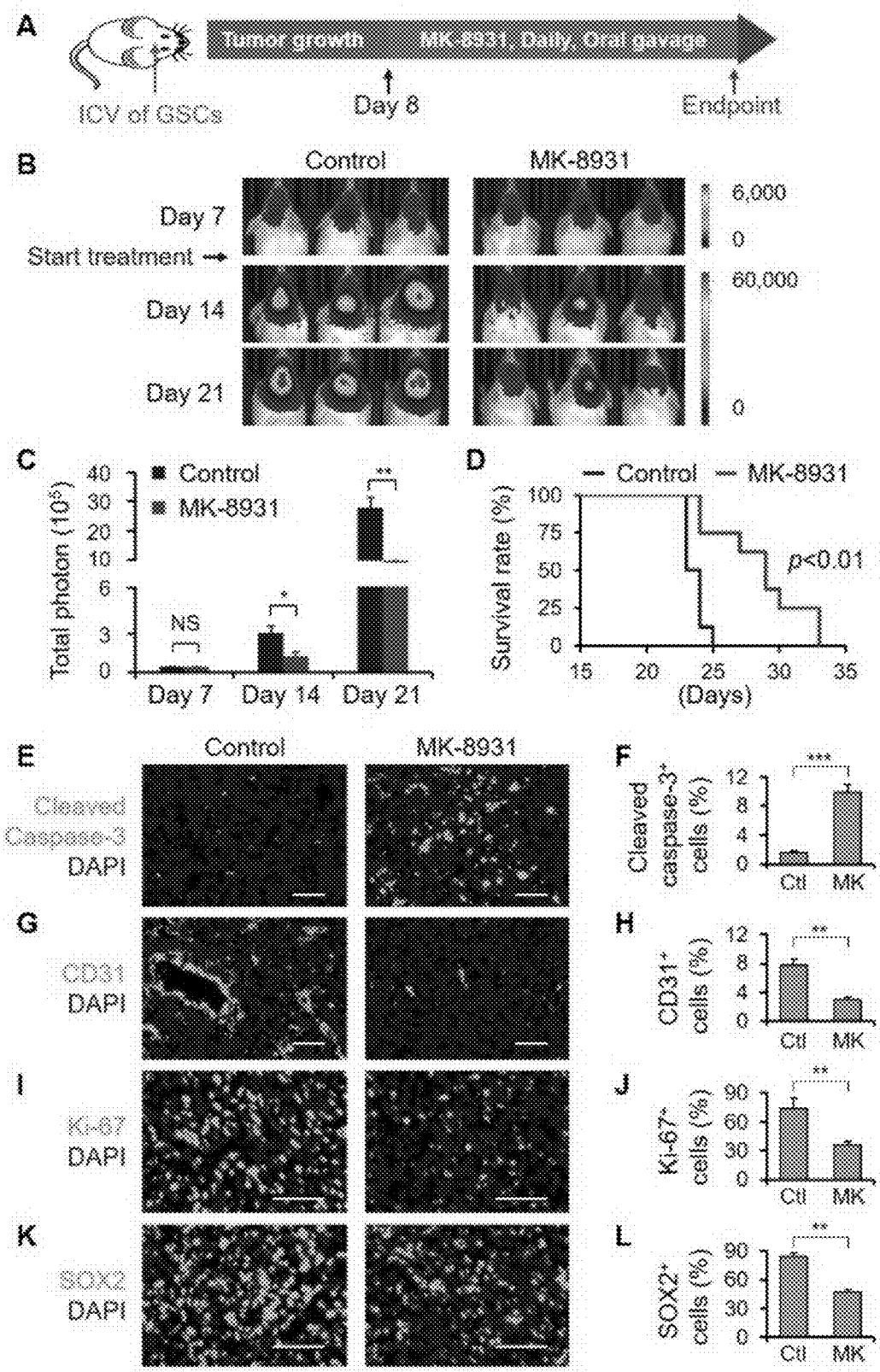
FIG. 5, panels A-L. Targeting BACE1 by MK-8931 Potently Inhibits GBM Tumor Growth and Extends Survival of Animals Bearing Intracranial GBM Xenografts. A) A treatment schedule showing an exemplary preclinical trial of MK-8931 for GBM therapy in GSC-derived GBM xenograft models. Briefly, human glioma stem cells (T4121 GSCs) expressing luciferase were transplanted into NSG mouse brains through intracranial injection to establish GBM xenografts. Eight days after the transplantation, the tumor-bearing mice were treated with MK-8931 (30 mg/kg) or the vehicle control once daily by oral gavage until the appearance of humane endpoints. Bioluminescent imaging (IVIS) were performed twice per week to monitor tumor growth before and after MK-8931 treatment. Mice were maintained until the development of neurological signs to examine the survival, and then brains bearing the tumors were harvested for further analyses. (B and C) In vivo bioluminescent analysis to monitor intracranial tumor growth of GBM xenografts derived from T4121 GSCs expressing luciferase in mice treated with MK-8931 (30 mg/kg/daily) or the vehicle control. Representative bioluminescent images (B) at the indicated days were shown. Quantification (C) shows the mean bioluminescence of the control mice (7 mice/group) and the MK-8931-treated mice (7 mice/group) on Days 7, 14, and 21. MK-8931 treatment significantly inhibited tumor growth of GBM xenografts. * p<0.05 and  p<0.01. (D) Kaplan-Meier survival curves of the mice bearing the GSC-derived GBM xenografts treated with MK-8931 (30 mg/kg/daily) or the vehicle control. Each group contains seven mice. Log-rank analysis was used to assess the significance. MK-8931 treatment significantly extended the survival of mice bearing the GBM tumors. p<0.01 as indicated. (E and F) Detection of apoptosis by immunofluorescent staining of cleaved caspase-3 in the GSC-derived xenografts treated with MK-8931 or the vehicle control. Frozen sections were immunostained with a specific antibody against cleaved caspase-3 (in green) and counterstained with DAPI (in blue). Representative immunofluorescent images of cleaved caspase-3 (E) in the GBM xenografts treated with MK-8931 or the vehicle control were shown. Quantification (F) shows that MK-8931 treatment significantly increased apoptosis (cleaved caspase-3$^+$ cells) in the GBM xenografts relative to the control tumors. * p<0.001. (G and H) Vessel density analysis by immunofluorescent staining of CD31 in the GSC-derived xenografts treated with MK-8931 or the vehicle control. Frozen sections were immunostained with a specific antibody against CD31 (in green) and counterstained with DAPI (in blue). Representative immunofluorescent images of CD31 (G) in the GBM xenografts treated with MK-8931 or the vehicle control were shown. Quantification (H) shows that MK-8931 treatment significantly reduced vessel density (CD31V cells) in the GBM xenografts. ** p<0.01. (I and J) Cell proliferation analysis by immunofluorescent staining of Ki-67 in the GSC-derived xenografts treated with MK-8931 or the vehicle control. Frozen sections were immunostained with a specific antibody against Ki-67 (in green) and counterstained with DAPI (in blue). Representative immunofluorescent images of Ki-67 (I) in the GBM xenografts treated with MK-8931 or the vehicle control were shown. Quantification (J) shows that Mk-8931 treatment significantly reduced proliferative cells (Ki-67+) in the GBM xenografts.

Targeting BACE1 by MK-8931 Potently Inhibited Tumor Growth and Extended Survival of Animals Bearing the GBM Xenografts Given the phenotypic switch of TAMs (M2 to M1) and the enhanced macrophage phagocytosis induced by BACE1 inhibition via MK-8931 treatment, we next examined whether MK-8931 treatment in vivo could suppress tumor growth. To address this important point, we treated the mice bearing the GBM xenografts derived from the luciferase-expressing GSCs (T4121 or T387) with MK-8931 (30 mg/kg) or the control once daily through oral gavage and then monitored the tumor growth under IVIS as illustrated (FIG. 5A). Bioluminescent imaging demonstrated that MK-8931 treatment potently inhibited GBM tumor growth (FIGS. 5B and 5C; FIGS. 15A and 15B). As a consequence, MK-8931 treatment significantly extended the survival of mice bearing the GBM xenografts (FIG. 5D; FIG. 15C). To further understand the cellular effects MK-8931 treatment on GBM tumor growth, we examined macrophage phagocytosis, tumor angiogenesis, cell apoptosis, and proliferation in the MK-8931-treated and the control tumors. Consistently, MK-8931 treatment significantly increased TAM phagocytosis against cancer cells as detected by inclusion bodies of human glioma cells (TRA-1-85+, red) within TAMs (IBA1$^+$, green) (FIGS. 15D and 15E). Moreover, MK-8931 treatment notably increased cell apoptosis as indicated by cleaved caspase 3 staining (FIGS. 5E and 5F; FIGS. 15F and 15G). In addition, MK-8931 treatment resulted in reduction in vessel (CD31$^+$) density (FIGS. 5G and 5H; FIGS. 15H and 15I), cell proliferation (Ki67$^+$) (FIGS. 5I and 5J; FIGS. 15J and 15K), and the population of glioma stem cells (GSCs, SOX2+) in the tumor (FIGS. 5K and 5L; FIGS. 15L and 15M). These additional phenotypes could be caused by the reduced M2 tumor-supportive TAMs but unlikely to be the direct effects of MK-8931 treatment, because MK-8931 treatment in cell culture did not affect GSC sphere formation, proliferation, cell viability and apoptosis in vitro (FIG. 16A-16E). As M2 TAMs play critical roles in supporting tumor angiogenesis as well as the proliferation and maintenance of GSCs (Shi et al., 2017a; Zhou et al., 2015), and GSCs also generate vascular pericytes and secrete VEGF to promote vessel formation (Bao et al., 2006b; Cheng et al., 2013), the reduced M2 TAMs caused by MK-8931 treatment might indirectly result in some of the observed phenotypes including the reduction in vessel density, cell proliferation, and GSC population in vivo. However, the reduced tumor-supportive M2 TAMs, the increased tumor-suppressive M1 TAMs, and the activated macrophage phagocytosis induced by MK-8931 treatment could all contribute to the increased cell death in the treated tumors. Taken together, our preclinical data demonstrate that BACE1 inhibition by MK-8931 potently redirects M1 TAMs into M1 macrophages and promotes macrophage phagocytosis against cancer cells to potently suppress malignant growth.

Low Dose of Radiation Enhanced TAM Infiltration and Effectively Synergized with MK-8931 Treatment to Inhibit Malignant Growth To improve the efficacy of macrophage-based immunotherapy through BACE1 inhibition, we sought to find an effective way to enhance macrophage infiltration into tumors. We irradiated mouse brains bearing the GBM xenografts with low dose of IR (2×2 Gy) to allow more TAM infiltration and then treated mice with MK-8931 as illustrated (FIG. 6A). We found that the combined treatment achieved strongest inhibition on GBM growth relative to IR or MK-8931 treatment alone (FIGS. 6B and 6C). As a consequence, the combined treatment conferred the longest survival extension among four experimental groups (FIG. 6D). To understand the property of TAMs in GBM xenografts treated with IR, MK-8931, or IR plus MK-8931, we examined TAM density and subtypes in the tumors in the experimental and control groups. We confirmed that total TAM density (IBA1$^+$ cells) was remarkably increased by the low dose of IR (FIG. 17A-17C), which is consistent with the previous reports that IR enhanced TAM infiltration into tumors (Kioi et al., 2010; Vatner and Formenti, 2015). Surprisingly, the majority of TAMs induced by the low dose of IR exhibited M2 phenotype but not M1 subtype as evidenced by the expression of CD163 but not HLA-DR (FIG. 17A-17C). However, MK-8931 treatment effectively converted M2 TAMs (CD163+) into M1 macrophages (HLA-DR$^+$) in the GBM xenografts treated with IR plus MK-8931 (FIG. 17A-17C), suggesting that BACE1 inhibition by MK-8931 treatment is able to redirect the IR-enhanced M2 TAMs into M1 macrophages. Moreover, immunostaining analyses of the apoptotic maker cleaved caspase 3 demonstrated that the combined IR (low dose) and MK-8931 treatment resulted in significantly more apoptotic cell death than the MK-8931 and IR treatment alone (FIGS. 17D and 17E). Importantly, the apoptosis induced by IR plus MK-8931 treatment (25.9±3.1%) is significantly more than the sum of apoptosis induced by MK-8931 treatment alone (10.4±0.9%) and the low dose of IR alone (3.1±0.7%) (FIG. 17E), indicating that low dose of IR indeed synergized with MK-8931 treatment to inhibit tumor growth. Collectively, these data demonstrate that the enhanced TAM infiltration by low dose of IR effectively synergizes with MK-8931 treatment to suppress malignant growth and thus increases the survival of the tumor-bearing animals.

BACE1 Maintains M2 TAMs Through STAT3 Activation

We next sought to understand the molecular mechanisms by which BACE1 maintains M2 TAM polarization. Because STAT3 and STAT6 have been shown to be the key transcriptional regulators in M2 macrophage polarization (Guerriero, 2018; Murray, 2017; Sica and Mantovani, 2012), we interrogated the potential role of STAT3 or STAT6 in the BACE1-mediated maintenance of M2 TAMs. Surprisingly, we found that the activating phosphorylation of STAT3 (pSTAT3-Y705) but not STAT6 (pSTAT6-Y641) was significantly down-regulated by BACE1 disruption with shBACE1 (FIG. 7A) or inhibition by MK-8931 (FIG. 7B). Consistently, MK-8931 treatment in vivo profoundly reduced the pSTAT3$^+$ TAMs (identified as pSTAT3+/IBA1$^+$) and total pSTAT3$^+$ cells in GBM xenografts (FIG. 7C-7E). To further determine whether BACE1 mediates through STAT3 signaling to maintain M2 TAMs, we examined if ectopic expression of a constitutively active STAT3 (STAT3-

C) could rescue the attenuated M2 phenotype induced by BACE1 disruption or inhibition. Indeed, ectopic expression of STAT3-C restored expression of the M2 TAM markers CD163 and ARG1 attenuated by BACE1 knockdown or inhibition with MK-8931 treatment in the monocyte-derived macrophages (FIGS. 7F and 7G). Importantly, the expression of STAT3-C abolished the increased expression of the M1 TAM markers iNOS and HLA-DR induced by BACE1 disruption or inhibition in the macrophages (FIGS. 7F and 7G). Thus, ectopic expression of STAT3-C restored the M2 phenotype impaired by BACE1 disruption or inhibition in macrophages. Collectively, these data demonstrate that BACE1 maintains M2 TAMs mainly through STAT3 activation, indicating that BACE1-mediated STAT3 activation is required for M2 TAM polarization.

MK-8931 Treatment Potently Suppressed Malignant Growth of Brain Metastases of Lung Adenocarcinoma As TAMs are commonly present in most types of malignant tumors (Mantovani et al., 2017), we next examined whether targeting BACE1 by MK-8931 could also effectively inhibit tumor growth of other lethal cancers. Because lung ADC is the most common type of lung cancer that accounts for the most cancer incidents and is the leading cause of cancer-related death worldwide (Bray et al., 2018; Fitzmaurice et al., 2018), and lung ADC often causes brain metastases that are highly lethal with limited treatment option (Sperduto et al., 2010), we examined whether MK-8931 treatment could suppress the tumor growth and malignant progression of brain metastases of lung ADC. We established intracranial xenografts of lung cancer by transplanting luciferase-expressing lung ADC cells (H1002, derived from brain metastases of human lung ADC) into NSG mice through intracranial injection, and then treated the tumor-bearing mice with MK-8931 as illustrated (FIG. 18A). Bioluminescent imaging (IVIS) demonstrated that MK-8931 treatment also potently inhibited tumor growth of lung ADC in brains (FIGS. 8A and 8B). Consistently, MK-8931 treatment significantly extended the survival of mice bearing the intracranial xenografts of lung ADC (FIG. 8C). Moreover, BACE1 inhibition by MK-8931 treatment also induced phenotypic switch of TAMs from M2 to M1 subtype as evidenced by decreased M2 markers and increased M1 markers (FIG. 8D-8G). Importantly, MK-8931 treatment also significantly augmented macrophage phagocytosis against cancer cells in the lung ADC brain metastases as evidenced by increased inclusion bodies of human lung cancer cells (TRA-1-85$^+$, red) within TAMs (IBA1$^+$, green) (FIGS. 8H and 8I). Further analyses confirmed that MK-8931 treatment resulted in a significant increase in apoptotic cell death marked by activated caspase 3 (FIGS. 18B and 18C), a reduction in tumor vessel (CD31$^+$) density (FIGS. 18D and 18E), and a decrease in cell proliferation (Ki67$^+$) in the tumors (FIGS. 18F and 18G).

Macrophages are critical immune cells that play essential roles in tissue homeostasis and innate immunity. In response to varied stimulations or changes in tissue microenvironment, macrophages undergo specialized polarization to execute diverse functions (Murray, 2017). In malignant tumors, TAMs are recruited and educated by cancer cells in the tumor microenvironment. The majority of TAMs (M2) play supportive roles to promote tumor growth and malignant progression including cancer invasion, tumor metastasis, immune evasion, and therapeutic resistance (Qian and Pollard, 2010), although a small fraction of TAMs (M1) may have a tumor-suppressive role (Noy and Pollard, 2014; Zhou and Bao, 2014b). Thus, either targeting M2 TAMs to inhibit their tumor-supportive role or reprograming M2 TAMs into M1 macrophages to activate their phagocytosis against cancer cells is an attractive therapeutic approach. To make a smart use of the abundant M2 TAMs in malignant tumors for the macrophage-based immunotherapy, redirecting M2 TAMs into M1 macrophages to exert their anti-cancer capacity is a better therapeutic strategy. Although depleting TAMs by targeting the colony-stimulating factor 1 receptor (CSF-1R) showed inhibition on the tumor growth of GBM in animal models (Pyonteck et al., 2013), clinical trials with CSF-1R inhibitors failed to show a significant efficacy for treating GBM in human (Butowski et al., 2016). In addition, as CSF-1R is expressed by circulating monocytes and other normal cells, targeting CSF-1R showed serious toxic effects in the clinical trials (Papadopoulos et al., 2017), making the therapeutics targeting CSF-1R ineffective for clinical use (Gelderblom et al., 2018). This Example demonstrated that redirecting M2 TAMs into M1 macrophages by targeting BACE1 with its specific inhibitor MK-8931 potently promoted TAM phagocytosis against tumor cells and effectively inhibited tumor growth to extend the survival of animals bearing GBM xenografts or brain metastases of lung ADC. As BACE1 inhibition by MK-8931 has been demonstrated to be very safe in the clinical trials for AD treatment (Egan et al., 2018; Egan et al., 2019), and MK-8931 can penetrate the BBB or BTB very well (Kennedy et al., 2016), converting M2 TAMs into M1 macrophages by BACE1 inhibition with MK-8931 offers a macrophage-based new immunotherapy to overcome the shortcomings of targeting CSF-1R. Because BACE1 is preferentially expressed by the M2 TAMs and required for the maintenance of M2 TAMs, BACE1 represents an attractive therapeutic target for reprograming M2 TAMs into M1 macrophages to improve tumor immunotherapy for lethal cancers including GBM and brain metastases of lung cancer (FIG. 9).

BACE1 is a type I transmembrane β-secretase that can cleave amyloid precursor protein to cause accumulation of Aβ production in brains of AD patients (Hussain et al., 1999; Sinha et al., 1999; Vassar et al., 1999; Yan et al., 1999). Early studies showed that BACE1 deficiency is well-tolerated in the knockout mice without obvious effects on development, behavior, and fertility (Yan, 2017), implicating that targeting BACE1 should not result in obvious side effects. This Example demonstrated that BACE1 plays a critical role in the polarization and maintenance of M2 TAMs in tumors. BACE1 inhibition potently reprograms M2 TAMs into M1 macrophages to promote TAM phagocytosis against cancer cells in vivo. Interestingly, microglia in BACE1-deficient mice also showed an enhanced phagocytosis toward cellular debris after nerve damage (Farah et al., 2011; Liu et al., 2016), but the essential role of BACE1 in M2 macrophage polarization in tumors has not been reported. In this Example, we identified BACE1 as an important regulator that affects M2/M1 phenotype switch in tumors. Importantly, BACE1 inhibition did not cause cell death of M2 TAMs but redirected M2 TAMs into M1 macrophages that display potent phagocytic activity to attack cancer cells in tumors, making therapeutic targeting of BACE1 more attractive for tumor immunotherapy. As several BACE1 selective inhibitors have been developed for AD in clinical trials and are well-tolerated in patients (Cebers et al., 2017; Egan et al., 2018; Kennedy et al., 2016; Neumann et al., 2018; Panza et al., 2018; Scott et al., 2016; Yan and Vassar, 2014a), repurposing these BACE1 inhibitors for the macrophage-based tumor immunotherapy will provide important therapy for cancer.

The molecular mechanisms underlying the polarization and maintenance of M1 and M2 macrophages were poorly understood. In this Example, we interrogated the molecular signaling that regulates the polarization of M2/M1 TAMs, and found that BACE1 disruption or inhibition attenuates the STAT3 activating phosphorylation in M2 macrophages and promotes the M2 to M1 transition of TAMs. Moreover, ectopic expression of a constitutively activated STAT3 (STAT3-C) rescued the effect caused by BACE1 disruption or inhibition, indicating that BACE1-mediated STAT3 activation is required for the polarization and maintenance of M2 TAMs. Our in vivo study further demonstrated that inhibiting BACE1 by MK-8931 treatment suppressed STAT3 activation in TAMs, resulting in reduction of M2 TAMs and increase of M1 TAMs as well as enhanced macrophage phagocytosis to effectively inhibit tumor growth.

STAT3 is a critical transcription factor that plays multiple roles in tumor development and malignant progression (Yu et al., 2009). Previous studies demonstrated that STAT3 hyper-activation mediated by the bone marrow X-linked kinase (BMX) is required for maintaining the self-renewal and tumorigenic potential of GSCs in GBM (Guryanova et al., 2011; Shi et al., 2018). In this Example, we found that STAT3 activation in M2 TAMs is regulated by BACE1. Previous studies uncovered that GSCs secreted Periostin to recruit monocyte-derived TAMs into GBM tumors (Zhou et al., 2015). In turn, TAMs (M2) support the maintenance of GSCs through PTN-PTPRZ1 signaling in GBM (Shi et al., 2017a). Because GSCs play crucial roles in tumor growth and malignant progression including invasion, angiogenesis, pericyte generation, BTB formation, and therapeutic resistance, the indirect reduction of GSCs caused by the decreased M2 TAMs induced by BACE1 inhibition with MK-8931 treatment may also partially contribute to the suppression of tumor growth in vivo.

Our preclinical studies demonstrated that pharmacological inhibition of BACE1 by MK-8931 potently redirected M2 TAMs into M1 macrophages to promote their phagocytosis against cancer cells in GBM tumors and brain metastases of lung ADC. Infiltrated TAMs are usually educated by cancer cells to become "friends" of tumors to support malignant progression, but targeting BACE1 by MK8931 turns these TAMs into "enemies" of cancer cells to suppress tumor growth. MK-8931 was initially developed as BACE1 inhibitor for AD treatment (Scott et al., 2016). Clinical trials (Phase I to Phase III) have demonstrated MK-8931 was well-tolerated in human and showed little toxic effect during the trials (Egan et al., 2018; Egan et al., 2019). Importantly, MK-8931 has been shown to penetrate the BBB very well (Kennedy et al., 2016). Our preclinical results demonstrated that MK-8931 treatment potently inhibited tumor grow of GBM tumors and brain metastases of lung ADC, supporting that MK-8931 has good BBB or BTB permeability to enter brain tumors. Thus, MK-8931 can be repurposed to be a potent drug for promoting TAM phagocytosis against tumor cells to improve immunotherapy for many types of malignant tumors including GBM and brain metastases of other cancers.

To enhance the therapeutic efficacy of MK-8931, we found that low dose of irradiation (IR) remarkably augmented TAM infiltration and effectively synergized with MK-8931. Although IR could eliminate a majority of cancer cells in some types of tumors, IR often triggers inflammation response in tumor and induces therapeutic resistance (Barker et al., 2015; Ruffell and Coussens, 2015). Thus, IR remodels the tumor microenvironment and changes the population of infiltrating immune cells to mediate resistance (Barker et al., 2015). This Example demonstrated that low dose of IR markedly enhanced TAM infiltration into GBM tumors. Surprisingly, the increased TAMs induced by low dose of IR in tumors were mainly M2 TAMs, although a previous in vitro study showed that IR can induce polarization of human and murine monocytes toward M1 macrophages (Genard et al., 2017). It is possible that IR affects macrophages in vitro and in vivo in different manner and the low and high doses of IR differentially impact macrophage polarization. Interestingly, another study showed that IR could induce BACE1 expression (Lee et al., 2012), which should promote the maintenance of M2 TAMs. Our in vivo studies clearly demonstrated low dose of IR dramatically increased M2 TAM density in the tumor. Although treatment with low dose of IR alone did not significantly impact tumor growth, it provides a powerful tool to enhance TAM infiltration into tumors, which allows MK-8931 treatment to redirect the increased M2 TAMs into more M1 macrophages to better suppress tumor growth. Thus, MK-8931 treatment overcomes the drawback of IR that may increase tumor-supportive M2 TAMs. The combination of low dose of IR with MK-8931 treatment clearly resulted in enhanced anti-tumor efficacy. This therapeutic strategy is particularly important for those solid tumors containing relatively less TAMs. Most malignant tumors contain abundant TAMs and the treatment with MK-8931 alone should effectively promote phagocytosis of enough TAMs to eliminate cancer cells, but certain types of tumors in some patients may have less TAMs. In either situation, the combination of MK-8931 treatment with low dose of IR should enhance the therapeutic efficacy. Because some tumors may not contain enough infiltrating T cells to facilitate the current immunotherapy with immune checkpoint inhibitors such as anti-PD1 antibody, the combination of low dose of IR with MK-8931 treatment should provide an alternative effective therapeutics to overcome the poor response of some malignant tumors to current immunotherapy.

Tumor immunotherapy has shown promising, but the majority of solid tumors respond very poorly to current immune checkpoint blockage and CAR-T therapy partially due to the insufficient T cell infiltration into tumors and poor delivery of the checkpoint inhibitors such as anti-PD1 antibody to tumor tissues. As most malignant tumors contain abundant TAMs, and we have identified an effective way using low dose of radiation to enhance macrophage infiltration into tumors, this macrophage-based tumor immunotherapy using small molecular modulators such as MK-8931 may have several advantages. (1) This new immunotherapy reprograms M2 TAMs into tumor-suppressive M1 macrophages, it not only reduces tumor-supportive TAMs but also promotes macrophage phagocytosis against cancer cells. The double 'hits" of this therapy effectively suppress tumor growth and malignant progression. (2) As current tumor immunotherapy such as CAR-T and anti-PD1 is too expensive for most patients, using the small molecule modulators to facilitate the immunotherapy will provide a much more economic but effective approach to improve tumor control and survival of cancer patients. (3) Because BACE1 inhibition by MK-8931 potently redirects the tumor-supportive M2 TAMs into tumor-suppressive macrophages, this therapy should effectively re-modulate the tumor immune microenvironment to overcome the resistance to other therapies. (4) As low dose of radiation markedly enhances TAM infiltration and synergizes with BACE1 inhibition by MK-8931, the combined therapy can be broadly used for the macrophage-based immunotherapy for most malignant tumors containing abundant or less TAMs. (5) Because all BACE1 inhibitors including MK-9831 developed for AD clinical trials display great ability to penetrate the BBB or BTB, this macrophage-based immunotherapy activated by BACE1 inhibitors will overcome the BBB or BTB issue that negatively impacts other therapies including anti-PD1 treatment in brain tumors including brain metastases that lack effective therapeutic option. (6) As BACE1 inhibition by MK-8931, AZD3293, E2609, or CNP520 has been shown to be very safe for patients in the AD clinical trials (Cebers et al., 2017; Egan et al., 2018; Egan et al., 2019; Eketjall et al., 2016; Kennedy et al., 2016; Lopez Lopez et al., 2017; Neumann et al., 2018; Scott et al., 2016), and we have demonstrated that targeting BACE1 by these inhibitors promotes macrophage phagocytosis against cancer cells, repurposing these BACE1 inhibitors for the macrophage-based tumor immunotherapy should be useful.

Methods

TABLE 2

RESOURCES TABLE

| REAGENT or RESOURCE | SOURCE | IDENTIFIER |
|---|---|---|
| Antibodies | | |
| ARG1 | BD Biosciences | Cat# 610708; RRID: AB_398031 |
| BACE1 | ThermoFisher | Cat# MA1-177; RRID: AB_2608440 |
| BACE1 | Abcam | Cat# ab183612 |
| BACE1 | Santa Cruz | Cat# sc-33711; RRID: AB_626716 |
| CD11b | Bio-Rad | Cat# MCA711GT; RRID: AB_1100616 |
| CD11c | BD Biosciences | Cat# 558079; RRID: AB_647251 |
| CD163 | Santa Cruz | Cat# sc-33560; RRID: AB_2074556 |
| CD163 | Santa Cruz | Cat# sc-33715; RRID: AB_626932 |
| CD163 | Santa Cruz | Cat# sc-18795 |
| CD31 | DAKO | Cat# M0823, RRID: AB_2114471 |
| CD31 | Bethyl | Cat# IHC-00055, RRID: AB_2114469 |
| Cleaved caspase 3 | Cell Signaling | Cat# 9661; RRID: AB_2341188 |
| FIZZ1 | Abcam | Cat# ab39626; RRID: AB_777652 |
| FLAG | Sigma-Aldrich | Cat# SAB4200071; RRID: AB_10603396 |
| GAPDH | Cell Signaling | Cat# 2118; RRID: AB_561053 |
| GLUT1 | ThermoFisher | Cat# RB-9052-P; RRID: AB_177893 |
| HLA-DR | Abcam | Cat# ab20181; RRID: AB_445401 |
| HLA-DR | Biolegend | Cat# 307602; RRID: AB_314680 |
| IBA1 | Abcam | Cat# ab5076; RRID: AB_2224402 |
| IBA1 | Wako Chemicals | Cat# 019-19741; RRID: AB_839504 |
| IL10 | R&D Systems | Cat# AF-519; RRID: AB_355408 |
| IL1β | R&D Systems | Cat# AF-401; RRID: AB_416684 |
| iNOS | BD Biosciences | Cat# 610328; RRID: AB_397718 |
| Ki67 | Abcam | Cat# ab15580; RRID: AB_443209 |
| PARP | Cell Signaling | Cat# 9542; RRID: AB_2160739 |
| pSTAT3 (Tyr705) | Cell Signaling | Cat# 9131; RRID: AB_331586 |
| pSTAT6 (Tyr641) | Cell Signaling | Cat# 9361; RRID: AB_331595 |
| SOX2 | Bethyl | Cat# A301-739A; RRID: AB_1211354 |
| STAT3 | Cell Signaling | Cat# 9139; RRID: AB_331757 |
| STAT6 | Cell Signaling | Cat# 5397; RRID: AB_11220421 |
| TGFβ | R&D Systems | Cat# MAB1835; RRID: AB_357931 |
| TNFα | Abcam | Cat# ab6671; RRID: AB_305641 |

TABLE 2-continued

RESOURCES TABLE

| REAGENT or RESOURCE | SOURCE | IDENTIFIER |
|---|---|---|
| TRA-1-85 | R&D Systems | Cat# MAB3195; RRID: AB_2066681 |
| Alexa Fluor® 488-conjugated donkey anti-mouse IgG | Invitrogen | Cat# A-21202: RRID: AB_141607 |
| Alexa Fluor® 568-conjugated donkey anti-mouse IgG | Invitrogen | Cat# A-10037; RRID: AB_2534013 |
| Alexa Fluor® 488-conjugated donkey anti-rabbit IgG | Invitrogen | Cat# A-21206; RRID: AB_141708 |
| Alexa Fluor® 568-conjugated donkey anti-rabbit IgG | Invitrogen | Cat# A-10042; RRID: AB_2534017 |
| Alexa Fluor® 488-conjugated donkey anti-goat IgG | Invitrogen | Cat# A-11055; RRID: AB_142672 |
| Alexa Fluor® 568-conjugated donkey anti-goat IgG | Invitrogen | Cat# A-11057; RRID: AB_142581 |
| Alexa Fluor® 594-conjugated donkey anti-rat IgG | Invitrogen | Cat# A-21209; RRID: AB_2535795 |
| Alexa Fluor® 488-conjugated goat anti-rabbit IgG | Invitrogen | Cat# A-11008: RRID: AB_143165 |
| Alexa Fluor® 568-conjugated goat anti-Armenian Hamster IgG | Abcam | Cat# AB_175716 |
| Anti-mouse IgG, HRP-linked antibody | Cell Signaling | Cat# 7076; RRID: AB_330924 |
| Anti-rabbit IgG, HRP-linked antibody | Cell Signaling | Cat# 7074; RRID: AB_2099233 |
| Anti-goat IgG, HRP-linked antibody | Santa Cruz | Cat# sc-2354; RRID: AB_628490 |
| Anti-mouse IgG, Biotinylated antibody | Vector Laboratories | Cat# BA-9200; RRID: AB_2336171 |
| Anti-rabbit IgG, Biotinylated antibody | Vector Laboratories | Cat# BA-1000; RRID: AB_2313606 |
| Anti-goat IgG, Biotinylated antibody | Vector Laboratories | Cat# BA-9500; RRID: AB_2336123 |
| Bacterial and Virus Strains | | |
| pCDH cDNA cloning and expression Lenti vectors | SBI | N/A |
| Chemically Competent E. coli | ThermoFisher | Cat# C737303 |
| Biological Samples | | |
| Human primary GBM tumor samples | The Brain Tumor and Neuro-Oncology Centers at Cleveland Clinic | N/A |
| Human lung cancer brain metastases tumor samples | The Brain Tumor and Neuro-Oncology Centers at Cleveland Clinic | N/A |

TABLE 2-continued

RESOURCES TABLE

| REAGENT or RESOURCE | SOURCE | IDENTIFIER |
|---|---|---|
| Xenografts of human GBM tumor (T4121) | Derived by our laboratory | N/A |
| Xenografts of human GBM tumor (T387) | Derived by our laboratory | N/A |
| Xenografts of human lung cancer brain metastases (H1002) | Derived by our laboratory | N/A |
| Chemicals, Peptides, and Recombinant Proteins | | |
| BMP4 | Abcam | Cat# ab87063 |
| CellTracker™ CMFDA Dye | ThermoFisher | Cat# C2925 |
| DAPI | Cell Signaling | Cat# 4083 |
| Dimethylsulfoxide (DMSO) | Santa Cruz | Cat# sc-358801 |
| D-Luciferin | GoldBio | Cat# LUCK-10G |
| Etoposide | Santa Cruz | Cat# sc-3512B |
| H2O2 | Sigma-Aldrich | Cat# H1009 |
| Hematoxylin | Fisher Scientific | Cat# 22-220-102 |
| Methyl cellulose | Sigma-Aldrich | Cat# M0512 |
| MK-8931 (Verubecestat) | SelleckChem | Cat# S8173 |
| MK-8931 (Verubecestat) | MedKoo | Cat# 331024 |
| M-MLV Reverse Transcriptase | Promega | Cat# PR-M1701 |
| Neomycin | Santa Cruz | Cat# SC-29065A |
| OCT compound | VWR | Cat# 25608-930 |
| PFA | Electron Microscopy Sciences | Cat# 15714 |
| Phorbol 12-myristate 13-acetate | Sigma-Aldrich | Cat# P1585 |
| PhosStop inhibitor | Roche | Cat# 04906837001 |
| Polybrene | Sigma-Aldrich | Cat# H9268-5G |
| Protease inhibitor | Roche | Cat# 04693159001 |
| Protein Assay Dye | Bio-Rad | Cat# 5000006 |
| Puromycin | Fisher Scientific | Cat# BP2956100 |
| Recombinant Human bFGF | R&D Systems | Cat# 4114-TC-01M |
| Recombinant Human EGF | GoldBio | Cat# 1150-04-100 |
| Recombinant Human IL10 | Peprotech | Cat# 200-10 |
| Recombinant Human IL3 | Biolegend | Cat# 578006 |
| Recombinant Human IL4 | Peprotech | Cat# 200-04 |
| Recombinant Human M-CSF | Biolegend | Cat# 574806 |
| Recombinant Human SCF | Peprotech | Cat# 300-07 |
| Recombinant Human TGFβ | Peprotech | Cat# 200-21 |
| Recombinant Human VEGF | Peprotech | Cat# 100-20 |
| Triton X-100 | Bio-Rad | Cat# 1610407 |
| Y27632 | SelleckChem | Cat# S1049 |
| β-Mercaptoethanol | ThermoFisher | Cat# 21985023 |
| Commercial Assays | | |
| Antigen Unmasking Solutions | Vector Laboratories | Cat# H-3300 |
| Cell Viability Assay Kit | Promega | Cat# G7570 |
| DAB Substrate Kit | Vector Laboratories | Cat# SK-4100 |
| Mouse cell depletion kit | Miltenyi Biotec | Cat# 130-104-694 |
| Mycoplasma Detection Kit | ThermoFisher | Cat# M7006 |
| Papain Dissociation System | Worthington Biochemical | Cat# LK003150 |
| PCR Purification Kit | QIAGEN | Cat# 28106 |
| Plasmid miniprep kit | QIAGEN | Cat# 27104 |
| PureLink™ RNA Kit | ThermoFisher | Cat# 12183020 |

TABLE 2-continued

RESOURCES TABLE

| REAGENT or RESOURCE | SOURCE | IDENTIFIER |
|---|---|---|
| qPCR Kit | Alkali Scientific | Cat# QS2050 |
| Western Bright ECL | Advansta | Cat# K-12045-D50 |

Experimental Models: Cell Lines

| | | |
|---|---|---|
| Human iPS cell | ALSTEM | Cat# iPS11 |
| Monocytes and macrophages derived from human iPS cell | Derived by our laboratory | N/A |
| BMDMs | Derived by our laboratory | N/A |
| H1002 | Derived by our laboratory | N/A |
| Lenti-X™ 293T Cell | Clontech | Cat# 632180 |
| T387 | Derived by our laboratory | N/A |
| T4121 | Derived by our laboratory | N/A |
| U937 | ATCC | Cat# CRL-1593.2 |

Experimental Models: Organisms/Strains

| | | |
|---|---|---|
| NSG mice (NOD.Cg-Prkdc$^{scid}$Il2rg$^{tm1Wjl}$/SzJ) | Jackson Laboratories | Cat# 005557 |

Oligonucleotides

| | | |
|---|---|---|
| Primer: BACE1 Forward: GCAGGGCTAC TACGTGGAGA (SEQ ID NO: 1) | — | N/A |
| Primer: BACE1 Reverse: GTATCCACCAG GATGTTGAGC (SEQ ID NO: 2) | — | N/A |
| Primer: GAPDH Forward: AAGGTGAAGGT CGGAGTCAAC (SEQ ID NO: 3) | — | N/A |
| Primer: GAPDH Reverse: GGGGTCATTGA TGGCAACAATA (SEQ ID NO: 4) | — | N/A |
| Primer: tdTomato Forward: GCTAGCCCAAT CATTTAAATAT AACTT (SEQ ID NO:5) | — | N/A |
| Primer: tdTomato Reverse: GCGGCCGCTT ACTTGTACAG CTCGTCCATGC (SEQ ID NO:6) | — | N/A |
| Recombinant DNA | | |
| ps-PAX2 | Addgene | Cat# 12260 |
| pCI-VSVG | Addgene | Cat# 1733 |
| Lentivirus vectors | SBI | Cat# CD511B-1, Cat# CD514B-1 |
| pCDH-EF1-Luc2-P2A-tdTomato | Addgene | Cat# 72486 |
| pCDH-tdTomato | This paper | N/A |
| pLKO-NT shRNA | Sigma-Aldrich | Cat# SHC002 |
| pLKO-shBACE1#1 | Sigma-Aldrich | Cat# TRCN0000000277 |
| pLKO-shBACE1#2 | Sigma-Aldrich | Cat# TRCN0000000279 |

TABLE 2-continued

RESOURCES TABLE

| REAGENT or RESOURCE | SOURCE | IDENTIFIER |
|---|---|---|
| pCDH-Luciferase | Zhou et al., 2015 | N/A |
| pLSTAT3-C-Flag | Guryanova et al., 2011 | N/A |
| Software and Algorithms | | |
| ImageJ | NIH | https://imagej.nih.gov/ |
| Prism 5 | GraphPad | https://www.graphpad.com/ |
| LAS software | Leica | https://www.leica-microsystems.com/ |
| Image Lab | Bio-Rad | http://wwiv.bio-rad.com/ |
| In Vivo Imaging Software | PerkinElmer | https://www.perkinelmer.com/ |
| GlioVis | Bowman et al., 2017 | http://gliovis.bioinfo.cnio.es/ |
| Microsoft Office | Microsoft Corporation | http://www.office.com/ |
| Other | | |
| Accutase | BioExpress | Cat# S-1100 |
| Antibiotic-antimycotic | ThermoFisher | Cat# 15240062 |
| B-27 | ThermoFisher | Cat# 12587010 |
| BSA | Sigma-Aldrich | Cat# A7906 |
| Fetal bovine serum | ThermoFisher | Cat# 10437-036 |
| Glutamax | ThermoFisher | Cat# 35050061 |
| mTeSR1 medium | StemCell Technologies | Cat# 85850 |
| Neurobasal medium | Invitrogen | Cat# 12349015 |
| Non-essential amino acids | ThermoFisher | Cat# 11140050 |
| Sodium pyruvate | ThermoFisher | Cat# 11360070 |
| X-VIVO™ 15 medium | Lonza | Cat# 04-418Q |

Experimental Model and Subject Details

Cells

Cells were cultured in a humidified incubator at 37° C. with 5% $CO_2$ and atmospheric oxygen. All cells used in this study were consistently confirmed to be free from *Mycoplasma* by using a MycoFluor™ *Mycoplasma* Detection Kit (ThermoFisher, M7006). 293FT cells were from Clontech (632180) and maintained in the DMEM medium supplemented with 10% (v/v) fetal bovine serum (FBS, ThermoFisher, 10437-036). Human iPSCs were from ALSTEM (iPS11) and grown in the mTeSR1 medium (StemCell Technologies, 85850). Human iPSC-derived monocytes and macrophages were maintained in the X-VIVO™ 15 medium (Lonza, 04-418Q). Human U937 cells were from ATCC (CRL-1593.2™) and maintained in the RPMI 1640 medium with 10% (v/v) FBS. Bone-marrow derived macrophages (BMDMs) were generated in our own lab with an established protocol (Weischenfeldt and Porse, 2008) and cultured in the RPMI 1640 medium with 10% (v/v) FBS. Human GSCs (T4121 and T387) were derived from primary GBMs (Cheng et al., 2013; Fang et al., 2017; Shi et al., 2018; Wang et al., 2018; Xie et al., 2018) and maintained in the Neurobasal medium (Invitrogen, 12349015) supplemented with B-27 (Invitrogen, 12587010), glutamine (2 mM, ThermoFisher, 35050061), non-essential amino acids (ThermoFisher, 11140050), sodium pyruvate (1 mM, ThermoFisher, 11360070), epidermal growth factor (EGF, 20 ng/mL, Goldbio, 1150-04-100), and basic fibroblast growth factor (bFGF, 20 ng/mL, R&D Systems, 4114-TC-01M). Human lung cancer cells (H1002) were derived from brain metastases of lung adenocarcinoma (ADC) and maintained in the stem cell medium. Unless otherwise indicated, the Gibco® antibiotic-antimycotic (ThermoFisher, 15240062) was used to prevent contamination in all the media.

Human Surgical Specimens

Surgical specimens of human GBMs and brain metastases of lung ADC were collected from the Brain Tumor and Neuro-Oncology Center Cleveland Clinic according to an approved protocol by the Cleveland Clinic Institutional Review Broad. Human GBM surgical specimens were used for isolation of GSCs and immunofluorescent analyses. Human lung ADC brain metastases were used for isolation of lung cancer cells for establishing the intracranial xenografts for the study.

Mice

All animal experiments were performed in accordance with protocols approved by the IACUC at the Cleveland Clinic Lerner Research Institute. NSG mice (NOD.Cg-Prkdc$^{scid}$Il2rg$^{tm1Wjl}$/SzJ) were randomly selected and used for establishing GBM xenografts or intracranial xenografts of lung ADC for the in vivo studies. Mice were maintained in a 14 hours light/10 hours dark cycle, and provided with sterilized water and food ad libitum at the Biological Resource Unit of the Cleveland Clinic Lerner Research Institute.

Chemicals and Reagents

MK-8931 was purchased from Selleckchem (S8173) and Medkoo (331024), dissolved at a concentration of 100 mg/mL in dimethyl sulphoxide (DMSO, Santa Cruz, sc-358801) as a stock solution, and stored at −20° C. until use. D-Luciferin was bought from GoldBio (LUCK-10G), prepared at a concentration of 15 mg/mL in sterile water as a stock solution, and stored at −20° C. until use. Etoposide (sc-3512B) was from Santa Cruz, prepared at a concentration of 1 mM in DSMO, stored at −20° C. until use. 32% Paraformaldehyde (PFA, 15714) was from Electron Microscopy Sciences and diluted to 4% with PBS before use. Protease (04693159001) and phosphatase inhibitors (04906837001) tablets were from Roche. Recombinant Human SCF (300-07), VEGF (100-20), IL4 (200-04), IL10 (200-10), and TGFβ (200-21) were from Peprotech. Recombinant Human M-CSF (574806) and IL3 (578006) were from Biolegend. Recombinant Human bFGF was from R&D Systems (4114-TC-01M). Recombinant Human EGF was from GoldBio (1150-04-100). With the manufacture's instruction, all the recombinant proteins were prepared at a 1,000× concentration as a stock solution and stored at −80° C. until use. The other chemicals and reagents otherwise indicated were purchased from sigma-Aldrich.

Methods Details

Derivation of Monocytes and Macrophages from Human iPS Cells (iPSCs)

Human iPSC-derived monocytes and macrophages were prepared in accordance with an established protocol (Mia et al., 2014; Shi et al., 2017a; van Wilgenburg et al., 2013). To generate GFP$^+$ iPSCs, human iPSCs were seeded in a 10-cm tissue culture dish and transduced with GFP through lentiviral infection for 12 hours. Two days post infection, GFP$^+$ iPSCs were selected and maintained in the mTeSR1 medium (Lonza) for the differentiation experiment. To induce the formation of the embryoid bodies (EBs), GFP$^+$ iPSCs were seeded on an ultra-low attachment plate (Costar, 7007) in 100 μL of the mTeSR™1 medium supplemented with BMP4 (50 ng/mL, Abcam, ab87063), SCF (20 ng/mL, Peprotech, 300-07), Y27632 (50 μM, SellckChem, S1049), and VEGF (20 ng/mL, Peprotech, 100-20). The 96-well ultra-low attachment plate was centrifuged at 800 rpm for three minutes and the plate was placed into the incubator and left for four days. At day 2, 50 μL of culture medium in the well was aspirated and replaced by 50 μL of fresh mTeSR™1 medium containing the above inducers. For monocyte differentiation, about ten EBs were transferred to each well of a six-well tissue culture plate and cultured in the X-VIVO™ 15 medium (Lonza, 04-418Q) supplemented with IL3 (25 ng/mL, Biolegend, 578006), M-CSF (100 ng/mL, Biolegend, 574806), glutamine (2 mM, ThermoFisher, 35050061), and β-mercaptoethanol (0.055 M, ThermoFisher, 21985023) for two weeks. The medium was changed every 5 days. Once monocytes were visible in the supernatant of the cultures, non-adherent monocytes were harvested. For macrophage differentiation, the iPSC-derived monocytes (1.5× $10^5$) were plated on each well of 6-well plates and cultured in the X-VIVO™ 15 medium with M-CSF (100 ng/mL, Biolegend, 574806) for six days. For M2 macrophages differentiation, the iPSC-derived monocytes were seeded on each well of 6-well plates and primed by treatment with phorbol 12-myristate 13-acetate (PMA, 5 nM) for two days to produce the M0 macrophage. The M0 macrophages were further treated with IL4 (20 ng/mL, Peprotech, 200-04), IL10 (20 ng/mL, Peprotech, 200-10), and TGFβ (20 ng/mL, Peprotech, 200-21) for three days to generate the M2 macrophages.

Preparation of Bone Marrow-Derived Monocytes (BMDMs)

BMDMs were isolated and cultured according to an established protocol (Weischenfeldt and Porse, 2008). In brief, mouse bone marrow cells were collected by flushing the femurs and tibias with sterile PBS and then treated by red blood cell lysis buffer to remove red blood cells. The cells were re-suspended and cultured in the RPMI 1640 medium with 10% FBS and M-CSF (100 ng/mL) for seven days to differentiate into BMDMs.

Screening for Potential Drugs to Activate Macrophage Phagocytosis

To screen for potential small molecules activating phagocytosis of iPSC-derived M2 macrophages against human cancer cells, GFP$^+$ iPSC-derived M2 macrophages ($5\times10^4$ cells) were seeded in each well of 24-well plates and treated by small molecules for two days. After washing, the cells were maintained in the RPMI 1640 medium for two hours. Next, tdTomato-expressing glioma cells (T4121) or lung ADC cancer cells ($2\times10^5$) were added to each well and co-incubated with the M2 macrophages in the RPMI 1640 medium with 10% FBS for another two hours. After the co-incubation, co-cultures were washed three times with the warm RPMI 1640 medium to remove free cancer cells and images were captured with a fluorescent microscope. The phagocytosis was measured as the number of inclusion bodies of cancer cells (in red) within macrophages (in green).

To detect the MK-8931-activated phagocytosis of bone marrow-derived macrophages (BMDMs) against human cancer cells, BMDMs were pre-stained by the CellTracker™ Green CMFDA Dye (1 μM, ThermoFisher, C2925). BMDMs ($5\times10^4$ cells) were seeded in each well of a 24-well plate and treated by DMSO (Control) or MK-8931 (50 μg/mL) for two days. After washing, the BMDMs were maintained in the RPMI 1640 medium for two hours. Next, tdTomato-expressing T4121 GSCs ($2\times10^5$ cells) were added to each well and co-incubated with BMDMs in the RPMI 1640 medium with 10% FBS for another two hours. After co-incubation, the co-cultures were extensively washed several times with the warm RPMI 1640 medium to remove free cancer cells and the images were captured with a fluorescent microscope.

Plasmids for Overexpression or Knockdown

To create pCDH-tdTomato vector, the full-length tdTomato was amplified from the pCDH-EF1-Luc2-P2A-tdTomato (Addgene, 72486) vector with the following primers: Forward: 5'-GCT AGC CCA ATC ATT TAA ATA TAA CTT-3' (SEQ ID NO:5), Reverse: 5'-GCG CCG CTA C TTG TAC AGC TCG TCC ATG C-3' (SEQ ID NO:6), and then cloned into the pCDH-CMV-MCS-EF1α-Neo vector at Nhe1 and Not1 sites. The sequence of inserted tdTomato was confirmed by DNA sequencing. The constitutively active STAT3 (STAT3-C-Flag) and pCDH-luciferase constructs were generated in our own lab (Guryanova et al., 2011; Zhou et al., 2015). The shRNAs against BACE1 (shBACE1) or non-targeting sequence (NT) were purchased from Sigma-Aldrich. The lentivirus packaging vectors (ps-PAX2 and pCI-VSVS) were from Addgene.

Isolation of Lung Cancer Cells from Brain Metastases of Lung ADC

Lung cancer cells were isolated from brain metastases of human lung ADC by using the Papain Dissociation System (Worthington Biochemical, LK003150) according to the manufacturer's instructions. Briefly, the brain metastatic tumor of lung ADC was cut into tiny chunks and gently rinsed with the iced Sterile Earle's Balanced Salt Solution (EBSS) medium. After removing the necrotic tissues and blood, the chunks were further minced into slurry and then treated by papain in the incubator to dissociate single lung cancer cells. The isolated lung cancer cells were maintained in the stem cell medium and used for establishing the patient-derived xenografts (PDXs). The lung cancer cells were further isolated from the xenografts by using the Papain Dissociation System (Worthington Biochemical). To avoid any mouse cell contamination, the isolated cells from the xenografts were subjected to a Mouse Cell Depletion Kit (Miltenyi Biotec, 130-104-694). The isolated lung cancer cells from a PDX line (H1002) were maintained in the stem cell medium and used for experiments in this study.

Production of Lentiviruses

Lentiviruses for expression of shRNAs (shBACE1) or overexpression of an ectopic protein (STAT3-C) were produced in 293FT cells and prepared as previously described (Fang et al., 2017; Shi et al., 2018; Shi et al., 2017a; Shi et al., 2017b; Zhou et al., 2017). Briefly, 293FT cells (Clontech, 632180) were co-transduced with targeting plasmids and packaging vectors pCI-VSVG (Addgene, 1733) and ps-PAX2 (Addgene, 12260) by using calcium phosphate. Four days after transfection, the supernatants were harvested and virus titer was determined as described previously (Guryanova et al., 2011; Li et al., 2009). For infection, cells were treated by lentivirus at a multiplicity of infection (MOI) of 1.

Generation of Stable Cell Lines

For the generation of the tdTomato-expressing stable glioma cells, GSCs (T4121) were transduced with tdTomato through lentiviral infection for 12 hours. Two days post infection, cells were treated with neomycin (500 µg/mL, Santa Cruz, sc-29065A) for seven days to select stable clones. The expression of tdTomato was confirmed under a fluorescence microscopy. To generate the luciferase-expressing stable glioma cells, GSCs (T4121 or T387) were transduced with firefly luciferase through lentiviral infection for 12 hours. Two days post infection, cells were treated with puromycin (2 µg/mL, Fisher Scientific, BP2956100) for seven days to select stable clones. The luciferase activity was confirmed by the Luciferase Assay System (Promega, E1500).

To establish the stable U937 cells expressing shBACE1 or shNT, U937 cells were transduced with shBACE1 or shNT expression through lentiviral infection. Two days post infection, cells were treated with puromycin (2 µg/mL) for seven days to select stable clones. Immunoblot was used to test the knockdown efficacy of BACE1 in the U937 stable cells.

Derivation of M2 Macrophages from U937 Cells

The U937-derived M2 macrophages were prepared according to an established protocol (Mia et al., 2014; Shi et al., 2017a). In brief, U937 cells grown in a 10-cm tissue culture dish were primed by PMA (5 nM) for two days to produce M0 macrophages. Then the M0 macrophages were further induced by IL4 (20 ng/mL, Peprotech, 200-04), IL10 (20 ng/mL, Peprotech, 200-10), and TGFβ (20 ng/mL, Peprotech, 200-21) for three days to generate M2 macrophages.

RNA Isolation and RT-PCR

Total RNA was isolated from cells by using the PureLink™ RNA Kit (ThermoFisher, 12183020) and reversely transcribed into cDNA with M-MLV reverse transcriptase (Promega, PR-M1701). Real-time PCR (qPCR) was performed on an ABI 7500 Real-Time PCR System (Applied Biosystems) using the SYBR-green qPCR Kit (Alkali Scientific, QS2050). Expression values were normalized to GAPDH. Gene-specific primers were as follows: BACE1 (forward): 5'-GCA GGG CTA CTA CGT GGA GA-3' (SEQ ID NO:1), BACE1 (reverse): 5'-GTA TCC ACC AGG ATG TTG AGC-3'; GAPDH (forward; SEQ ID NO:2): 5'-AAG GTG AAG GTC GGA GTC AA C-3', GAPDH (reverse; SEQ ID NO:3) 5'-GGG GTC ATT GAT GGC AAC AAT A-3' (SEQ ID NO:4).

Establishment of Intracranial Xenografts of GBM or Lung ADC and Drug Treatment

To establish xenografts for in vivo studies, intracranial transplantation of glioma or lung cancer cells into brains of NSG mice were performed as described previously (Bao et al., 2006a; Fang et al., 2014; Fang et al., 2017; Shi et al., 2017a; Shi et al., 2017b; Zhou et al., 2015). In brief, GSCs (T4121 and T387) or lung ADC cells (H1002) expressing luciferase were injected into the right cerebral cortex at a depth of 3.5 mm. Seven days after the implantation, IVIS was performed twice per week to monitor the tumor growth under the Spectrum CT Imaging System (PerkinElmer) before and after treatment. Stock solution of MK-8931 at 100 mg/mL in DMSO was diluted in the 0.5% (w/v) methylcellulose (Sigma-Aldrich, M0512) to the concentration of 6 mg/mL as reported (Kennedy et al., 2016). The mice bearing the xenografts were treated with MK-8931 (30 mg/kg) or the control (DMSO) once daily by oral gavage for two weeks or until the humane endpoint. Mouse brains bearing the tumors were collected for immunofluorescent, histochemical and histological analyses. To collect mouse brain bearing the tumors, cardiac perfusion with PBS and the following 4% PFA (Electron Microscopy Sciences, 15714) was performed.

Irradiation on Intracranial Xenografts

Irradiation (IR) was performed with the Pantek X-ray irradiator (once per week) at low dose (2 Gy). To protect the mice and limit the side effect of irradiation, anesthetized mice were covered by a lead plate and only the tumor implantation sites were exposed to the fractioned radiation. Mice were sacrificed at the indicated time points or upon the appearance of the neurological signs. Mouse brains bearing the tumors were collected for further analyses through cardiac perfusion with PBS and the following 4% PFA (Electron Microscopy Sciences, 15714). Only animals with accidental death (for example, due to infection or intracranial injection) were excluded from the data analysis.

Immunofluorescent Analysis

Immunofluorescence staining of tumor tissues or cells were performed as described in our previous publications (Bao et al., 2006a; Cheng et al., 2013; Fang et al., 2017; Shi et al., 2017a; Zhou et al., 2015). In brief, tumor sections or cells were fixed with 4% PFA for ten minutes, washed three times with cold PBS for five minutes each, permeabilized by 0.5% (v/v) triton X-100 (Bio-Rad, 1610407) for ten minutes, and blocked with 3% (w/v) BSA (Sigma-Aldrich, A7906) in PBS for one hour at room temperature. For Ki67 and pSTAT3 staining, antigen retrieval was performed by incubating the sections in boiled antigen retrieval buffer (Vector Laboratories, H-3300) for 15 minutes before permeabilization. Primary antibodies were added to the sections or cells and incubated overnight at 4° C. Primary antibodies used for immunofluorescence in this study were diluted as described below: anti-BACE1 (Abcam, ab183612, 1:50; Thermo Fisher Scientific, MA1-177, 1:50), anti-IBA1 (Abcam, ab5076, 1:200; Wako chemicals, 019-19741, 1:200), anti-CD11b (Bio-Rad, MCA711GT, 1:100), anti-FIZZ1 (Abcam, ab39626, 1:100), anti-CD163 (Santa Cruz, sc-33560 and sc-33715, 1:100), anti-ARG1 (BD Biosciences, 610708, 1:300), anti-HLA-DR (Biolegend, 307602, 1:100), anti-CD11c (BD Pharmingen, 558079, 1:100), anti-TRA-1-85 (RD System, MAB3195, 1:300), anti-CD31 (Dako, M082301, 1:100), anti-cleaved caspase 3 (Cell signaling, 9661, 1:100), anti-GLUT1 (ThermoFisher, PA1-37782, 1:200), anti-Ki67 (Abcam, ab15580, 1:100), anti-SOX2 (Bethyl laboratory, A301-739A, 1:200), and anti-pSTAT3 (Tyr705) (Cell signaling, 9131, 1:100). After the incubation of the primary antibodies, the sections or cells were washed three times with cold PBS for five minutes each and then incubated with the secondary antibodies for one hour at room temperature. The secondary antibodies used in this Example included Alexa Fluor® 488 Donkey Anti-Mouse IgG (Invitrogen, A-21202, 1:200), Alexa Fluor® 568 Donkey Anti-Mouse IgG (Invitrogen, A-10037, 1:200), Alexa Fluor® 488 Donkey Anti-Rabbit IgG (Invitrogen, A-21206, 1:200), Alexa Fluor® 568 Donkey Anti-Rabbit IgG (Invitrogen, A-10042, 1:200), Alexa Fluor® 488 Donkey Anti-Goat IgG (Invitrogen, A-11055, 1:200), Alexa Fluor® 568 Donkey Anti-Goat IgG (Invitrogen, A-11057, 1:200), Alexa Fluor® 594 Donkey Anti-rat IgG (Invitrogen, A-21209, 1:200), Alexa Fluor® 568 Goat Anti-Armenian Hamster (Abcam, ab175716, 1:200), and Alexa Fluor® 488 Goat Anti-Rabbit (Invitrogen, A-11008, 1:200). After washing three times with cold PBS for five minutes each, the sections or cells were counterstained by DAPI (Cell Signaling, 4083, 1:5000) and sealed with mounting medium (Sigma-Aldrich, F4680). Finally, images were captured by a fluorescence microscopy (Leica DM4000) and further analyzed with ImageJ software.

Immunoblot Analysis

Immunoblot analysis was performed as previously described (Bao et al., 2006a; Cheng et al., 2013; Fang et al., 2014; Fang et al., 2017; Shi et al., 2017a; Shi et al., 2017b; Zhou et al., 2015). In brief, cells were lysed with the RIPA buffer [50 mM TrisHCl (pH7.4), 150 mM NaCl, 2 mM EDTA, 1% (v/v) NP-40, 0.1% (w/v) SDS, protease inhibitor (one tablet per 10 mL RIPA buffer, Roche)] for 20 minutes on ice. For the blots of phosphorylated protein, phosphatase inhibitor (one tablet per 10 mL RIPA buffer, Roche) will be used. The lysates were collected and subjected to SDS-PAGE and blotted onto the PVDF membranes (ASI, XR730). After blockade with 5% (w/v) non-fat milk (RPI, M17200) in TBST, the membranes were incubated with primary antibodies overnight at 4° C. After the incubation of the first antibodies, the membranes were washed three times with TBST for ten minutes each. Then, the membranes were incubated with the second HRP-linked antibodies in the 5% milk for one hour at room temperature. The second HRP-linked antibodies were anti-mouse IgG (Cell signaling, 7076, 1:5000), anti-rabbit IgG (Cell signaling, 7074, 1:5000), and anti-goat IgG (Santa Cruz, sc-2354, 1:5000). After washing three times with TBST for ten minutes each, signals on the membranes were developed in the ECL HRP substrates (Advansta, K-12045) and images were acquired and analyzed by the Image Lab software (Bio-Rad).

Immunohistochemistry (IHC) Analysis

IHC staining was performed by using the Dako REAL EnVision Detection System (Dako) as reported in our previous study (Zhou et al., 2017). In brief, frozen tumor or xenograft sections were fixed with 4% PFA for 10 minutes and then washed three times with cold PBS for five minutes each. The sections were incubated by 0.5% (v/v) $H_2O_2$ (Sigma-Aldrich, H1009) for ten minutes and washed three times with cold PBS for five minutes each. Antigen retrieval was performed by incubating the sections in the boiled antigen unmasking solution (Vector Laboratories) for 15 minutes. After cooling down, the sections were washed three times with cold PBS for five minutes each and blockade by 10% (v/v) serum at room temperature for one hour. After blockade, the sections were incubated with first antibodies overnight at 4° C. The primary antibodies for IHC in this study were anti-TGFβ (R&D Systems, MAB1835, 1:100), TNFα (Abcam, ab6671, 1:300), IL10 (R&D Systems, AF-519, 1:100), and IL1β (R&D Systems, AF-401, 1:100). After washing three times with cold PBS for five minutes each, the anti-goat IgG (1:1000, Vector Laboratories, BA-9500), anti-mouse IgG (1:1000, Vector Laboratories, BA-9200), anti-rabbit IgG (1:1000, Vector Laboratories, BA-1000) secondary antibodies were added to sections and incubated at room temperature for one hour. After washing three times with cold PBS five minutes each, DAB solution (Vector Laboratories) was added to the sections. When optical signal appeared, DAB staining was terminated by placing sides into a running tap water. After counterstaining with hematoxylin (Fisher Scientific, 22-220-102) and dehydration, the sections were mounted with coverslips. The images were captured using a Leica DM4000 Upright Microscope. To evaluate the expression for those cytokines, IHC images were processed with the ImageJ software and relative intensity of each image was calculated with an established method (Jensen, 2013).

Cell Viability Assay

Cell viability assay was performed by using a Cell Titer-Glo Luminescent Cell Viability Assay Kit according to the manufacturer's instruction (Promega, G7571). For this assay, 1,000 cells were seeded on one well of a 96-well plate in 100 µL of stem cell medium. The following day, MK-8931 (10 and 50 µg/mL) or DMSO (control) was added to cells. At Day 7, 50 µL of the Cell-Titer Glo reagent was added to each well and incubated for 15 minutes. Plate was loaded on the VICTOR Multilabel Plate Reader (PerkinElmer) and the readout were recorded and analyzed. All data were normalized to control and presented as mean±SEM.

Tumorsphere Formation Assay

Tumorsphere formation assay was performed as described in our previous study (Shi et al., 2018). Glioma cells (1000 cells) were plated on the one well of a 96-well plate and maintained in the stem cell medium. The following day, MK-8931 (50 µg/mL) or DMSO was added to cells and incubated for four days. At Day 5, the images of tumor-sphere were captured by EVOS FL microscope (AMG). The sizes and numbers of the tumor-sphere in the control and MK-8931 groups were furthered analyzed with ImageJ.

Statistical Analysis

All bar graphs represent mean±SEM unless otherwise indicated. For the survival analysis and correlation between gene expressions in GBM patients, the data were provide by TCGA and downloaded from GlioVis. Bivariate correlation analysis was performed to assess the correlation of two variables in GBM patients. For the survival analysis of GBM patients, the patients were divided into Bace1$^{high}$ and Bace1$^{low}$ groups with GlioVis (http://gliovis.bioinfo.cnio.es/) and Kaplan-Meier survival curves were generated. The log-rank survival analysis was performed with Graph-Pad Prism 5 software to compare significance among different groups. All quantitative data presented were mean±SEM from at least 3 repeats or samples per data point. Experimental details such as number of animals or cells and experimental replication were provided in the figure legends. No statistical method was used to predetermine samples size. The researchers were not blinded. Data inclusion/exclusion criteria was not applied in this study. Significant differences were determined between two groups using the Student's t test or among multiple groups using one-way ANOVA and statistical significance was set at $p<0.05$.

REFERENCES

Bao, S., Wu, Q., McLendon, R. E., Hao, Y., Shi, Q., Hjelmeland, A. B., Dewhirst, M. W., Bigner, D. D., and Rich, J. N. (2006a). Glioma stem cells promote radioresistance by preferential activation of the DNA damage response. Nature 444, 756-760.

Bao, S., Wu, Q., Sathornsumetee, S., Hao, Y., Li, Z., Hjelmeland, A. B., Shi, Q., McLendon, R. E., Bigner, D. D., and Rich, J. N. (2006b). Stem cell-like glioma cells promote tumor angiogenesis through vascular endothelial growth factor. Cancer Res 66, 7843-7848.

Barker, H. E., Paget, J. T. E., Khan, A. A., and Harrington, K. J. (2015). The tumour microenvironment after radiotherapy: mechanisms of resistance and recurrence. Nature Reviews Cancer 15, 409-425.

Binnewies, M., Roberts, E. W., Kersten, K., Chan, V., Fearon, D. F., Merad, M., Coussens, L. M., Gabrilovich, D. I., Ostrand-Rosenberg, S., Hedrick, C. C., et al. (2018). Understanding the tumor immune microenvironment (TIME) for effective therapy. Nat Med 24, 541-550.

Bray, F., Ferlay, J., Soerjomataram, I., Siegel, R. L., Torre, L. A., and Jemal, A. (2018). Global cancer statistics 2018: GLOBOCAN estimates of incidence and mortality worldwide for 36 cancers in 185 countries. Ca-a Cancer Journal for Clinicians 68, 394-424.

Butowski, N., Colman, H., De Groot, J. F., Omuro, A. M., Nayak, L., Wen, P. Y., Cloughesy, T. F., Marimuthu, A., Haidar, S., Perry, A., et al. (2016). Orally administered colony stimulating factor 1 receptor inhibitor PLX3397 in recurrent glioblastoma: an Ivy Foundation Early Phase Clinical Trials Consortium phase II study. Neuro Oncol 18, 557-564.

Cebers, G., Alexander, R. C., Haeberlein, S. B., Han, D., Goldwater, R., Ereshefsky, L., Olsson, T., Ye, N., Rosen, L., Russell, M., et al. (2017). AZD3293: Pharmacokinetic and Pharmacodynamic Effects in Healthy Subjects and Patients with Alzheimer's Disease. J Alzheimers Dis 55, 1039-1053.

Cheng, L., Huang, Z., Zhou, W., Wu, Q., Donnola, S., Liu, J. K., Fang, X., Sloan, A. E., Mao, Y., Lathia, J. D., et al. (2013). Glioblastoma stem cells generate vascular pericytes to support vessel function and tumor growth. Cell 153, 139-152.

Colegio, O. R., Chu, N. Q., Szabo, A. L., Chu, T., Rhebergen, A. M., Jairam, V., Cyrus, N., Brokowski, C. E., Eisenbarth, S. C., Phillips, G. M., et al. (2014). Functional polarization of tumour-associated macrophages by tumour-derived lactic acid. Nature 513, 559-563.

Cooks, T., Pateras, I. S., Jenkins, L. M., Patel, K. M., Robles, A. I., Morris, J., Forshew, T., Appella, E., Gorgoulis, V. G., and Harris, C. C. (2018). Mutant p53 cancers reprogram macrophages to tumor supporting macrophages via exosomal miR-1246. Nat Commun 9, 771.

Darmanis, S., Sloan, S. A., Croote, D., Mignardi, M., Chernikova, S., Samghababi, P., Zhang, Y., Neff, N., Kowarsky, M., Caneda, C., et al. (2017). Single-Cell RNA-Seq Analysis of Infiltrating Neoplastic Cells at the Migrating Front of Human Glioblastoma. Cell Reports 21, 1399-1410.

Deininger, M. H., Seid, K., Engel, S., Meyermann, R., and Schluesener, H. J. (2000). Allograft inflammatory factor-1 defines a distinct subset of infiltrating macrophages/microglial cells in rat and human gliomas. Acta Neuropathol 100, 673-680.

Egan, M. F., Kost, J., Tariot, P. N., Aisen, P. S., Cummings, J. L., Vellas, B., Sur, C., Mukai, Y., Voss, T., Furtek, C., et al. (2018). Randomized Trial of Verubecestat for Mild-to-Moderate Alzheimer's Disease. New England Journal of Medicine 378, 1691-1703.

Egan, M. F., Kost, J., Voss, T., Mukai, Y., Aisen, P. S., Cummings, J. L., Tariot, P. N., Vellas, B., van Dyck, C. H., Boada, M., et al. (2019). Randomized Trial of Verubecestat for Prodromal Alzheimer's Disease. N Engl J Med 380, 1408-1420.

Eketjall, S., Janson, J., Kaspersson, K., Bogstedt, A., Jeppsson, F., Falting, J., Haeberlein, S. B., Kugler, A. R., Alexander, R. C., and Cebers, G. (2016). AZD3293: A Novel, Orally Active BACE1 Inhibitor with High Potency and Permeability and Markedly Slow Off-Rate Kinetics. J Alzheimers Dis 50, 1109-1123.

Fang, X., Huang, Z., Zhou, W., Wu, Q., Sloan, A. E., Ouyang, G., McLendon, R. E., Yu, J. S., Rich, J. N., and Bao, S. (2014). The zinc finger transcription factor ZFX is required for maintaining the tumorigenic potential of glioblastoma stem cells. Stem Cells 32, 2033-2047.

Fang, X., Zhou, W., Wu, Q., Huang, Z., Shi, Y., Yang, K., Chen, C., Xie, Q., Mack, S. C., Wang, X., et al. (2017). Deubiquitinase USP13 maintains glioblastoma stem cells by antagonizing FBXL14-mediated Myc ubiquitination. J Exp Med 214, 245-267.

Farah, M. H., Pan, B. H., Hoffman, P. N., Ferraris, D., Tsukamoto, T., Nguyen, T., Wong, P. C., Price, D. L., Slusher, B. S., and Griffin, J. W. (2011). Reduced BACE1 Activity Enhances Clearance of Myelin Debris and Regeneration of Axons in the Injured Peripheral Nervous System. Journal of Neuroscience 31, 5744-5754.

Filley, A. C., Henriquez, M., and Dey, M. (2017). Recurrent glioma clinical trial, CheckMate-143: the game is not over yet. Oncotarget 8, 91779-91794.

Fitzmaurice, C., Akinyemiju, T. F., Al Lami, F. H., Alam, T., Alizadeh-Navaei, R., Allen, C., Alsharif, U., Alvis-Guzman, N., Amini, E., Anderson, B. O., et al. (2018). Global, Regional, and National Cancer Incidence, Mortality, Years of Life Lost, Years Lived With Disability, and Disability-Adjusted Life-Years for 29 Cancer Groups, 1990 to 2016 A Systematic Analysis for the Global Burden of Disease Study. Jama Oncology 4, 1553-1568.

Franklin, R. A., Liao, W., Sarkar, A., Kim, M. V., Bivona, M. R., Liu, K., Pamer, E. G., and Li, M. O. (2014). The cellular and molecular origin of tumor-associated macrophages. Science 344, 921-925.

Gelderblom, H., Cropet, C., Chevreau, C., Boyle, R., Tattersall, M., Stacchiotti, S., Italiano, A., Piperno-Neumann, S., Le Cesne, A., Ferraresi, V., et al. (2018). Nilotinib in locally advanced pigmented villonodular synovitis: a multicentre, open-label, single-arm, phase 2 trial. Lancet Oncol 19, 639-648.

Genard, G., Lucas, S., and Michiels, C. (2017). Reprogramming of Tumor-Associated Macrophages with Anticancer Therapies: Radiotherapy versus Chemo- and immunotherapies. Frontiers in Immunology 8.

Glass, R., and Synowitz, M. (2014). CNS macrophages and peripheral myeloid cells in brain tumours. Acta Neuropathologica 128, 347-362.

Guerriero, J. L. (2018). Macrophages: The Road Less Traveled, Changing Anticancer Therapy. Trends Mol Med 24, 472-489.

Guryanova, O. A., Wu, Q., Cheng, L., Lathia, J. D., Huang, Z., Yang, J., MacSwords, J., Eyler, C. E., McLendon, R. E., Heddleston, J. M., et al. (2011). Nonreceptor tyrosine kinase BMX maintains self-renewal and tumorigenic potential of glioblastoma stem cells by activating STAT3. Cancer Cell 19, 498-511.

Hambardzumyan, D., Gutmann, D. H., and Kettenmann, H. (2016). The role of microglia and macrophages in glioma maintenance and progression. Nat Neurosci 19, 20-27.

Highfill, S. L., Cui, Y. Z., Giles, A. J., Smith, J. P., Zhang, H., Morse, E., Kaplan, R. N., and Mackall, C. L. (2014). Disruption of CXCR2-Mediated MDSC Tumor Trafficking Enhances Anti-PD1 Efficacy. Science Translational Medicine 6.

Hu, W., Li, X., Zhang, C., Yang, Y., Jiang, J., and Wu, C. (2016). Tumor-associated macrophages in cancers. Clin Transl Oncol 18, 251-258.

Hussain, I., Powell, D., Howlett, D. R., Tew, D. G., Week, T. D., Chapman, C., Gloger, I. S., Murphy, K. E., Southan, C. D., Ryan, D. M., et al. (1999). Identification of a novel aspartic protease (Asp 2) as beta-secretase. Molecular and Cellular Neuroscience 14, 419-427.

Jensen, E. C. (2013). Quantitative Analysis of Histological Staining and Fluorescence Using ImageJ. Anatomical Record-Advances in Integrative Anatomy and Evolutionary Biology 296, 378-381.

Jung, K. Y., Cho, S. W., Kim, Y. A., Kim, D., Oh, B. C., Park, D. J., and Park, Y. J. (2015). Cancers with Higher Density of Tumor-Associated Macrophages Were Associated with Poor Survival Rates. Journal of Pathology and Translational Medicine 49, 318-324.

Kennedy, M. E., Stamford, A. W., Chen, X., Cox, K., Cumming, J. N., Dockendorf, M. F., Egan, M., Ereshefsky, L., Hodgson, R. A., Hyde, L. A., et al. (2016). The BACE1 inhibitor verubecestat (MK-8931) reduces CNS beta-amyloid in animal models and in Alzheimer's disease patients. Science Translational Medicine 8.

Kioi, M., Vogel, H., Schultz, G., Hoffman, R. M., Harsh, G. R., and Brown, J. M. (2010). Inhibition of vasculogenesis, but not angiogenesis, prevents the recurrence of glioblastoma after irradiation in mice. J Clin Invest 120, 694-705.

Komohara, Y., Ohnishi, K., Kuratsu, J., and Takeya, M. (2008). Possible involvement of the M2 anti-inflammatory macrophage phenotype in growth of human gliomas. J Pathol 216, 15-24.

Kuang, D. M., Zhao, Q. Y., Peng, C., Xu, J., Zhang, J. P., Wu, C. Y., and Zheng, L. M. (2009). Activated monocytes in peritumoral stroma of hepatocellular carcinoma foster immune privilege and disease progression through PD-L1. Journal of Experimental Medicine 206, 1327-1337.

Lee, M., Park, J. J., Ko, Y. G., and Lee, Y. S. (2012). Cleavage of ST6Gal I by radiation-induced BACE1 inhibits golgi-anchored ST6Gal I-mediated sialylation of integrin beta1 and migration in colon cancer cells. Radiat Oncol 7, 47.

Li, Z., Bao, S., Wu, Q., Wang, H., Eyler, C., Sathornsumetee, S., Shi, Q., Cao, Y., Lathia, J., McLendon, R. E., et al. (2009). Hypoxia-inducible factors regulate tumorigenic capacity of glioma stem cells. Cancer Cell 15, 501-513.

Liu, L. J., Fissel, J. A., Tasnim, A., Borzan, J., Gocke, A., Calabresi, P. A., and Farah, M. H. (2016). Increased TNFR1 expression and signaling in injured peripheral nerves of mice with reduced BACE1 activity. Neurobiology of Disease 93, 21-27.

Lopez Lopez, C., Caputo, A., Liu, F., Riviere, M. E., Rouzade-Dominguez, M. L., Thomas, R. G., Langbaum, J. B., Lenz, R., Reiman, E. M., Graf, A., et al. (2017). The Alzheimer's Prevention Initiative Generation Program: Evaluating CNP520 Efficacy in the Prevention of Alzheimer's Disease. J Prev Alzheimers Dis 4, 242-246.

Mantovani, A., Marchesi, F., Malesci, A., Laghi, L., and Allavena, P. (2017). Tumour-associated macrophages as treatment targets in oncology. Nature Reviews Clinical Oncology 14, 399-416.

Menon, S., Shin, S., and Dy, G. (2016). Advances in Cancer Immunotherapy in Solid Tumors. Cancers (Basel) 8.

Mia, S., Warnecke, A., Zhang, X. M., Malmstrom, V., and Harris, R. A. (2014). An optimized Protocol for Human M2 Macrophages using M-CSF and IL-4/IL-10/TGF-beta Yields a Dominant Immunosuppressive Phenotype. Scandinavian Journal of Immunology 79, 305-314.

Munn, D. H., and Bronte, V. (2016). Immune suppressive mechanisms in the tumor microenvironment. Current Opinion in Immunology 39, 1-6.

Murray, P. J. (2017). Macrophage Polarization. Annu Rev Physiol 79, 541-566. Neumann, U., Ufer, M., Jacobson, L. H., Rouzade-Dominguez, M. L., Huledal, G., Kolly, C., Luond, R. M., Machauer, R., Veenstra, S. J., Hurth, K., et al. (2018). The BACE-1 inhibitor CNP520 for prevention trials in Alzheimer's disease. EMBO Mol Med 10.

Noy, R., and Pollard, J. W. (2014). Tumor-associated macrophages: from mechanisms to therapy. Immunity 41, 49-61.

Panza, F., Lozupone, M., Solfrizzi, V., Sardone, R., Piccininni, C., Dibello, V., Stallone, R., Giannelli, G., Bellomo, A., Greco, A., et al. (2018). BACE inhibitors in clinical development for the treatment of Alzheimer's disease. Expert Review of Neurotherapeutics 18, 847-857.

Papadopoulos, K. P., Gluck, L., Martin, L. P., Olszanski, A. J., Tolcher, A. W., Ngarmchamnanrith, G., Rasmussen, E., Amore, B. M., Nagorsen, D., Hill, J. S., et al. (2017). First-in-Human Study of AMG 820, a Monoclonal Anti-Colony-Stimulating Factor 1 Receptor Antibody, in Patients with Advanced Solid Tumors. Clin Cancer Res 23, 5703-5710.

Pyonteck, S. M., Akkari, L., Schuhmacher, A. J., Bowman, R. L., Sevenich, L., Quail, D. F., Olson, O. C., Quick, M. L., Huse, J. T., Teijeiro, V., et al. (2013). CSF-1R inhibition alters macrophage polarization and blocks glioma progression. Nature Medicine 19, 1264-+.

Qian, B. Z., and Pollard, J. W. (2010). Macrophage Diversity Enhances Tumor Progression and Metastasis. Cell 141, 39-51.

Quail, D. F., and Joyce, J. A. (2017). The Microenvironmental Landscape of Brain Tumors. Cancer Cell 31, 326-341.

Ruffell, B., Chang-Strachan, D., Chan, V., Rosenbusch, A., Ho, C. M., Pryer, N., Daniel, D., Hwang, E. S., Rugo, H. S., and Coussens, L. M. (2014). Macrophage IL-10 blocks CD8+ T cell-dependent responses to chemotherapy by suppressing IL-12 expression in intratumoral dendritic cells. Cancer Cell 26, 623-637.

Ruffell, B., and Coussens, L. M. (2015). Macrophages and therapeutic resistance in cancer. Cancer Cell 27, 462-472.

Scott, J. D., Li, S. W., Brunskill, A. P. J., Chen, X., Cox, K., Cumming, O. N., Forman, M., Gilbert, E. J., Hodgson, R. A., Hyde, L. A., et al. (2016). Discovery of the 3-Imino-1,2,4-thiadiazinane 1,1-Dioxide Derivative Verubecestat (MK-8931)-A beta-Site Amyloid Precursor Protein Cleaving Enzyme 1 Inhibitor for the Treatment of Alzheimer's Disease. Journal of Medicinal Chemistry 59, 10435-10450.

Sharma, P., Hu-Lieskovan, S., Wargo, J. A., and Ribas, A. (2017). Primary, Adaptive, and Acquired Resistance to Cancer Immunotherapy. Cell 168, 707-723.

Shi, Y., Guryanova, O. A., Zhou, W., Liu, C., Huang, Z., Fang, X., Wang, X., Chen, C., Wu, Q., He, Z., et al. (2018). Ibrutinib inactivates BMX-STAT3 in glioma stem cells to impair malignant growth and radioresistance. Sci Transl Med 10.

Shi, Y., Ping, Y. F., Zhou, W., He, Z. C., Chen, C., Bian, B. S., Zhang, L., Chen, L., Lan, X., Zhang, X. C., et al. (2017a). Tumour-associated macrophages secrete pleiotrophin to promote PTPRZ1 signalling in glioblastoma stem cells for tumour growth. Nat Commun 8, 15080.

Shi, Y., Zhou, W., Cheng, L., Chen, C., Huang, Z., Fang, X., Wu, Q., He, Z., Xu, S., Lathia, J. D., et al. (2017b).

Tetraspanin CD9 stabilizes gp130 by preventing its ubiquitin-dependent lysosomal degradation to promote STAT3 activation in glioma stem cells. Cell Death Differ 24, 167-180.

Sica, A., Larghi, P., Mancino, A., Rubino, L., Porta, C., Totaro, M. G., Rimoldi, M., Biswas, S. K., Allavena, P., and Mantovani, A. (2008). Macrophage polarization in tumour progression. Semin Cancer Biol 18, 349-355.

Sica, A., and Mantovani, A. (2012). Macrophage plasticity and polarization: in vivo veritas. Journal of Clinical Investigation 122, 787-795.

Sica, A., Schioppa, T., Mantovani, A., and Allavena, P. (2006). Tumour-associated macrophages are a distinct M2 polarised population promoting tumour progression: Potential targets of anti-cancer therapy. European Journal of Cancer 42, 717-727.

Sinha, S., Anderson, J. P., Barbour, R., Basi, G. S., Caccavello, R., Davis, D., Doan, M., Dovey, H. F., Frigon, N., Hong, J., et al. (1999). Purification and cloning of amyloid precursor protein beta-secretase from human brain. Nature 402, 537-540.

Sorensen, M. D., Dahlrot, R. H., Boldt, H. B., Hansen, S., and Kristensen, B. W. (2018). Tumour-associated microglia/macrophages predict poor prognosis in high-grade gliomas and correlate with an aggressive tumour subtype. Neuropathol Appl Neurobiol 44, 185-206.

Sperduto, P. W., Chao, S. T., Sneed, P. K., Luo, X. H., Suh, J., Roberge, D., Bhatt, A., Jensen, A. W., Brown, P. D., Shih, H., et al. (2010). Diagnosis-Specific Prognostic Factors, Indexes, and Treatment Outcomes for Patients with Newly Diagnosed Brain Metastases: A Multi-Institutional Analysis of 4,259 Patients. International Journal of Radiation Oncology Biology Physics 77, 655-661.

Su, S., Zhao, J., Xing, Y., Zhang, X., Liu, J., Ouyang, Q., Chen, J., Su, F., Liu, Q., and Song, E. (2018). Immune Checkpoint Inhibition Overcomes ADCP-Induced Immunosuppression by Macrophages. Cell 175, 442-457 e423.

Thaisrivongs, D. K., Miller, S. P., Molinaro, C., Chen, Q. H., Song, Z. J., Tan, L. S., Chen, L., Chen, W. Y., Lekhal, A., Pulicare, S. K., et al. (2016). Synthesis of Verubecestat, a BACE1 Inhibitor for the Treatment of Alzheimer's Disease. Organic Letters 18, 5780-5783.

van Wilgenburg, B., Browne, C., Vowles, J., and Cowley, S. A. (2013). Efficient, long term production of monocyte-derived macrophages from human pluripotent stem cells under partly-defined and fully-defined conditions. PLoS One 8, e71098.

Vassar, R., Bennett, B. D., Babu-Khan, S., Kahn, S., Mendiaz, E. A., Denis, P., Teplow, D. B., Ross, S., Amarante, P., Loeloff, R., et al. (1999). beta-secretase cleavage of Alzheimer's amyloid precursor protein by the transmembrane aspartic protease BACE. Science 286, 735-741.

Vatner, R. E., and Formenti, S. C. (2015). Myeloid-Derived Cells in Tumors: Effects of Radiation. Seminars in Radiation Oncology 25, 18-27.

Wang, Q., Hu, B., Hu, X., Kim, H., Squatrito, M., Scarpace, L., deCarvalho, A. C., Lyu, S., Li, P., Li, Y., et al. (2017). Tumor Evolution of Glioma-Intrinsic Gene Expression Subtypes Associates with Immunological Changes in the Microenvironment. Cancer Cell 32, 42-56 e46.

Wang, X., Prager, B. C., Wu, Q., Kim, L. J. Y., Gimple, R. C., Shi, Y., Yang, K., Morton, A. R., Zhou, W., Zhu, Z., et al. (2018). Reciprocal Signaling between Glioblastoma Stem Cells and Differentiated Tumor Cells Promotes Malignant Progression. Cell Stem Cell 22, 514-528 e515.

Weischenfeldt, J., and Porse, B. (2008). Bone Marrow-Derived Macrophages (BMM): Isolation and Applications. CSH Protoc 2008, pdb prot5080.

Xie, Q., Wu, T. P., Gimple, R. C., Li, Z., Prager, B. C., Wu, Q. L., Yu, Y., Wang, P. C., Wang, Y. S., Gorkin, D. U., et al. (2018). N-6-methyladenine DNA Modification in Glioblastoma. Cell 175, 1228-+.

Yan, R. (2017). Physiological Functions of the beta-Site Amyloid Precursor Protein Cleaving Enzyme 1 and 2. Front Mol Neurosci 10, 97.

Yan, R., and Vassar, R. (2014a). Targeting the beta secretase BACE1 for Alzheimer's disease therapy. Lancet Neurol 13, 319-329.

Yan, R. Q., Bienkowski, M. J., Shuck, M. E., Miao, H. Y., Tory, M. C., Pauley, A. M., Brashler, J. R., Stratman, N. C., Mathews, W. R., Buhl, A. E., et al. (1999). Membrane-anchored aspartyl protease with Alzheimer's disease beta-secretase activity. Nature 402, 533-537.

Yan, R. Q., and Vassar, R. (2014b). Targeting the beta secretase BACE1 for Alzheimer's disease therapy. Lancet Neurology 13, 319-329.

Yanagimachi, M. D., Niwa, A., Tanaka, T., Honda-Ozaki, F., Nishimoto, S., Murata, Y., Yasumi, T., Ito, J., Tomida, S., Oshima, K., et al. (2013). Robust and highly-efficient differentiation of functional monocytic cells from human pluripotent stem cells under serum- and feeder cell-free conditions. PLoS One 8, e59243.

Yang, L., and Zhang, Y. (2017). Tumor-associated macrophages: from basic research to clinical application. J Hematol Oncol 10, 58.

Yu, H., Pardoll, D., and Jove, R. (2009). STATs in cancer inflammation and immunity: a leading role for STAT3. Nat Rev Cancer 9, 798-809.

Zhou, W., and Bao, S. (2014a). Reciprocal Supportive Interplay between Glioblastoma and Tumor-Associated Macrophages. Cancers (Basel) 6, 723-740.

Zhou, W., Chen, C., Shi, Y., Wu, Q., Gimple, R. C., Fang, X., Huang, Z., Zhai, K., Ke, S. Q., Ping, Y. F., et al. (2017). Targeting Glioma Stem Cell-Derived Pericytes Disrupts the Blood-Tumor Barrier and Improves Chemotherapeutic Efficacy. Cell Stem Cell 21, 591-603 e594.

Zhou, W., Ke, S. Q., Huang, Z., Flavahan, W., Fang, X., Paul, J., Wu, L., Sloan, A. E., McLendon, R. E., Li, X., et al. (2015). Periostin secreted by glioblastoma stem cells recruits M2 tumour-associated macrophages and promotes malignant growth. Nat Cell Biol 17, 170-182.

Zhou, W. C., and Bao, S. D. (2014b). Reciprocal Supportive Interplay between Glioblastoma and Tumor-Associated Macrophages. Cancers 6, 723-740.

All publications and patents mentioned in the specification and/or listed below are herein incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the relevant fields are intended to be within the scope described herein.

We claim:

1. A method of treating a subject with cancer comprising:
   a) treating a subject having cancer with radiation, wherein said cancer is selected from the group consisting of: a brain cancer, glioblastoma multiforme, brain metastases, lung adenocarcinoma, liver cancer, and gastric cancer, and
   b) administering a BACE1 inhibitor to said subject, wherein said BACE1 inhibitor is selected from the group consisting of: MK-8931, PF-06751979, AZD3839, CNP520, E2609, AZD3293, and JNJ-54861911.

2. The method of claim 1, wherein said administering comprises providing said BACE1 inhibitor to said subject in the form of oral pills that said patient takes themselves.

3. The method of claim 1, wherein said administering comprises injecting said BACE1 inhibitor into said subject.

4. The method of claim 1, further comprising: c) repeating said administering daily for at least one week or at least three weeks.

5. The method of claim 1, wherein said administering comprises administering 0.05 mg per kg of the subject to 50 mg per kg of the subject, or administering a total dose of 3-1000 mg.

6. The method of claim 1, wherein said treating with radiation occurs at least about 3 hours prior to said administering.

7. The method of claim 1, wherein said administering occurs no later than 6 days after said treating with radiation.

8. The method of claim 1, wherein said radiation is low-dose radiation.

9. The method of claim 8, wherein said low-dose radiation provides between 0.1-10 Gy of radiation to said subject.

10. The method of claim 1, wherein said subject is a human.

11. The method of claim 1, wherein said BACE1 inhibitor comprises MK-8931.

12. The method of claim 1, further comprising: c) administering said subject an immune checkpoint inhibitor.

13. A method of treating a subject with cancer comprising: administering a BACE1 inhibitor to said subject, wherein said BACE1 inhibitor is selected from the group consisting of: MK-8931, PF-06751979, AZD3839, CNP520, E2609, AZD3293, and JNJ-54861911, and
   wherein said subject has cancer, and wherein said cancer is selected from the group consisting of: a brain cancer, glioblastoma multiforme, brain metastases, lung adenocarcinoma, liver cancer, and gastric cancer.

14. The method of claim 13, wherein said BACE1 inhibitor comprises MK-8931.

15. The method of claim 13, wherein said administering comprises: i) providing said BACE1 inhibitor to said subject in the form of oral pills that said patient takes themselves, or ii) injecting said BACE1 inhibitor into said subject.

16. The method of claim 13, further comprising: repeating said administering daily for at least one week or at least three weeks, and/or wherein said subject is a human.

17. The method of claim 13, further comprising: i) treating a subject with radiation prior to said administering, and/or ii) administering said subject an immune checkpoint inhibitor.

18. The method of claim 1, wherein said subject has glioblastoma multiforme.

19. The method of claim 18, wherein said BACE1 inhibitor comprises MK-8931.

20. The method of claim 13, wherein said subject has glioblastoma multiforme.

21. The method of claim 20, wherein said BACE1 inhibitor comprises MK-8931.

* * * * *